(12) United States Patent
Levy et al.

(10) Patent No.: US 12,156,940 B1
(45) Date of Patent: *Dec. 3, 2024

(54) MANUFACTURING OF BUPIVACAINE MULTIVESICULAR LIPOSOMES

(71) Applicant: Pacira Pharmaceuticals, Inc., San Diego, CA (US)

(72) Inventors: Eran Levy, San Diego, CA (US); Jeffrey S. Hall, San Diego, CA (US); John J. Grigsby, Jr., San Diego, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/761,863

(22) Filed: Jul. 2, 2024

Related U.S. Application Data

(60) Provisional application No. 63/649,872, filed on May 20, 2024.

(51) Int. Cl.
| | |
|---|---|
| *A61K 9/127* | (2006.01) |
| *A61K 31/445* | (2006.01) |
| *A61K 47/14* | (2017.01) |
| *A61K 47/24* | (2006.01) |
| *A61K 47/28* | (2006.01) |

(52) U.S. Cl.
CPC .......... *A61K 9/127* (2013.01); *A61K 31/445* (2013.01); *A61K 47/14* (2013.01); *A61K 47/24* (2013.01); *A61K 47/28* (2013.01)

(58) Field of Classification Search
None
See application file for complete search history.

(56) References Cited

U.S. PATENT DOCUMENTS

| | | |
|---|---|---|
| 3,684,251 A | 8/1972 | Bowling |
| 3,946,994 A | 3/1976 | Mertz et al. |
| 4,026,817 A | 5/1977 | Ciuti et al. |
| 4,078,052 A | 3/1978 | Papahadjopoulos |
| 4,089,801 A | 5/1978 | Schneider |
| 4,113,765 A | 9/1978 | Richardson et al. |
| 4,145,410 A | 3/1979 | Sears |
| 4,224,179 A | 9/1980 | Schneider |

(Continued)

FOREIGN PATENT DOCUMENTS

| | | |
|---|---|---|
| CA | 2078666 | 9/1991 |
| CA | 1323568 | 10/1993 |

(Continued)

OTHER PUBLICATIONS

Kapoor et al., May 2017, Liposomal Drug Product Development and Quality: Current US Experience and Perspective, The AAPS Journal, 19(3):632-641.

(Continued)

*Primary Examiner* — Isaac Shomer
(74) *Attorney, Agent, or Firm* — Knobbe, Martens, Olson & Bear, LLP

(57) ABSTRACT

Embodiments of the present disclosure relates to a new and improved large scale commercial manufacturing process of making bupivacaine multivesicular liposomes (MVLs). Batches of bupivacaine MVLs prepared by the new process have high yields, improved stabilities, and desired particle size distributions.

30 Claims, 12 Drawing Sheets

(56) References Cited

U.S. PATENT DOCUMENTS

| | | |
|---|---|---|
| 4,235,587 A | 11/1980 | Miles |
| 4,235,871 A | 11/1980 | Papahadjopoulos et al. |
| 4,310,506 A | 1/1982 | Baldeschwieler et al. |
| 4,394,372 A | 7/1983 | Taylor |
| 4,420,398 A | 12/1983 | Castino |
| 4,454,083 A | 6/1984 | Brown et al. |
| 4,478,824 A | 10/1984 | Franco et al. |
| 4,522,803 A | 6/1985 | Lenk et al. |
| 4,588,578 A | 5/1986 | Fountain et al. |
| 4,590,030 A | 5/1986 | Gillner et al. |
| 4,599,227 A | 7/1986 | Dees et al. |
| 4,599,342 A | 7/1986 | LaHann |
| 4,610,868 A | 9/1986 | Fountain et al. |
| 4,622,219 A | 11/1986 | Haynes |
| 4,644,056 A | 2/1987 | Kothe et al. |
| 4,652,441 A | 3/1987 | Okada et al. |
| 4,668,580 A | 5/1987 | Dahm et al. |
| 4,711,782 A | 12/1987 | Okada et al. |
| 4,725,442 A | 2/1988 | Haynes |
| 4,744,989 A | 5/1988 | Payne et al. |
| 4,752,425 A | 6/1988 | Martin et al. |
| 4,761,255 A | 8/1988 | Dahm et al. |
| 4,761,288 A | 8/1988 | Mezei |
| 4,769,250 A | 9/1988 | Forssen |
| 4,776,991 A | 10/1988 | Farmer et al. |
| 4,781,831 A | 11/1988 | Goldsmith |
| 4,781,871 A | 11/1988 | West, III et al. |
| 4,788,001 A | 11/1988 | Narula |
| 4,844,620 A | 7/1989 | Lissant et al. |
| 4,844,904 A | 7/1989 | Hamaguchi et al. |
| 4,861,597 A | 8/1989 | Kida et al. |
| 4,877,561 A | 10/1989 | Iga et al. |
| 4,877,619 A | 10/1989 | Richer |
| 4,908,463 A | 3/1990 | Bottelberghe |
| 4,920,016 A | 4/1990 | Allen et al. |
| 4,921,644 A | 5/1990 | Lau et al. |
| 4,921,853 A | 5/1990 | LeBlanc |
| 4,937,078 A | 6/1990 | Mezei et al. |
| 4,946,683 A | 8/1990 | Forssen |
| 4,956,290 A | 9/1990 | Harrison et al. |
| 5,000,959 A | 3/1991 | Iga et al. |
| 5,004,611 A | 4/1991 | Leigh |
| 5,013,556 A | 5/1991 | Woodle et al. |
| 5,019,394 A | 5/1991 | Hamaguchi et al. |
| 5,021,200 A | 6/1991 | Vanlerberghe et al. |
| 5,049,392 A | 9/1991 | Weiner et al. |
| 5,069,936 A | 12/1991 | Yen |
| 5,077,056 A | 12/1991 | Bally et al. |
| 5,091,187 A | 2/1992 | Haynes |
| 5,094,854 A | 3/1992 | Ogawa et al. |
| 5,100,591 A | 3/1992 | Leclef et al. |
| 5,141,674 A | 8/1992 | Leigh |
| 5,147,134 A | 9/1992 | Bradley et al. |
| 5,169,637 A | 12/1992 | Lenk et al. |
| 5,186,941 A | 2/1993 | Callahan et al. |
| 5,192,549 A | 3/1993 | Barenolz et al. |
| 5,204,112 A | 4/1993 | Hope et al. |
| 5,211,955 A | 5/1993 | Legros et al. |
| 5,225,212 A | 7/1993 | Martin et al. |
| 5,227,165 A | 7/1993 | Domb et al. |
| 5,227,170 A | 7/1993 | Sullivan |
| 5,244,678 A | 9/1993 | Legros et al. |
| 5,246,707 A | 9/1993 | Haynes |
| 5,261,903 A | 11/1993 | Dhaliwal et al. |
| 5,292,701 A | 3/1994 | Glemza et al. |
| 5,321,012 A | 6/1994 | Mayer et al. |
| 5,334,381 A | 8/1994 | Unger |
| 5,334,391 A | 8/1994 | Clark et al. |
| 5,364,632 A | 11/1994 | Benita et al. |
| 5,387,387 A | 2/1995 | James et al. |
| 5,393,530 A | 2/1995 | Schneider et al. |
| 5,407,660 A | 4/1995 | Bosworth et al. |
| 5,415,867 A | 5/1995 | Minchey et al. |
| 5,422,120 A | 6/1995 | Kim |
| 5,451,408 A | 9/1995 | Mezei et al. |
| 5,455,044 A | 10/1995 | Kim et al. |
| RE35,192 E | 3/1996 | Reese |
| 5,533,526 A | 7/1996 | Goldberg |
| 5,543,158 A | 8/1996 | Gref et al. |
| 5,576,017 A | 11/1996 | Kim |
| 5,576,018 A | 11/1996 | Kim et al. |
| 5,589,189 A | 12/1996 | Moynihan |
| 5,635,205 A | 6/1997 | Nyqvist et al. |
| 5,658,898 A | 8/1997 | Weder et al. |
| 5,662,931 A | 9/1997 | Munechika et al. |
| 5,681,464 A | 10/1997 | Larsson |
| 5,700,482 A | 12/1997 | Frederiksen et al. |
| 5,708,011 A | 1/1998 | Bardsley et al. |
| 5,723,147 A | 3/1998 | Kim et al. |
| 5,766,627 A | 6/1998 | Sankaram et al. |
| 5,770,222 A | 6/1998 | Unger et al. |
| 5,776,486 A | 7/1998 | Castor et al. |
| 5,776,915 A | 7/1998 | Peterson et al. |
| 5,807,573 A | 9/1998 | Ljusberg-Wahren et al. |
| 5,814,335 A | 9/1998 | Webb et al. |
| 5,827,533 A | 10/1998 | Needham |
| 5,837,282 A | 11/1998 | Fenske et al. |
| 5,849,763 A | 12/1998 | Bardsley et al. |
| 5,853,755 A | 12/1998 | Foldvari |
| 5,865,184 A | 2/1999 | Takiguchi |
| 5,879,672 A | 3/1999 | Davis et al. |
| 5,882,679 A | 3/1999 | Needham |
| 5,885,260 A | 3/1999 | Mehl, Sr. et al. |
| 5,891,467 A | 4/1999 | Willis |
| 5,891,842 A | 4/1999 | Kream |
| 5,895,661 A | 4/1999 | Tournier et al. |
| 5,910,502 A | 6/1999 | Gennery |
| 5,912,271 A | 6/1999 | Brodin et al. |
| 5,919,804 A | 7/1999 | Gennery |
| 5,922,340 A | 7/1999 | Berde et al. |
| 5,942,253 A | 8/1999 | Gombotz et al. |
| 5,945,126 A | 8/1999 | Thanoo et al. |
| 5,945,435 A | 8/1999 | Evetts |
| 5,947,689 A | 9/1999 | Schick |
| 5,948,441 A | 9/1999 | Lenk et al. |
| 5,955,087 A | 9/1999 | Whittle et al. |
| 5,955,479 A | 9/1999 | Bardsley et al. |
| 5,962,016 A | 10/1999 | Willis |
| 5,962,532 A | 10/1999 | Campbell et al. |
| 5,977,326 A | 11/1999 | Scheinmann et al. |
| 5,980,927 A | 11/1999 | Nelson et al. |
| 5,980,937 A | 11/1999 | Tournier et al. |
| 5,997,899 A | 12/1999 | Ye et al. |
| 6,007,838 A | 12/1999 | Alving et al. |
| 6,033,708 A | 3/2000 | Kwasiborski et al. |
| 6,045,824 A | 4/2000 | Kim et al. |
| 6,046,187 A | 4/2000 | Berde et al. |
| 6,048,545 A | 4/2000 | Keller et al. |
| 6,066,331 A | 5/2000 | Barenholz et al. |
| 6,069,155 A | 5/2000 | Mather et al. |
| 6,071,534 A | 6/2000 | Kim et al. |
| 6,103,741 A | 8/2000 | Bardsley et al. |
| 6,106,858 A | 8/2000 | Ye et al. |
| 6,120,797 A | 9/2000 | Meers et al. |
| 6,132,766 A | 10/2000 | Sankaram et al. |
| 6,149,937 A | 11/2000 | Camu et al. |
| 6,171,613 B1 | 1/2001 | Ye et al. |
| 6,193,998 B1 | 2/2001 | Ye et al. |
| 6,217,899 B1 | 4/2001 | Benameur et al. |
| 6,221,385 B1 | 4/2001 | Camu et al. |
| 6,221,401 B1 | 4/2001 | Zasadzinski et al. |
| 6,238,702 B1 | 5/2001 | Berde et al. |
| 6,241,999 B1 | 6/2001 | Ye et al. |
| 6,264,988 B1 | 7/2001 | Yen |
| 6,270,802 B1 | 8/2001 | Thanoo et al. |
| 6,287,587 B2 | 9/2001 | Shigeyuki et al. |
| 6,306,432 B1 | 10/2001 | Shirley et al. |
| 6,355,267 B1 | 3/2002 | Collins |
| 6,399,094 B1 | 6/2002 | Brandl et al. |
| 6,417,201 B1 | 7/2002 | Bardsley et al. |
| 8,182,835 B2 | 5/2012 | Kim et al. |
| 8,834,921 B2 | 9/2014 | Kim et al. |
| 9,192,575 B2 | 11/2015 | Kim et al. |
| 9,205,052 B2 | 12/2015 | Kim et al. |

(56) References Cited

U.S. PATENT DOCUMENTS

| | | | |
|---|---|---|---|
| 9,585,838 B2* | 3/2017 | Hartounian | A61K 31/7068 |
| 9,730,892 B2 | 7/2017 | Schutt et al. | |
| 9,724,302 B2 | 8/2017 | Schutt et al. | |
| 9,737,482 B2 | 8/2017 | Schutt et al. | |
| 9,737,483 B2 | 8/2017 | Schutt et al. | |
| 9,757,336 B2 | 9/2017 | Schutt et al. | |
| 9,808,424 B2 | 11/2017 | Schutt et al. | |
| 10,045,941 B2 | 8/2018 | Schutt et al. | |
| 10,398,648 B2 | 9/2019 | Schutt et al. | |
| 10,842,745 B2 | 11/2020 | Barenholz et al. | |
| 11,033,495 B1 | 6/2021 | Hall et al. | |
| 11,185,506 B1 | 11/2021 | Hall et al. | |
| 11,179,336 B1 | 12/2021 | Hall et al. | |
| 11,278,494 B1 | 3/2022 | Hall et al. | |
| 11,304,904 B1 | 4/2022 | Hall et al. | |
| 11,311,486 B1 | 4/2022 | Hall et al. | |
| 11,357,727 B1 | 6/2022 | Hall et al. | |
| 11,426,348 B2 | 8/2022 | Hall et al. | |
| 11,452,691 B1 | 9/2022 | Hall et al. | |
| 11,819,574 B2 | 11/2023 | Hall et al. | |
| 11,819,575 B2 | 11/2023 | Hall et al. | |
| 11,925,706 B2 | 3/2024 | Hall et al. | |
| 2002/0039596 A1 | 4/2002 | Hartounian et al. | |
| 2002/0041895 A1 | 4/2002 | Gregoriadis et al. | |
| 2003/0201230 A1 | 10/2003 | Kopf | |
| 2004/0247659 A1 | 12/2004 | Eibl | |
| 2010/0305160 A1* | 12/2010 | Brummett | A61P 29/00 514/330 |
| 2011/0244029 A1 | 10/2011 | Barenholz et al. | |
| 2011/0250264 A1 | 10/2011 | Schutt et al. | |
| 2013/0177633 A1 | 7/2013 | Schutt et al. | |
| 2013/0177634 A1 | 7/2013 | Schutt et al. | |
| 2013/0177637 A1 | 7/2013 | Schutt et al. | |
| 2013/0189350 A1 | 7/2013 | Garcia et al. | |
| 2013/0195965 A1 | 8/2013 | Schutt et al. | |
| 2013/0251786 A1 | 9/2013 | Li | |
| 2013/0306759 A1 | 11/2013 | Schutt et al. | |
| 2014/0004173 A1 | 1/2014 | Hartounian et al. | |
| 2014/0319045 A1 | 10/2014 | Shevitz | |
| 2015/0158907 A1 | 6/2015 | Zhou | |
| 2018/0161275 A1 | 6/2018 | Los et al. | |
| 2019/0169559 A1 | 6/2019 | Coffman | |
| 2019/0314281 A1 | 10/2019 | Ma et al. | |
| 2022/0233442 A1* | 7/2022 | Hall | A61K 9/127 |
| 2022/0233446 A1 | 7/2022 | Hall et al. | |
| 2022/0304932 A1* | 9/2022 | Hall | A61K 9/1277 |
| 2023/0248648 A1 | 8/2023 | Hall et al. | |
| 2023/0301916 A1 | 9/2023 | Hall et al. | |

FOREIGN PATENT DOCUMENTS

| | | |
|---|---|---|
| CA | 2176712 | 5/1995 |
| CA | 1337273 | 10/1995 |
| CA | 2199004 | 5/2000 |
| CN | 110179752 A | 8/2019 |
| CN | 108078929 B | 1/2021 |
| EP | 0 126 580 | 11/1984 |
| EP | 0 208 450 | 1/1987 |
| EP | 0 506 639 | 9/1992 |
| EP | 0 280 503 | 4/1993 |
| EP | 0 752 245 | 1/1997 |
| EP | 3 572 070 | 11/2019 |
| GB | 2050287 | 1/1981 |
| WO | WO 85/03011 | 7/1985 |
| WO | WO 89/00846 | 2/1989 |
| WO | WO 89/04656 | 6/1989 |
| WO | WO 91/14445 | 10/1991 |
| WO | WO 93/00888 | 1/1993 |
| WO | WO 94/08565 | 4/1994 |
| WO | WO 94/08626 | 4/1994 |
| WO | WO 94/22430 | 10/1994 |
| WO | WO 94/23697 | 10/1994 |
| WO | WO 94/26250 | 11/1994 |
| WO | WO 94/26253 | 11/1994 |
| WO | WO 94/27581 | 12/1994 |
| WO | WO 95/01164 | 1/1995 |
| WO | WO 95/13796 | 5/1995 |
| WO | WO 96/08235 | 3/1996 |
| WO | WO 96/14057 | 5/1996 |
| WO | WO 97/02022 | 1/1997 |
| WO | WO 97/03652 | 6/1997 |
| WO | WO 97/35561 | 10/1997 |
| WO | WO 98/014171 | 4/1998 |
| WO | WO 98/033483 | 8/1998 |
| WO | WO 12/109387 | 8/2012 |
| WO | WO 21/11299 | 1/2021 |

OTHER PUBLICATIONS

Opinion in United States District Court, District of New Jersey, Civil Action No. 21-19829-MCA-JRA, dated Aug. 9, 2024, 40 pp.

Order in Civil Action No. 21-19829-MCA-JRA, dated Aug. 9, 2024, 2 pp.

"Guidance for Industry: Guideline on Sterile Drug Products Produced by Aseptic Processing," Jun. 1987, Reprinted Jun. 1991, pp. 1-43, Center for Drug Evaluation and Research et al.

"Local Anesthetics," New Pharmacology, Revised 3.sup.rd ed., pp. 261-266, Tanaka et al. eds. Nankoudou Corp., Aug. 1, 1997.

Andrews et al., "Boundary Layer Solution for a Bubble Rising Through a Liquid Containing Surface-Active Contaminants," Ind. Eng. Chem. Res., 1995, 34(4):1371-1382.

Arroyo et al., "Use of intermittent jets to enhance flux in crossflow filtration," J. Membrane Sci., 1993, 80:117-129.

Assil et al., "Liposome Suppression of Proliferative Vitreoretinopathy: Rabbit Model Using Antimetabolite Encapsulated Liposomes," Invest. Ophthalmol. Vis. Sci., 32(11):2891-2897, 1991.

Assil et al., "Multivesicular Liposomes: Sustained Release of the Antimetabolite Cytarabine in the Eye," Arch Ophthalmol., 1987, 105(3):400-403.

Assil et al., "Tobramycin Liposomes: Single Subconjunctival Therapy of Pseudomonal Keratitis," Invest. Ophthalmol. Vis. Sci., 32(13):3216-3220, 1991.

Bangham et al., "Diffusion of Univalent Ions Across the Lamellae of Swollen Phospholipids," J. Mol. Biol., 1965, 13:238-252.

Barbet et al., "Weak acid-induced release of liposome-encapsulated carboxyfluorescein," Biochim. Biophys. Acta, 1984, 772:347-356.

Bhave, "Cross-Flow Filtration," Fermentation and Biochemical Engineering Handbook: Principles, Process Design and Equipment, 2.sup.nd edition, (Vogel et al. Eds., 1997), Noyes Publications, Westwood, New Jersey, pp. 271-278.

Bonetti et al., "An extended-release formulation of methotrexate for subcutaneous administration," Cancer Chemother. Pharmacol., 33:303-306, 1994.

Boogaerts et al. "Biodistribution of liposome-associated bupivacaine after extradural administration to rabbits," Br. J. Anaesth, 1995, 75:319-325.

Boogaerts et al. "Epidural Administration of Liposome-Associated Bupivacaine for the Management of Postsurgical Pain: A First Study," J. Clin. Anesth, 1994, 6:315-320.

Boogaerts et al. "Motor Blockade and Absence of Local Nerve Toxicity Induced by Liposomal Bupivacaine Injected into the Axillary Plexus of Rabbits," Acta Anesth. Belg., 1995, 46:19-24.

Boogaerts et al. "Plasma concentrations of bupivacaine after brachial plexus administration of liposome-associated and plain solutions to rabbits," Can. J. Anaesth, 1993, 40:1201-1204.

Boogaerts et al. "Toxicity of Bupivacaine Encapsulated into Liposomes and Injected Intravenously: Comparison with Plan Solutions," Anesth. Analg., 1993, 76:553-555.

Chamberlain et al., "Treatment of Leptomeningeal Metastasis With Intraventricular Administration of Depot Cytarabine (DTC 101): A Phase I Study," Arch. Neurol., 50:261-264, 1993.

Chatelut et al., "A slow-release methotrexate formulation for intrathecal chemotherapy," Cancer Chemother. Pharmacol., 32:179-182, 1993.

Chattopadhyay et al., "The Protective Effect of Specific Medium Additives with Respect to Bubble Rupture," Biotechnol. Bioeng., 1995, 45(6):473-480.

(56) References Cited

OTHER PUBLICATIONS

Chemical Comprehensive Dictionary, compact 2.sup.rd ed., Kyoritsushuppan Corp., edited by the Editorial Committee of the Chemical Comprehensive Dictionary, Aug. 25, 1963, pp. 725-726.
Cherry et al., "Cell Death in the Thin Films of Bursting Bubbles," Biotechnol. Prog., 1992, 8(1):11-18.
Cullis et al., "Structural Properties and Functional Roles of Phospholipids in Biological Membranes," Phospholipids and Cellular Regulation, pp. 1-59, vol. 1, J.F. Kuo ed., CRC Press, 1985, Boca Raton, FL.
Davidson et al., 2010, High-dose bupivacaine remotely loaded into multivesicular liposomes demonstrates slow drug release without systemic toxic plasma concentrations after subcutaneous administration in humans, Anesthesia & Analgesia, 110(4):1018-1023.
De Gier, J et al., Lipid Composition and Permeability of Liposomes, Biochim. Biophys. Acta 150:666-675 (1968).
Edwards et al., "Large Porous Particles for Pulmonary Drug Delivery," Science, 1997, 276: 1868-1871.
Frucht-Perry et al., "Fibrin-Enmeshed Tobramycin Liposomes: Single Application Topical Therapy of Pseudomonas Keratitis," Cornea, 1992, 11(5):393-397.
Genovesi, "Several uses for tangential-flow filtration in the pharmaceutical industry," J. Parenter. Sci. Technol. (1983), 37(3):81-86.
Grit et al., 1993, Chemical stability of liposomes: implications for their physical stability, Chemistry and Physics of Lipids, 64:3-18.
Grit et al., Apr. 1993, Hydrolysis of saturated soybean phosphatidylcholine in aqueous liposome dispersions, Journal of Pharmaceutical Sciences, 82(4):362-366.
Gruner et al., "Novel Multilayered Lipid Vesicles: Comparison of Physical Characteristics of Multilamellar Liposomes and Stable Plurilamellar Vesicles," Biochemistry, 1985, 24(12):2833-2842.
Holdich et al., "The variation of crossflow filtration rate with wall shear stress and the effect of deposit thickness," Chemical Engineering Research and Design (Trans IChem), 1995, 73(part A):20-26.
Huang, "Studies on Phosphatidylcholine Vesicles. Formation and Physical Characteristics," Biochemistry, 1969, 8(1):344-352.
Huang, et al., "Determination of phospholipid and fatty glyceride in liposome by RP-HPLC with capacitively coupled contactless conductivity detector," Analytical Methods, 2018, 10, 4978-4984.
Ishii, "Production and size control of large unilamellar liposomes by emulsification," Liposome Technology 2.sup.nd Edition, pp. 111-121, vol. 1, Gregory Gregoriadis ed., CRC Press, 1993, Boca Raton, FL.
Jaffrin et al., "Energy saving pulsatile mode cross flow filtration," J. Membrane Sci., 1994, 86:281-290.
Johnson et al., "New nozzle improves FCC feed atomization, unit yield patterns," Oil and Gas Journal, 1994, 92(3):80-86.
Joshi et al., "The safety of liposome bupivacaine following various routes of administration in animals" *J. Pain. Res.*, 8, 781-789 (2015).
Kawashima et al., "Shear-Induced Phase Inversion and Size Control of Water/Oil/Water Emulsion Droplets with Porous Membrane," J. Colloid Interface Sci., 1991, 145(2):512-523.
Kim et al., 1981, Preparation of cell-size unilamellar liposomes with high captured vol. and defined size distribution, Biochim. Biophys. Acta, 646:1-9.
Kim et al., 1983, Preparation of Multivesicular Liposomes, Biochim. Biophys. Acta, 728(3):339-348.
Kim et al., 1985, Preparation of multilamellar vesicles of defined size-distribution by solvent-spherule evaporation, Biochim. Biophys. Acta, 812:793-801.
Kim et al., 1987, Modulation of the peritoneal clearance of liposomal cytosine arabinoside by blank liposomes, Cancer Chemother. Pharmacol., 19(4):307-310.
Kim et al., 1987, Multivesicular Liposomes Containing 1-beta-D-Arabinofuranosylcytosine for Slow-Release Intrathecal Therapy, Cancer Res., 47(15):3935-3937.

Kim et al., 1987, Multivesicular Liposomes Containing Cytarabine Entrapped in the Presence of Hydrochloric Acid for Intracavitary Chemotherapy, Cancer Treat. Rep., 71(7-8):705-711.
Kim et al., 1987, Multivesicular Liposomes Containing Cytarabine for Slow-Release Sc Administration, Cancer Treat. Rep., 71(5):447-450.
Kim et al., 1990, Direct Cerebrospinal Fluid Delivery of an Antiretroviral Agent Using Multivesicular Liposomes, J. Infect. Dis., 162(3):750-752.
Kim et al., 1993, Extended CSF Cytarabine Exposure Following Intrathecal Administration of DTC 101, J. Olin. Oncol., 11(11):2186-2193.
Kim et al., 1993, Extended-release formulation of morphine for subcutaneous administration, Cancer Chemother. Pharmacol., 33(3):187-190.
Kim et al., 1993, Prolongation of Drug Exposure in Cerebrospinal Fluid by Encapsulation into DepoFoam, Cancer Res., 53(7):1596-1598.
Kim, 1993, Liposomes as Carriers of Cancer Chemotherapy: Current status and Future Prospects, Drugs, 46(4):618-638, 1993.
Lafont et al. "Use of Liposome-Associated Bupivacaine for the Management of a Chronic Pain Syndrome," Anesth. Analg., 1994, 79:818.
Lafont et al. "Use of Liposome-Associated Bupivacaine in a Cancer Pain Syndrome," Anaesthesia, 1996, 51:578-579.
Legros et al. "Influence of Different Liposomal Formulations on the Pharmacokinetics of Encapsulated Bupivacaine," [Abstract]. Anesthesiology, 1990, 73: A851.
Liposome Drug Products. Chemistry, Manufacturing, and Controls; Human Pharmacokinetics and Bioavailability; and Labeling Documentation. Guidance for Industry, U.S. Department of Health and Human Services, Food and Drug Administration, Center for Drug Evaluation and Research (CDER), Apr. 2018.
Maa et al., "Liquid-liquid emulsification by rotor/stator homogenization," J. Controlled Release, 1996, 38:219-228.
Maestre et al., "Contribution of Light Scattering to the Circular Dichroism of Deoxyribonucleic Acid Films, Deoxyribonucleic Acid-Polylysine Complexes, and Deoxyribonucleic Acid Particles in Ethanolic Buffers," Biochemistry, 1980, 19(23):5214-5223.
Malinovsky et al., "Neurotoxilogical Assessment After Intracisternal Injection of Liposomal Bupivacaine in Rabbits," Anesth. Analg., 1997, 85:1331-1336.
Mancini, "Mastering the mix: Why Leave Mixing to Chance? Get a Proper Mix and a Better Product Every Time," Food Engineering, Mar. 1996, pp. 79-83.
Maranges et al., "Crossflow Filtration of Saccharomyces cerevisiae Using an Unsteady Jet," Biotechnol. Tech., 1995, 9(9): 649-654.
Mashimo et al. "Prolongation of Canine Epidural Anesthesia by Liposome Encapsulation of Lidocaine," Anesth. Analg., 1992, 74:827-834.
Matsumoto et al., "An Attempt at Preparing Water-in-Oil-in-Water Multiple-Phase Emulsions," J. Colloid Interface Sci., 1976, 57(2):353-361.
Meissner et al., Application of High Frequency Backpulsing in Diafiltration of Multivesicular Liposomes, North American Membrane Society, Proceedings, 9.sup.th Annual Meeting, May 31-Jun. 4, 1997, Baltimore, MD, (1997). Abstract.
Meissner et al., Application of Unsteady Flow Patterns in Permeate and Retentate for the Diafiltration of Multivesicular Lipid Based Particles, Annual AIChE Meeting, Nov. 16-21, 1997, Los Angeles, CA. Unpublished conference paper (1997). Linda Hall Library, Kansas.
Michaels et al., "Sparging and Agitation-Induced Injury of Cultured Animal Cells: Do Cell-to-Bubble Interactions in the Bulk Liquid Injure Cells?" Biotechnol. Bioeng., 1996, 51(4):399-409.
Mutsakis et al., "Advances in Static Mixing Technology," Chem. Eng. Prog, Jul. 1986, pp. 42-48.
Narhi et al., "Role of Native Disulfide Bonds in the Structure and Activity of Insulin-like Growth Factor 1: Genetic Models of Protein-Folding Intermediates," Biochemistry, 1993, 32(19):5214-5221.
Pacira Pharmaceuticals Inc., 2018, Exparel prescribing information, 28 pp.

(56) References Cited

OTHER PUBLICATIONS

Paul, "Reaction Systems for Bulk Pharmaceutical Production," Chem. Ind., May 21, 1990, pp. 320-325.
Quirk et al., "Investigation of the parameters affecting the separation of bacterial enzymes from cell debris by tangential flow filtration," Enzyme Microb. Technol. (1984), 6(5):201-206.
Radlett, "The Concentration of Mammalian Cells in a Tangential Flow Filtration Unit," J. Appl. Chem. Biotechnol. (1972), 22:495-499.
Redkar et al., "Cross-Flow Microfiltration with High-Frequency Reverse Filtration," AIChE Journal, 1995, 41(3):501-508.
Richard et al., 2011, The safety and tolerability evaluation of DepoFoam, bupivacaine (bupivacaine extended-release liposome injection) administered by incision would infiltration in rabbits and dogs, Expert Opinion on Investigational Drugs, 20(10):1327-1341.
Ripperger, et al., "Crossflow microfiltration—state of the art," Separation and Purification Technology, 26 (2002), 19-31.
Rodgers et al., "Reduction of Membrane Fouling in the Ultrafiltration of Binary Protein Mixtures," AIChE Journal, 1991, 37(10):1517-1528.
Roy et al., "Multivesicular liposomes containing bleomycin for subcutaneous administration," Cancer Chemother. Pharmacol., 28(2):105-108, 1991.
Russack et al., "Quantitative Cerebrospinal Fluid Cytology in Patients Receiving Intracavitary Chemotherapy," Ann. Neurol., 1993, 34(1):108-112.
Saberi et al., "Bubble Size and Velocity Measurement in Gas-Liquid Systems: Application of Fiber Optic Technique to Pilot Plant Scale," Can. J. Chem. Eng., 1995, 73: 253-257.
Shakiba et al., "Evaluation of Retinal Toxicity and Liposome Encapsulation of the Anti-CMV drug 2'-nor-cyclic GMP," Invest. Ophthalmol. Vis. Sci., 34(10):2903-2910, 1993.
Skuta et al., "Filtering Surgery in Owl Monkeys Treated with the Antimetabolite 5-Fluorouridine 5' Monophosphate Entrapped in Multivesicular Liposomes," Am. J. Ophthmalmol., 1987, 103(5):714-716.
Streiff et al., "Don't overlook static-mixer reactors," Chem. Eng., Jun. 1994, pp. 76-82.
Szoka et al., "Comparative properties and methods of preparation of lipid vesicles (liposomes)," Ann. Rev. Biophys. Bioeng., 1980, 9:467-508.
Tanaka et al., "Crossflow Filtration of Baker's Yeast with Periodical Stopping of Permeation Flow and Bubbling," Biotechnol. Bioeng., 1995, 47(3):401-404.
Thompson, G.A. Jr., The Regulation of Membrane Lipid Metabolism 2.sup.nd Ed., CRC Press: Boca Raton, pp. 1-20 (1992).
Tsuchiya et al., "Tortuosity of Bubble Rise Path in a Liquid-Solid Fluidized Bed: Effect of Particle Shape," AIChE Journal, 1995, 41(6):1368-1374.
Turski et al., "Magnetic Resonance Imaging of Rabbit Brain after Intracarotid Injection of Large Multivesicular Liposomes Containing Paramagnetic Metals and DTPA," Magn. Reson. Med., 7(2):184-196, 1998.
Watts et al., "Microencapsulation Using Emulsification/Solvent Evaporation: An Overview of Techniques and Applications," Critical Reviews in Therapeutic Drug Carrier Systems, 1990, 7(3):235-259.
Zheng et al., "FDA Bioequivalence Standards, Chapter 11, Bioequivalence for Liposomal Drug Products," AAPS Advances in the Pharmaceutical Sciences, vol. 13, 2014, 275-296.
Sep. 30, 2021 Redacted letter regarding bupivacaine liposome injectable suspension ANDA No. 214348, Paragraph IV Notice Letter Invalidity contentions for U.S. Pat. No. 11,033,495.
Dec. 28, 2021 Redacted letter regarding bupivacaine liposome injectable suspension ANDA No. 214348, Paragraph IV Notice Letter Invalidity contentions for U.S. Pat. No. 11,179,336.
Apr. 14, 2023 Redacted letter regarding bupivacaine liposome injectable suspension ANDA No. 214348, Paragraph IV Notice Letter invalidity contentions for U.S. Pat. Nos. 11,278,494; 11,311,486; 11,304,904; 11,357,727; 11,426,348; and 11,452,691 (211 pp).
Mar. 11, 2024 Redacted letter regarding bupivacaine liposome injectable suspension ANDA No. 214348 Notice of Paragraph IV certification and invalidity contentions for U.S. Pat. Nos. 11,819,574 and 11,819,575 (57 pp).
May 24, 2024 Redacted letter regarding bupivacaine liposome injectable suspension ANDA No. 214348 Notice of Paragraph IV certification and invalidity contentions for U.S. Pat. No. 11,925,706 (30 pp).
Chahar et al., 2012, Liposomal bupivacaine: a review of a new bupivacaine formulation, Journal of Pain Research, 5:257-264.
National Institute of Drug Abuse, Jun. 2021, Prescription Opioids Drug Facts, 9 pp.
Rabin, Apr. 6, 2018, FDA in brief: FDA approves new use of Exparel for nerve block pain relief following shoulder surgeries, Media Inquiries, 3 pp.
Pacira Pharmaceuticals, Inc. Mar. 22, 2021, Pacira announces FDA approval of supplemental new drug allocation for Exparel® (bupivacaine liposome injectable suspension) in pediatric patients, press release, 4 pp.
Malik et al., 22017, Emerging roles of liposomal bupivacaine in anesthesia practice, Journal of Anaesthesiology Clinical Pharmacology, 33:151-156.
Salehi et al., 2020, Multivesicular liposome (Depofoam) in human disease, Iranian Journal of Pharmaceutical Research, 19(2):9-21.
Lee et al., Mar. 19, 2015, Modernizing pharmaceutical manufacturing: from batch to continuous productions, J. Pharm. Innov. DOI 10.1007/s12247-015-9215-8, 11 pp.
Process Facilities Group, LLC Novo Nordisk Buildings 1 & 9 New Process (archived webpage) retrieved on Sep. 20, 2022, 4 pp.
Pacira BioSciences, Inc., Aug. 2, 2017, Pacira Pharmaceuticals (PCRX) Q2 2017 results—earnings call transcript, 21 pp.
Pacira BioSciences, Inc., Aug. 2, 2018, Pacira Pharmaceuticals (PCRX) Q2 2018 results—earnings call transcript, 24 pp.
Pacira BioSciences, Inc., Aug. 8, 2019, Pacira Pharmaceuticals (PCRX) Q2 2019 results—earnings call transcript, 21 pp.
Pacira BioSciences, Inc., 2022, Non-opioid Exparel reduces the need for opioids, project brochure, https://www.exparel.com/patients/non-opioid-pain-medication, downloaded Oct. 27, 2022, 4 pp.
Pacira Pharmaceuticals, Inc., at Jefferies Global Healthcare Conference, Jun. 3, 2013, FD (Fair Disclosure) Wire, 8 pp.
US Dept. Health and Human Services, Food and Drug Administration, Jan. 2011, Guidance for Industry, Process Validation: general Principles and Practices, 23 pp.
Pacira Pharmaceuticals, Inc., Oct. 25, 2022, Pacira Pharmaceuticals, Inc., announces commercial availability of Exparel® News Release, 7 pp.
Pacira BioSciences, Inc., Jan. 7, 2021, Pacira reports record revenue for 2020 of $429.6 million, press release, 3 pp.
Pacira BioSciences, Inc., Feb. 28, 2019, Pacira reports record fourth quarter and full year revenues, press release, 8 pp.
Department of Health and Human Services, Food and Drug Administration, Feb. 2012, Patent & Exclusivity Drug Product List, Cumulative Supplement 2, 3 pp.
Department of Health and Human Services, Food and Drug Administration, Jun. 2012, Patent & Exclusivity Drug Product List, Cumulative Supplement 6, 3 pp.
Department of Health and Human Services, Food and Drug Administration, Oct. 2014, Patent & Exclusivity Drug Product List, Cumulative Supplement 10, 3 pp.
Department of Health and Human Services, Food and Drug Administration, Dec. 2015, Patent & Exclusivity Drug Product List, Cumulative Supplement 12, 3 pp.
Department of Health and Human Services, Food and Drug Administration, Mar. 2017, Patent & Exclusivity Drug Product List, Cumulative Supplement 3, 3 pp.
Department of Health and Human Services, Food and Drug Administration, Jul. 2021, Patent & Exclusivity Drug Product List, Cumulative Supplement 7, 3 pp.
Department of Health and Human Services, Food and Drug Administration, Nov. 2021, Patent & Exclusivity Drug Product List, Cumulative Supplement 11, 3 pp.

(56) References Cited

OTHER PUBLICATIONS

Crommelin et al., Hydrolysis of phospholipids in liposomes and stability-indicating analytical techniques, in Gregoriadis, ed., Liposome Technology, 2007 (Third Edition) CRC Press, Boca Raton, FL, pp. 285-295.

European Medicines Agency, Committee for Medicinal Products for Human Use, Sep. 17, 2020, Assessment report: Exparel liposomal, 147 pp.

Ilfeld, Liposomal bupivacaine: its role in regional anesthesia and postoperative analgesia, Advances in Anesthesia, 2014, 32:133-147.

Kharitonov, A review of the compatibility of liposome bupivacaine with other drug products and commonly used implant materials, Postgraduate Medicine, 2014, 126(1):129-138.

Li et al., Multivesicular liposomes for the sustained release of angiotensin I-converting enzyme (ACE) inhibitory peptides from peanuts: design, characterization, and in vitro evaluation, Molecules, 2019, 24:1746, 15 pp.

Aug. 2, 2017, Pacira Pharmaceuticals (PCRX) Q2 2017 Results—Earnings Call Transcript, https://seekingalpha.com/article/4093713-pacira-pharmaceuticals-pcrx-g2-2017-results-earningscall-transcript; accessed on Apr. 17, 2023, 24 pp.

Pacira Pharmaceuticals, Inc., U.S. Securities and Exchange Commission, Form 10-K, for fiscal year ended Dec. 31, 2018, 102 pp.

Wang et al., Multivesicular liposome (MVL) sustained delivery of a n ovel synthetic cationic GnRH antagonist for prostate cancer treatment, Journal of Pharmacy and Pharmacology, 2011, 63:904-910.

Yadav et al., Stability aspects of liposomes, Indian Journal of Pharmaceutical Education and Research, 2011, 45(4):402-413.

Yu et al., 2023, Characterization of Exparel bupivacaine multivesicular liposomes, International Journal of Pharmaceutics, 639:122952, 6 pp.

Bulbake et al., 2017, Liposomal Formulations in Clinical Use: An Updated Review, Pharmaceutics, 9(12):1-33.

Lu et al., 2001, Preparation and characterization of bupivacaine multivesicular liposome: A QbD study about the effects of formulation and process on critical quality attributes, International Journal of Pharmaceutics, 598:120335.

Manna et al., 2019, Proving the mechanism of bupivacaine drug release from multivesicular liposomes, Journal of Controlled Release, 294:279-287.

Mayat et al., Jun. 30, 1973, The Use of Marcaine for Epidural Anaesthesia, S. Afr. Med. J., 47:1112-1114.

Mayne et al., 2019, Towards experimental P-systems using multivesicular liposomes, Journal of Membrane Computing, 1:20-28.

Physician's Desk Reference, 2013, Julie Cross ed., 67th ed., Exparel, pp. 311, 2128-2131.

U.S. Department of Health and Human Services., Office of Generic Drug Policy, 2020, excerpt from Approved Drug Products with Therapeutic Equivalence Evaluations at ADA 34 (40th Ed. 2020), 7 pp.

U.S. Food & Drug Admin., Nov. 2003, Guidance for Industry, Q1A(R2) Stability Testing of New Drug Substances and Products, 25 pp.

Ye et al., 2000, DepoFoam™ technology: a vehicle for controlled delivery of protein and peptide drugs, Journal of Controlled Release, 64:155-166.

Zhang et al., 2000, Effect of pH, Ionic Strength and Oxygen Burden on the Chemical Stability of EPC/Cholesterol Liposomes Under Accelerated Conditions Part 1: Lipid Hydrolysis, Eur. J of Pharmaceutics and Biopharmaceutics, 50:357-364.

\* cited by examiner

F = 0.2 μm sterilizing filter; P = Pressure gauge; T = Temperature probe; Q = Flow meter;

FIG. 5A. 5°C IVRA data for batches produced by the 45 L process

| Batch No. | Mfr. Date | 5C in Vitro % Release of Bupivacaine ||||||||||
| | | 24h (0 m) | 24h (3 m) | 24h (6 m) | 24h (9 m) | 24h (12 m) | 48h (0 m) | 48h (3 m) | 48h (6 m) | 48h (9 m) | 48h (12 m) |
|---|---|---|---|---|---|---|---|---|---|---|---|
| A1  | 10-Mar-10 | 65 | 66 | 61 | 65 | 60 | 79 | 80 | 84 | 80 | 76 |
| A2  | 8-Apr-12  | 60 | 58 | 56 | 55 | 53 | 77 | 76 | 74 | 74 | 72 |
| A3  | 13-Apr-12 | 59 | 64 | 61 | 61 | 58 | 78 | 79 | 79 | 78 | 76 |
| A4  | 29-Feb-12 | 64 | 65 | 55 | 62 | 59 | 84 | 74 | 70 | 75 | 72 |
| A5  | 4-Mar-12  | 65 | 62 | 57 | 64 | 59 | 84 | 72 | 69 | 75 | 74 |
| A6  | 7-Mar-12  | 63 | 62 | 62 | 66 | 67 | 77 | 79 | 76 | 79 | 80 |
| A7  | 11-Mar-12 | 62 | 65 | 62 | 65 | 62 | 81 | 80 | 76 | 80 | 77 |
| A8  | 20-Mar-12 | 63 | 60 | 59 | 62 | 55 | 79 | 71 | 77 | 78 | 74 |
| A9  | 6-Jul-12  | 64 | 58 | 61 | 59 | 64 | 76 | 80 | 78 | 75 | 79 |
| A10 | 2-Sep-13  | 60 | 58 | 62 | 57 | 61 | 78 | 77 | 81 | 75 | 75 |
| A11 | 11-Jul-13 | 62 | 58 | 58 | 51 | 53 | 80 | 76 | 75 | 70 | 74 |
| A12 | 13-Jul-13 | 66 | 62 | 62 | 57 | 57 | 83 | 78 | 83 | 78 | 80 |
| A13 | 15-Jul-13 | 65 | 63 | 63 | 49 | 58 | 85 | 78 | 82 | 75 | 81 |
| A14 | 14-Mar-14 | 62 | 58 | 57 | 58 | 58 | 77 | 75 | 72 | 74 | 72 |
| A15 | 18-Feb-14 | 64 | 50 | 51 | 57 | 59 | 79 | 73 | 71 | 74 | 74 |
| A16 | 22-Feb-14 | 63 | 54 | 52 | 52 | 48 | 80 | 72 | 69 | 73 | 68 |
| A17 | 23-Feb-14 | 62 | 48 | 56 | 57 | 51 | 79 | 67 | 69 | 73 | 74 |
| A18 | 25-Mar-14 | 62 | 57 | 50 | 54 | 54 | 75 | 70 | 70 | 70 | 72 |
| A19 | 31-Mar-14 | 59 | 54 | 56 | 55 | 55 | 74 | 73 | 73 | 73 | 73 |
| A20 | 2-Apr-14  | 63 | 60 | 61 | 61 | 60 | 78 | 76 | 76 | 77 | 78 |
| A21 | 8-Apr-14  | 64 | 59 | 58 | 62 | 61 | 77 | 74 | 77 | 79 | 77 |
| A22 | 26-Apr-14 | 58 | 62 | 60 | 63 | 62 | 74 | 80 | 78 | 78 | 79 |
| A23 | 29-Oct-14 | 56 | 58 | 56 | 57 | 55 | 72 | 76 | 77 | 74 | 76 |
| A24 | 31-Oct-14 | 55 | 57 | 59 | 54 | 55 | 73 | 73 | 78 | 75 | 75 |
| A25 | 5-Nov-14  | 57 | 59 | 58 | 57 | 61 | 77 | 77 | 76 | 76 | 76 |
| A26 | 23-Nov-14 | 59 | 56 | 55 | 54 | 50 | 73 | 70 | 75 | 69 | 68 |

FIG. 5B. 5°C IVRA data for batches produced by the 45 L process

| Batch No. | Mfr. Date | 5C in Vitro % Release of Bupivacaine ||||||||||
| | | 24h (0 m) | 24h (3 m) | 24h (6 m) | 24h (9 m) | 24h (12 m) | 48h (0 m) | 48h (3 m) | 48h (6 m) | 48h (9 m) | 48h (12 m) |
|---|---|---|---|---|---|---|---|---|---|---|---|
| A27 | 1-Dec-14 | 55 | 56 | 52 | 52 | 47 | 70 | 70 | 68 | 68 | 65 |
| A28 | 22-Feb-15 | 70 | 69 | 65 | 64 | 64 | 85 | 84 | 83 | 80 | 81 |
| A29 | 22-Feb-15 | 55 | 50 | 52 | 47 | 46 | 68 | 64 | 64 | 62 | 61 |
| A30 | 22-Feb-15 | 53 | 48 | 53 | 50 | 47 | 67 | 69 | 67 | 54 | 66 |
| A31 | 29-Oct-15 | 80 | 68 | 64 | 60 | 59 | 86 | 84 | 79 | 77 | 76 |
| A32 | 3-Nov-15 | 76 | 65 | 61 | 55 | 57 | 85 | 79 | 77 | 74 | 74 |
| A33 | 5-Nov-15 | 73 | 63 | 57 | 51 | 55 | 84 | 79 | 74 | 70 | 72 |
| A34 | 10-Nov-15 | 78 | 64 | 62 | 57 | 58 | 82 | 77 | 77 | 75 | 75 |
| A35 | 8-Jun-16 | 54 | 55 | 61 | 52 | 52 | 71 | 75 | 76 | 71 | 70 |
| A36 | 8-Jun-16 | 59 | 55 | 58 | 50 | 53 | 79 | 74 | 73 | 68 | 70 |
| A37 | 9-Jun-16 | 60 | 54 | 60 | 51 | 54 | 77 | 72 | 74 | 68 | 70 |
| A38 | 15-Jun-16 | 63 | 54 | 56 | 53 | 57 | 81 | 75 | 74 | 70 | 75 |
| A39 | 30-Apr-16 | 60 | NA | 54 | 58 | 59 | 79 | NA | 73 | 75 | 77 |
| A40 | 29-Apr-16 | 64 | NA | 51 | 55 | 58 | 79 | NA | 69 | 76 | 77 |
| A41 | 30-Apr-16 | 61 | NA | 52 | 53 | 57 | 77 | NA | 70 | 74 | 75 |
| A42 | 1-May-16 | 57 | NA | 47 | 49 | 52 | 77 | NA | 66 | 70 | 72 |
| A43 | 3-May-16 | 64 | 55 | 51 | 57 | 64 | 86 | 73 | 72 | 77 | 84 |
| A44 | 4-May-16 | 60 | 55 | 57 | 57 | 53 | 80 | 75 | 73 | 78 | 72 |
| A45 | 6-May-16 | 62 | 58 | 59 | 58 | 58 | 82 | 78 | 75 | 79 | 73 |
| A46 | 7-May-16 | 60 | 58 | 59 | 60 | 59 | 79 | 75 | 79 | 84 | 75 |
| A47 | 8-May-16 | 60 | 58 | 57 | 61 | 58 | 80 | 75 | 75 | 82 | 77 |
| A48 | 10-May-16 | 58 | 53 | 53 | 58 | 52 | 81 | 70 | 71 | 76 | 69 |
| A49 | 9-Aug-18 | 62 | 58 | 56 | 58 | 57 | 79 | 73 | 74 | 78 | 73 |
| A50 | 8-Aug-18 | 60 | 54 | 52 | 57 | 56 | 74 | 71 | 70 | 72 | 71 |
| A51 | 15-Nov-16 | 56 | 55 | 55 | 53 | 55 | 74 | 71 | 73 | 73 | 72 |
| A52 | 15-Nov-16 | 69 | 65 | 66 | 63 | 65 | 84 | 81 | 82 | 82 | 79 |

FIG. 5C. 5°C IVRA data for batches produced by the 45 L process

| Batch No. | Mfr. Date | 5C in Vitro % Release of Bupivacaine | | | | | | | | | | |
|---|---|---|---|---|---|---|---|---|---|---|---|---|
| | | 24h (0 m) | 24h (3 m) | 24h (6 m) | 24h (9 m) | 24h (12 m) | 48h (0 m) | 48h (3 m) | 48h (6 m) | 48h (9 m) | 48h (12 m) |
| A53 | 16-Nov-16 | 55 | 51 | 54 | 52 | 49 | 69 | 65 | 67 | 68 | 66 |
| A54 | 18-Nov-16 | 57 | 54 | 57 | 55 | 54 | 75 | 74 | 73 | 72 | 73 |
| A55 | 19-Dec-16 | 69 | 61 | 59 | 62 | 57 | 88 | 77 | 74 | 76 | 74 |
| A56 | 21-Dec-16 | 70 | 62 | 60 | 62 | 57 | 87 | 74 | 76 | 75 | 76 |
| A57 | 27-Dec-16 | 67 | 69 | 64 | 62 | 65 | 84 | 80 | 80 | 79 | 80 |
| A58 | 28-Dec-16 | 55 | 54 | 48 | 50 | 54 | 75 | 65 | 65 | 66 | 70 |
| A59 | 29-Dec-16 | 61 | 60 | 57 | 58 | 59 | 80 | 72 | 74 | 71 | 73 |
| A60 | 29-Dec-16 | 62 | 61 | 55 | 55 | 60 | 81 | 70 | 72 | 73 | 76 |
| A61 | 18-Mar-16 | 53 | 53 | 45 | 45 | 47 | 75 | 70 | 64 | 64 | 64 |
| A62 | 20-Mar-16 | 53 | 51 | 47 | 47 | 46 | 70 | 65 | 64 | 64 | 63 |
| A63 | 14-Dec-16 | 62 | 56 | 59 | 53 | 58 | 75 | 73 | 71 | 83 | 74 |
| A64 | 9-Feb-17 | 51 | 52 | 54 | 52 | 54 | 71 | 68 | 67 | 70 | 68 |
| A65 | 9-Feb-17 | 59 | 59 | 58 | 55 | 58 | 78 | 73 | 74 | 75 | 75 |
| A66 | 23-Feb-17 | 67 | 70 | 69 | NA | 64 | 85 | 82 | 85 | NA | 83 |
| A67 | 12-May-17 | 64 | 60 | 60 | 59 | 57 | 80 | 75 | 74 | 74 | 76 |
| A68 | 13-May-17 | 64 | 58 | 60 | 60 | 59 | 79 | 77 | 77 | 74 | 81 |
| A69 | 3-Jul-17 | 61 | 62 | 60 | 59 | 59 | 80 | 78 | 75 | 78 | 77 |
| A70 | 4-Jul-17 | 62 | 63 | 60 | 60 | 58 | 79 | 77 | 76 | 79 | 75 |
| A71 | 4-Jul-17 | 64 | 62 | 62 | 61 | 61 | 81 | 80 | 77 | 77 | 77 |
| A72 | 15-Aug-17 | 62 | 61 | 58 | 56 | 59 | 79 | 77 | 75 | 79 | 76 |
| A73 | 14-Aug-17 | 61 | 59 | 57 | 56 | 57 | 76 | 75 | 74 | 78 | 75 |
| A74 | 20-Nov-17 | 63 | 60 | 60 | 62 | 64 | 81 | 76 | 76 | 77 | 80 |
| A75 | 21-Nov-17 | 62 | 60 | 61 | 62 | 63 | 81 | 77 | 77 | 77 | 81 |
| A76 | 13-Apr-17 | 60 | 55 | 54 | 57 | 57 | 76 | 72 | 69 | 72 | 69 |
| A77 | 19-Apr-17 | 59 | 57 | 51 | 55 | 56 | 76 | 71 | 68 | 72 | 67 |
| A78 | 21-Apr-17 | 60 | 56 | 54 | 56 | 54 | 77 | 72 | 69 | 70 | 68 |

FIG. 5D. 5°C IVRA data for batches produced by the 45 L process

| Batch No. | Mfr. Date | 5C in Vitro % Release of Bupivacaine ||||||||||
| | | 24h (0 m) | 24h (3 m) | 24h (6 m) | 24h (9 m) | 24h (12 m) | 48h (0 m) | 48h (3 m) | 48h (6 m) | 48h (9 m) | 48h (12 m) |
|---|---|---|---|---|---|---|---|---|---|---|---|
| A79 | 9-May-17 | 61 | 55 | 57 | 54 | 53 | 77 | 71 | 81 | 71 | 70 |
| A80 | 11-May-17 | 62 | 56 | 58 | 56 | 56 | 78 | 73 | 80 | 73 | 70 |
| A81 | 15-May-17 | 63 | 57 | 61 | 56 | 56 | 79 | 72 | 83 | 73 | 70 |
| A82 | 17-May-17 | 66 | 63 | 65 | 55 | 67 | 81 | 75 | 83 | 74 | 77 |
| A83 | 9-Feb-18 | 65 | 54 | 62 | 60 | 61 | 81 | 78 | 78 | 78 | 76 |
| A84 | 10-Feb-18 | 67 | 66 | 64 | 66 | 62 | 84 | 82 | 83 | 84 | 79 |
| A85 | 10-Feb-18 | 62 | 58 | 60 | 59 | 58 | 79 | 79 | 76 | 75 | 76 |
| A86 | 14-Mar-18 | 61 | 60 | 58 | 60 | 56 | 81 | 77 | 74 | 77 | 75 |
| A87 | 14-Mar-18 | 64 | 61 | 60 | 61 | 61 | 84 | 81 | 77 | 79 | 79 |
| A88 | 22-Mar-18 | 61 | 58 | 54 | 57 | 53 | 81 | 75 | 73 | 71 | 68 |
| A89 | 22-Mar-18 | 67 | 65 | 61 | 62 | 65 | 84 | 85 | 81 | 82 | 82 |
| A90 | 3-Jun-18 | 63 | 55 | 57 | 56 | 56 | 78 | 69 | 75 | 67 | 73 |
| A91 | 4-Jun-18 | 59 | 54 | 54 | 53 | 52 | 77 | 69 | 71 | 68 | 71 |
| A92 | 5-Jun-18 | 64 | 54 | 56 | 54 | 54 | 78 | 69 | 72 | 67 | 71 |
| A93 | 23-Jun-18 | 58 | 51 | 53 | 51 | 46 | NA | NA | NA | NA | NA |
| A94 | 24-Jun-18 | 60 | 57 | 53 | 52 | 50 | NA | NA | NA | NA | NA |
| A95 | 25-Jun-18 | 60 | 56 | 52 | 52 | 48 | NA | NA | NA | NA | NA |
| A96 | 22-Jun-18 | 59 | 52 | 46 | 47 | 46 | NA | NA | NA | NA | NA |
| A97 | 23-Jun-18 | 58 | 55 | 49 | 45 | 48 | NA | NA | NA | NA | NA |
| A98 | 24-Jun-18 | 57 | 56 | 49 | 48 | 45 | NA | NA | NA | NA | NA |
| A99 | 29-Jul-18 | 58 | 56 | 53 | 54 | 54 | 74 | 72 | 68 | 69 | 71 |
| A100 | 30-Oct-18 | 59 | 52 | 53 | 53 | 50 | 76 | 71 | 71 | 70 | 68 |
| A101 | 31-Oct-18 | 63 | 52 | 53 | 56 | 49 | 77 | 70 | 72 | 72 | 69 |
| A102 | 30-Oct-18 | 57 | 48 | 47 | 52 | 48 | 73 | 65 | 72 | 67 | 63 |
| A103 | 20-Nov-18 | 67 | 60 | 58 | 57 | 56 | 84 | 78 | 74 | 72 | 70 |
| A104 | 29-Nov-18 | 70 | 61 | 60 | 55 | 57 | 85 | 81 | 79 | 74 | 74 |

FIG. 5E. 5°C IVRA data for batches produced by the 45 L process

| Batch No. | Mfr. Date | 5C in Vitro % Release of Bupivacaine | | | | | | | | |
|---|---|---|---|---|---|---|---|---|---|---|
| | | 24h (0 m) | 24h (3 m) | 24h (6 m) | 24h (9 m) | 24h (12 m) | 48h (0 m) | 48h (3 m) | 48h (6 m) | 48h (9 m) | 48h (12 m) |
| A105 | 11-Dec-18 | 53 | 51 | 51 | 42 | 44 | 72 | 72 | 65 | 62 | 61 |
| A106 | 20-Apr-19 | 65 | 62 | 64 | 61 | 60 | 83 | 82 | 79 | 76 | 77 |
| A107 | 19-Apr-19 | 64 | 62 | 61 | 60 | 58 | 84 | 81 | 79 | 76 | 77 |
| A108 | 28-Apr-19 | 63 | 63 | 60 | 60 | 59 | 78 | 79 | 74 | 75 | 73 |
| A109 | 12-Jul-19 | 63 | 63 | 63 | 61 | 63 | 84 | 80 | 79 | 79 | 78 |
| A110 | 9-Dec-19 | 56 | 52 | 54 | 52 | 56 | 73 | 69 | 65 | 67 | 73 |
| A111 | 9-Dec-19 | 54 | 50 | 50 | 48 | 53 | 71 | 70 | 66 | 66 | 74 |
| A112 | 22-Dec-19 | 58 | 51 | 51 | 45 | 47 | 72 | 68 | 64 | 61 | 69 |
| A113 | 28-Nov-19 | 58 | 55 | 59 | 56 | 53 | 74 | 74 | 71 | 70 | 69 |
| A114 | 28-Nov-19 | 60 | 53 | 55 | 51 | 51 | 78 | 76 | 71 | 72 | 66 |
| A115 | 15-Mar-20 | 58 | 59 | 59 | 53 | 57 | 73 | 70 | 75 | 69 | 74 |
| A116 | 16-Mar-20 | 61 | 60 | 61 | 53 | 61 | 75 | 72 | 77 | 69 | 73 |
| A117 | 22-Mar-20 | 60 | 57 | 58 | 54 | 56 | 77 | 79 | 75 | 71 | 72 |
| A118 | 7-May-20 | 66 | 59 | 58 | 55 | 55 | 82 | 75 | 75 | 71 | 66 |
| A119 | 9-May-20 | 59 | 59 | 57 | 57 | 52 | 77 | 76 | 74 | 71 | 68 |
| A120 | 20-Jun-20 | 60 | 57 | 61 | 59 | 51 | 78 | 76 | 74 | 73 | 68 |
| A121 | 23-Mar-20 | 65 | 61 | 60 | 61 | 58 | 83 | 81 | 80 | 76 | 74 |
| A122 | 5-Oct-20 | 65 | 61 | 54 | 54 | 58 | 80 | 76 | 70 | 71 | 69 |
| A123 | 7-Oct-20 | 64 | 60 | 48 | 51 | 52 | 79 | 74 | 66 | 69 | 65 |
| A124 | 2-Oct-20 | 66 | 61 | 63 | 57 | 57 | 80 | 76 | 76 | 72 | 72 |
| A125 | 11-Jun-21 | 57 | 59 | 53 | 60 | 59 | 73 | 74 | 66 | 74 | 71 |
| A126 | 9-Jun-21 | 57 | 55 | 52 | 56 | 56 | 73 | 72 | 65 | 73 | 70 |
| A127 | 11-Jun-21 | 57 | 57 | 51 | 58 | 56 | 71 | 73 | 64 | 73 | 70 |
| A128 | 21-Jun-21 | 59 | 52 | 57 | 56 | 61 | NA | NA | NA | NA | NA |
| A129 | 22-Jun-21 | 60 | 59 | 59 | 58 | 62 | NA | NA | NA | NA | NA |
| A130 | 14-Jul-21 | 54 | 55 | 56 | 46 | 50 | 70 | 67 | 72 | 64 | 68 |

FIG. 5F. 5°C IVRA data for batches produced by the 45 L process

| Batch No. | Mfr. Date | 5C in Vitro % Release of Bupivacaine ||||||||||
| | | 24h (0 m) | 24h (3 m) | 24h (6 m) | 24h (9 m) | 24h (12 m) | 48h (0 m) | 48h (3 m) | 48h (6 m) | 48h (9 m) | 48h (12 m) |
|---|---|---|---|---|---|---|---|---|---|---|---|
| A131 | 12-Oct-21 | 64 | 64 | 56 | 61 | 61 | 78 | 77 | 71 | 75 | 73 |
| A132 | 11-Oct-21 | 63 | 65 | 59 | 61 | 56 | 78 | 77 | 74 | 76 | 75 |
| A133 | 7-Oct-21 | 62 | 63 | 55 | 53 | 59 | 75 | 78 | 72 | 69 | 75 |
| A134 | 19-May-22 | 55 | 57 | 46 | 51 | 49 | 69 | 69 | 61 | 63 | 60 |
| A135 | 19-May-22 | 60 | 55 | 56 | 55 | 53 | 75 | 70 | 67 | 69 | 65 |
| A136 | 9-Jul-22 | 56 | 59 | 58 | 63 | 58 | 72 | 75 | 74 | 78 | 67 |
| A137 | 16-Jul-22 | 61 | 56 | 64 | 54 | 60 | 75 | 73 | 79 | 68 | 73 |
| A138 | 2-Dec-22 | 66 | 61 | 56 | 69 | 63 | 77 | 74 | 72 | 83 | 79 |
| A139 | 27-Sep-22 | 70 | 65 | 62 | 66 | 70 | 81 | 78 | 80 | 77 | 83 |
| A140 | 23-Oct-22 | 62 | 58 | 55 | 60 | 60 | 73 | 73 | 70 | 71 | 74 |

*NA means "not available"

FIG. 6. 5°C IVRA data for batches produced by the UK 200 L process

| Batch No. | Mfr. Date | 5C in Vitro % Release of Bupivacaine | | | | | | | | |
|---|---|---|---|---|---|---|---|---|---|---|
| | | 24h (0 m) | 24h (3 m) | 24h (6 m) | 24h (9 m) | 24h (12 m) | 48h (0 m) | 48h (3 m) | 48h (6 m) | 48h (9 m) | 48h (12 m) |
| B1 | 16-Mar-20 | 68 | 62 | 65 | 60 | 63 | 83 | 81 | 81 | 77 | 78 |
| B2 | 23-Mar-20 | 60 | 66 | 63 | 60 | 63 | 77 | 82 | 79 | 75 | 75 |
| B3 | 31-Mar-20 | 60 | 66 | 62 | 63 | 59 | 76 | 80 | 80 | 77 | 73 |
| B4 | 29-Jan-21 | 66 | 61 | 62 | 57 | 61 | 80 | 75 | 73 | 70 | 76 |
| B5 | 1-Feb-21 | 62 | 58 | 53 | 57 | 61 | 79 | 71 | 68 | 69 | 74 |
| B6 | 4-Feb-21 | 63 | 60 | 60 | 57 | 62 | 77 | 74 | 74 | 70 | 77 |
| B7 | 26-Jul-21 | 66 | 63 | 65 | 63 | 64 | 81 | 75 | 74 | 76 | 75 |
| B8 | 2-Aug-21 | 63 | 59 | 62 | 62 | 58 | 76 | 72 | 76 | 73 | 72 |
| B9 | 4-Aug-21 | 64 | 62 | 64 | 63 | 62 | 78 | 74 | 77 | 75 | 74 |

FIG. 7. 5°C IVRA data for batches produced by the current process

| Batch No. | Mfr. Date | 5C in Vitro % Release of Bupivacaine | | | | | | | | |
|---|---|---|---|---|---|---|---|---|---|---|
| | | 24h (0 m) | 24h (3 m) | 24h (6 m) | 24h (9 m) | 24h (12 m) | 48h (0 m) | 48h (3 m) | 48h (6 m) | 48h (9 m) | 48h (12 m) |
| 1 | 21-Dec-22 | 68 | 69 | 75 | 75 | 71 | 82 | 84 | 87 | 86 | 85 |
| 2 | 9-Jan-23 | 66 | 67 | 70 | 73 | 70 | 84 | 79 | 83 | 86 | 82 |
| 3 | 11-Jan-23 | 67 | 67 | 69 | 72 | 70 | 82 | 80 | 83 | 85 | 80 |
| 4 | 18-Jan-23 | 66 | 62 | 64 | 65 | 68 | 83 | 76 | 77 | 80 | 79 |
| 5 | 27-Feb-23 | 63 | 67 | 70 | 67 | 65 | 77 | 81 | 83 | 78 | 76 |
| 6 | 1-Nov-22 | 57 | 58 | 60 | NA | 58 | 73 | 71 | 72 | NA | 71 |
| 7 | 16-Dec-22 | 72 | 73 | NA | 78 | 75 | 85 | 86 | NA | 89 | 87 |
| 8 | 5-Jan-23 | 71 | 72 | 77 | NA | 73 | 83 | 86 | 91 | NA | 87 |

*NA means "not available"

MANUFACTURING OF BUPIVACAINE MULTIVESICULAR LIPOSOMES

INCORPORATION BY REFERENCE TO ANY PRIORITY APPLICATION

The present application claims the benefit of priority to U.S. Ser. No. 63/649,872, filed May 20, 2024, which is incorporated by reference.

BACKGROUND

Field

This disclosure relates generally to commercial manufacturing processes for making bupivacaine multivesicular liposomes.

Description of the Related Art

Bupivacaine is a versatile drug that has been shown to be efficacious for a wide variety of indications, including: local infiltration, peripheral nerve block, sympathetic nerve block, and epidural and caudal blocks. It may be used in pre-, intra- and post-operative care settings. Bupivacaine encapsulated multivesicular liposomes (Exparel®) has been approved in the US and Europe for use as postsurgical local analgesia and as an interscalene brachial plexus nerve block to produce postsurgical regional analgesia, providing significant long-lasting pain management across various surgical procedures. Particularly, Exparel® has had great success in the market in part due to the ability to locally administer bupivacaine multivesicular liposomes (MVLs) at the time of surgery and extend the analgesic effects relative to other non-liposomal formulations of bupivacaine. Such extended release properties of bupivacaine MVLs allow patients to control their post-operative pain without or with decreased use of opioids. Given the addictive nature of opioids and the opioid epidemic that has been affecting countries around the world, there is an urgent need for new and improved commercial scale productions of Exparel® to meet the substantial and growing market demand.

SUMMARY

A first aspect of the present disclosure relates to batches comprising compositions of bupivacaine encapsulated multivesicular liposomes (MVLs), the composition comprising:
bupivacaine residing inside a plurality of internal aqueous chambers of MVLs separated by lipid membranes, wherein the lipid membranes comprise 1, 2-dierucoylphosphatidylcholine (DEPC), 1, 2-dipalmitoyl-sn-glycero-3-phospho-rac-(1-glycerol) (DPPG) or a salt thereof, cholesterol, and tricaprylin; and
an aqueous medium in which the bupivacaine encapsulated MVLs are suspended, wherein the aqueous medium also comprises unencapsulated bupivacaine;
the total bupivacaine concentration in the composition is from 12 mg/mL to 17 mg/ml;
wherein the batches are manufactured within a period of six months, and the batches each has a volume of at least 100 liters;
wherein each batch has a cumulative percentage release of bupivacaine from 46% to 71% at a 24-hour time point, measured from two or more aliquots of each batch using a rotator-facilitated in vitro release assay for at least about 48 hours, after storage of the aliquots of each batch at 2° C. to 8° C. for about 12 months from batch manufacture date, and an average rate of change in the cumulative percentage release of bupivacaine of the batches at the 24-hour time point is at least 0.05%/month after storage of the aliquots of each batch at 2° C. to 8° C. for about 12 months;
alternatively or additionally, each batch has a cumulative percentage release of bupivacaine from 60% to 85% at a 48-hour time point, measured from two or more aliquots of each batch using a rotator-facilitated in vitro release assay for at least about 48 hours, after storage of the aliquots of each batch at 2° C. to 8° C. for about 12 months from batch manufacture date, and an average rate of change in the cumulative percentage release of bupivacaine of the batches at the 48-hour time point is no less than-0.3%/month after storage of the aliquots of each batch at 2° C. to 8° C. for about 12 months.

A second aspect of the present disclosure relates to batches comprising compositions of bupivacaine encapsulated MVLs, the composition comprising:
bupivacaine residing inside a plurality of internal aqueous chambers of MVLs separated by lipid membranes, wherein the lipid membranes comprise DEPC, DPPG or a salt thereof, cholesterol, and tricaprylin; and
an aqueous medium in which the bupivacaine encapsulated MVLs are suspended, wherein the aqueous medium also comprises unencapsulated bupivacaine;
the total bupivacaine concentration in the composition is from 12 mg/mL to 17 mg/ml;
wherein the batches are manufactured within a period of six months, and the batches each has a volume of at least 100 liters;
wherein each batch has a cumulative percentage release of bupivacaine from 46% to 71% at a 24-hour time point, measured from two or more aliquots of each batch using a rotator-facilitated in vitro release assay for at least about 48 hours, after storage of the aliquots of each batch at 2° C. to 8° C. for about 12 months from batch manufacture date, and an average change in the cumulative percentage release of bupivacaine at the 24-hour time point is at least 0.5% after storage of the aliquots of each batch at 2° C. to 8° C. for about 12 months;
alternatively or additionally, each batch has a cumulative percentage release of bupivacaine from 60% to 85% at a 48-hour time point, measured from two or more aliquots of each batch using a rotator-facilitated in vitro release assay for at least about 48 hours, after storage of the aliquots of each batch at 2° C. to 8° C. for about 12 months from batch manufacture date, and an average change in the cumulative percentage release of bupivacaine at the 48-hour time point is no less than-5% after storage of the aliquots of each batch at 2° C. to 8° C. for about 12 months.

A third aspect of the present disclosure relates to batches comprising compositions of bupivacaine encapsulated MVLs, the composition comprising:
bupivacaine residing inside a plurality of internal aqueous chambers of MVLs separated by lipid membranes, wherein the lipid membranes comprise DEPC, DPPG or a salt thereof, cholesterol, and tricaprylin; and
an aqueous medium in which the bupivacaine encapsulated MVLs are suspended, wherein the aqueous medium also comprises unencapsulated bupivacaine;
the total bupivacaine concentration in the composition is from 12 mg/mL to 17 mg/mL;

wherein the batches are manufactured within a period of three months, and the batches each has a volume of at least 100 liters;

wherein each batch has a cumulative percentage release of bupivacaine from 46% to 71% at a 24-hour time point, measured from six aliquots of each batch using a rotator-facilitated in vitro release assay for at least about 48 hours, after storage of the aliquots of each batch at 2° C. to 8° C. for about 12 months from batch manufacture date, and the average rate of change in the cumulative percentage release of bupivacaine at the 24-hour time point is at least 0.05%/month after storage of the aliquots of each batch at 2° C. to 8° C. for about 12 months;

alternatively or additionally, each batch has a cumulative percentage release of bupivacaine from 60% to 85% at a 48-hour time point, measured from six aliquots of each batch using a rotator-facilitated in vitro release assay for at least about 48 hours, after storage of the aliquots of each batch at 2° C. to 8° C. for about 12 months from batch manufacture date, and the average rate of change in the cumulative percentage release of bupivacaine at the 48-hour time point is no less than 0.3%/month after storage of the aliquots of each batch at 2° C. to 8° C. for about 12 months;

wherein the average rate of change in the cumulative percentage release of bupivacaine is based on two to five batches, and at least one batch is manufactured 10 or more days apart from at least one other batch.

A fourth aspect of the present disclosure relates to batches comprising compositions of bupivacaine encapsulated MVLs, the composition comprising:

bupivacaine residing inside a plurality of internal aqueous chambers of MVLs separated by lipid membranes, wherein the lipid membranes comprise DEPC, DPPG or a salt thereof, cholesterol, and tricaprylin; and an aqueous medium in which the bupivacaine encapsulated MVLs are suspended, wherein the aqueous medium also comprises unencapsulated bupivacaine;

the total bupivacaine concentration in the composition is from 12 mg/mL to 17 mg/mL;

wherein the batches are manufactured within a period of three months, and the batches each has a volume of at least 100 liters;

wherein each batch has a cumulative percentage release of bupivacaine from 46% to 71% at a 24-hour time point, measured from six aliquots of each batch using a rotator-facilitated in vitro release assay for at least about 48 hours, after storage of the aliquots of each batch at 2° C. to 8° C. for about 12 months from batch manufacture date, and an average change in the cumulative percentage release of bupivacaine at the 24-hour time point is at least 0.5% after storage of the aliquots of each batch at 2° C. to 8° C. for about 12 months;

alternatively or additionally, each batch has a cumulative percentage release of bupivacaine from 60% to 85% at a 48-hour time point, measured from six aliquots of each batch using a rotator-facilitated in vitro release assay for at least about 48 hours, after storage of the aliquots of each batch at 2° C. to 8° C. for about 12 months from batch manufacture date, and an average change in the cumulative percentage release of bupivacaine at the 48-hour time point is no less than −5% after storage of the aliquots of each batch at 2° C. to 8° C. for about 12 months;

wherein the average change in the cumulative percentage release of bupivacaine is based on two to five batches, and at least one batch is manufactured 10 or more days apart from at least one other batch.

A fifth aspect of the present disclosure relates to a process for preparing a plurality of batches of bupivacaine encapsulated MVLs, the process of manufacturing a batch of the plurality of batches comprising:

(a) mixing a first aqueous solution comprising phosphoric acid with a volatile water-immiscible solvent solution to form a water-in-oil first emulsion, wherein the volatile water-immiscible solvent solution comprises DEPC, DPPG or a salt thereof, cholesterol, and tricaprylin, and wherein either the first aqueous solution or the solvent solution comprises bupivacaine;

(b) mixing the water-in-oil first emulsion with a second aqueous solution to form a water-in-oil-in-water second emulsion, wherein the second aqueous solution comprises lysine and at least one an osmotic agent;

(c) substantially removing the volatile water-immiscible solvent from the water-in-oil-in-water second emulsion by sparging the water-in-oil-in-water second emulsion to form a first aqueous suspension of bupivacaine encapsulated MVLs having a first volume;

(d) reducing the first volume of the first aqueous suspension of bupivacaine encapsulated multivesicular liposomes by a first microfiltration to provide a second aqueous suspension of bupivacaine encapsulated MVLs having a second volume, wherein the first microfiltration feed flow rate is at least 190 L/min;

(e) exchanging the second aqueous suspension medium with a saline solution by diafiltration to provide a third aqueous suspension of bupivacaine encapsulated MVLs having a third volume, wherein the diafiltration feed flow rate is at least 190 L/min; and (f) reducing the third volume of the third aqueous suspension by a second microfiltration to provide a batch of aqueous suspension of bupivacaine encapsulated MVLs having a target concentration of bupivacaine from 12 mg/mL to 17 mg/mL;

manufacturing a plurality of batches according to the steps of (a)-(f);

wherein the plurality of batches are manufactured within a period of six months and the batches each has a volume of at least 100 liters;

wherein each batch has a cumulative percentage release of bupivacaine from 46% to 71% at a 24-hour time point, measured from two or more aliquots of each batch using a rotator-facilitated in vitro release assay for at least about 48 hours, after storage of the aliquots of each batch at 2° C. to 8° C. for about 12 months from batch manufacture date, and an average rate of change in the cumulative percentage release of bupivacaine at the 24-hour time point is at least 0.05%/month after storage of the aliquots of each batch at 2° C. to 8° C. for about 12 months;

alternatively or additionally, each batch has a cumulative percentage release of bupivacaine from 60% to 85% at a 48-hour time point, measured from two or more aliquots of each batch using a rotator-facilitated in vitro release assay for at least about 48 hours, after storage of the aliquots of each batch at 2° C. to 8° C. for about 12 months from batch manufacture date, and the average rate of change in the cumulative percentage release of bupivacaine at the 48-hour time point is no less than −0.3%/month after storage of the aliquots of each batch at 2° C. to 8° C. for about 12 months.

A sixth aspect of the present disclosure relates to a process for preparing a plurality of batches of bupivacaine encapsulated MVLs, the process comprising:
- (a) mixing a first aqueous solution comprising phosphoric acid with a volatile water-immiscible solvent solution to form a water-in-oil first emulsion, wherein the volatile water-immiscible solvent solution comprises DEPC, DPPG or a salt thereof, cholesterol, and tricaprylin, and wherein either the first aqueous solution or the solvent solution comprises bupivacaine;
- (b) mixing the water-in-oil first emulsion with a second aqueous solution to form a water-in-oil-in-water second emulsion, wherein the second aqueous solution comprises lysine and at least one an osmotic agent;
- (c) substantially removing the volatile water-immiscible solvent from the water-in-oil-in-water second emulsion by sparging the water-in-oil-in-water second emulsion to form a first aqueous suspension of bupivacaine encapsulated MVLs having a first volume;
- (d) reducing the first volume of the first aqueous suspension of bupivacaine encapsulated multivesicular liposomes by a first microfiltration to provide a second aqueous suspension of bupivacaine encapsulated MVLs having a second volume, wherein the first microfiltration feed flow rate is at least 190 L/min;
- (e) exchanging the second aqueous suspension medium with a saline solution by diafiltration to provide a third aqueous suspension of bupivacaine encapsulated MVLs having a third volume, wherein the diafiltration feed flow rate is at least 190 L/min; and
- (f) reducing the third volume of the third aqueous suspension by a second microfiltration to provide a batch of aqueous suspension of bupivacaine encapsulated MVLs having a target concentration of bupivacaine from 12 mg/mL to 17 mg/mL;

manufacturing a plurality of batches according to the steps of (a)-(f);

wherein the batches are manufactured within a period of six months, and the batches each has a volume of at least 100 liters;

wherein each batch has a cumulative percentage release of bupivacaine from 46% to 71% at a 24-hour time point, measured from two or more aliquots of each batch using a rotator-facilitated in vitro release assay for at least about 48 hours, after storage of the aliquots of each batch at 2° C. to 8° C. for about 12 months from batch manufacture date, and an average change in the cumulative percentage release of bupivacaine at the 24-hour time point is at least 0.5% after storage of the aliquots of each batch at 2° C. to 8° C. for about 12 months;

alternatively or additionally, each batch has a cumulative percentage release of bupivacaine from 60% to 85% at a 48-hour time point, measured from two or more aliquots of each batch using a rotator-facilitated in vitro release assay for at least about 48 hours, after storage of the aliquots of each batch at 2° C. to 8° C. for about 12 months from batch manufacture date, and an average change in the cumulative percentage release of bupivacaine at the 48-hour time point is no less than −5% after storage of the aliquots of each batch at 2° C. to 8° C. for about 12 months.

A seventh aspect of the present disclosure relates to a process for preparing a plurality of batches of bupivacaine encapsulated MVLs, the process of manufacturing a batch of the plurality of batches comprising:
- (a) mixing a first aqueous solution comprising phosphoric acid with a volatile water-immiscible solvent solution to form a water-in-oil first emulsion, wherein the volatile water-immiscible solvent solution comprises bupivacaine, DEPC, DPPG or a salt thereof, cholesterol;
- (b) mixing the water-in-oil first emulsion with a second aqueous solution to form a water-in-oil-in-water second emulsion, wherein the second aqueous solution comprises lysine and dextrose;
- (c) substantially removing the volatile water-immiscible solvent from the water-in-oil-in-water second emulsion by sparging the water-in-oil-in-water second emulsion to form a first aqueous suspension of bupivacaine encapsulated MVLs having a first volume;
- (d) reducing the first volume of the first aqueous suspension of bupivacaine encapsulated multivesicular liposomes by a first microfiltration to provide a second aqueous suspension of bupivacaine encapsulated MVLs having a second volume, wherein the first microfiltration feed flow rate is at least 190 L/min;
- (e) exchanging the second aqueous suspension medium with a saline solution by diafiltration to provide a third aqueous suspension of bupivacaine encapsulated MVLs having a third volume, wherein the diafiltration feed flow rate is at least 190 L/min; and
- (f) reducing the third volume of the third aqueous suspension by a second microfiltration to provide a batch of aqueous suspension of bupivacaine encapsulated MVLs having a target concentration of bupivacaine from 12 mg/mL to 17 mg/mL;

manufacturing a plurality of batches according to the steps of (a)-(f);

wherein the plurality of batches are manufactured within a period of three months and the batches each has a volume of at least 100 liters;

wherein each batch has a cumulative percentage release of bupivacaine from 46% to 71% at a 24-hour time point, measured from six aliquots of each batch using a rotator-facilitated in vitro release assay, after storage of the aliquots of each batch at 2° C. to 8° C. for about 12 months from batch manufacture date, and an average rate of change in the cumulative percentage release of bupivacaine at the 24-hour time point is at least 0.05%/month after storage of the aliquots of each batch at 2° C. to 8° C. for about 12 months;

alternatively or additionally, each batch has a cumulative percentage release of bupivacaine from 60% to 85% at a 48-hour time point, measured from six aliquots of each batch using a rotator-facilitated in vitro release assay for at least about 48 hours, after storage of the aliquots of each batch at 2° C. to 8° C. for about 12 months from batch manufacture date, and the average rate of change in the cumulative percentage release of bupivacaine at the 48-hour time point is no less than −0.3%/month after storage of the aliquots of each batch at 2° C. to 8° C. for about 12 months;

wherein the average rate of change in the cumulative percentage release of bupivacaine is based on two to five batches, and at least one batch is manufactured 10 or more days apart from at least one other batch.

An eighth aspect of the present disclosure relates to a process for preparing a plurality of batches of bupivacaine encapsulated MVLs, the process of manufacturing a batch of the plurality of batches comprising:
- (a) mixing a first aqueous solution comprising phosphoric acid with a volatile water-immiscible solvent solution to form a water-in-oil first emulsion, wherein the volatile water-immiscible solvent solution comprises bupivacaine, DPPG or a salt thereof, DEPC, tricaprylin and cholesterol, and wherein either the first aqueous solution or the solvent solution comprises bupivacaine;

(b) mixing the water-in-oil first emulsion with a second aqueous solution to form a water-in-oil-in-water second emulsion, wherein the second aqueous solution comprises lysine and dextrose;

(c) substantially removing the volatile water-immiscible solvent from the water-in-oil-in-water second emulsion by sparging the water-in-oil-in-water second emulsion to form a first aqueous suspension of bupivacaine encapsulated MVLs having a first volume;

(d) reducing the first volume of the first aqueous suspension of bupivacaine encapsulated multivesicular liposomes by a first microfiltration to provide a second aqueous suspension of bupivacaine encapsulated MVLs having a second volume, wherein the first microfiltration feed flow rate is at least 190 L/min;

(e) exchanging the second aqueous suspension medium with a saline solution by diafiltration to provide a third aqueous suspension of bupivacaine encapsulated MVLs having a third volume, wherein the diafiltration feed flow rate is at least 190 L/min; and (f) reducing the third volume of the third aqueous suspension by a second microfiltration to provide a batch of aqueous suspension of bupivacaine encapsulated MVLs having a target concentration of bupivacaine from 12 mg/mL to 17 mg/mL;

manufacturing a plurality of batches according to the steps of (a)-(f);

wherein the batches are manufactured within a period of three months, and the batches each has a volume of at least 100 liters;

wherein each batch has a cumulative percentage release of bupivacaine from 46% to 71% at a 24-hour time point, measured from six aliquots of each batch using a rotator-facilitated in vitro release assay, after storage of the aliquots of each batch at 2° C. to 8° C. for about 12 months from batch manufacture date, and an average change in the cumulative percentage release of bupivacaine at the 24-hour time point is at least 0.5% after storage of the aliquots of each batch at 2° C. to 8° C. for about 12 months;

alternatively or additionally, each batch has a cumulative percentage release of bupivacaine from 60% to 85% at a 48-hour time point, measured from six aliquots of each batch using a rotator-facilitated in vitro release assay for at least about 48 hours, after storage of the aliquots of each batch at 2° C. to 8° C. for about 12 months from batch manufacture date, and an average change in the cumulative percentage release of bupivacaine at the 48-hour time point is no less than −5% after storage of the aliquots of each batch at 2° C. to 8° C. for about 12 months;

wherein the average change in the cumulative percentage release of bupivacaine is based on two to five batches, and at least one batch is manufactured 10 or more days apart from at least one other batch.

A further aspect of the present disclosure relates to a composition of bupivacaine encapsulated MVLs, prepared by any one of the embodiments of the processes as described herein.

A further aspect of the present disclosure relates to a method of treating or ameliorating pain in a subject in need thereof, comprising administering the composition of bupivacaine MVLs as described herein to the subject.

In addition to the features described above, additional features and variations will be readily apparent from the following descriptions of the drawings and exemplary embodiments. It is to be understood that these drawings depict typical embodiments, and are not intended to be limiting in scope.

BRIEF DESCRIPTION OF THE DRAWINGS

FIGS. 5A through 5F is a table illustrating the cumulative percentage release of bupivacaine at 24-hour and 48-hour after storage of bupivacaine MVLs samples at 5° C. for 12 months, and the samples were produced by the 45 L process.

FIG. 6 is a table illustrating the cumulative percentage release of bupivacaine at 24-hour and 48-hour after storage of bupivacaine MVLs samples at 5° C. for 12 months, and the samples were produced by the UK 200 L process.

FIG. 7 is a table illustrating the cumulative percentage release of bupivacaine at 24-hour and 48-hour after storage of bupivacaine MVLs samples at 5° C. for 12 months, and the samples were produced by the new process as described according to certain embodiments of the present disclosure.

DETAILED DESCRIPTION

Figure 1A:
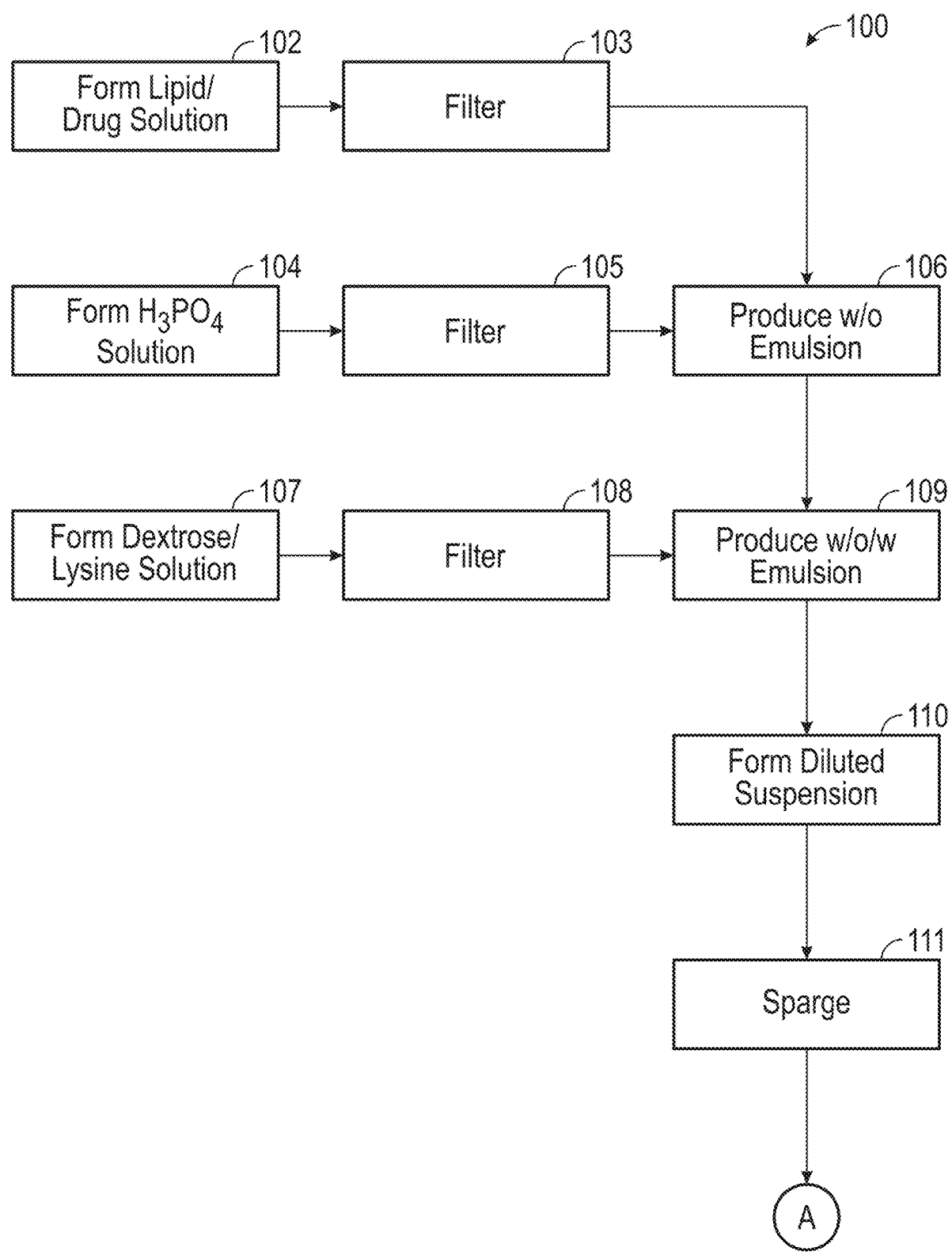
FIG. 1A illustrates a process flow chart of the formation of an initial aqueous suspension bupivacaine MVLs and solvent removal according to an embodiment of the manufacturing process described herein.

Embodiments of the present disclosure relate to new and improved commercial scale manufacturing processes for making bupivacaine encapsulated MVLs. The newly developed processes provide for an increased product yield as compared to prior processes used for the manufacturing of Exparel®, which are disclosed in U.S. Pat. No. 9,585,838, also referred to as the "45 L process"), and U.S. Pat. No.

11,033,495 (also referred to as the "UK 200 L process"), and U.S. Patent Application Publication No. 2022/0304932, each of which is incorporated by reference in its entirety. The 45 L process was approved by the FDA in 2012, has an average yield of about 75% and produces about 2.4K of vials of Exparel® product in 2023. The UK 200 L process was approved by the FDA in 2021, has an average yield of about 73% and produces about 10.5K vials of Exparel® product. As described in detail herein, the present disclosure relates to a new and improved commercial process of making bupivacaine MVLs, has an average of about 82% yield, and produces up to 14.4K vials of Exparel® product, which is a 37% increase of production from the UK 200 L process.

Furthermore, batches of Exparel® produced by the improved commercial process have demonstrated improved stability based on a rotator facilitated in vitro release assay (IVRA) test during stability studies conducted at about 5° C. for at least 12 months. Currently, Exparel® US product has a shelf life of 24 months based on the IVRA test performed at 5° C. at the following seven time points: 0 months, 3 months, 6 months, 9 months, 12 months, 18 months and 24 months. At each time point, the IVRA test detects at least the 24-hour and 48-hour cumulative percentage release of bupivacaine. For commercial lots, the IVRA test also detects the 4-hour and 168-hour cumulative percentage release of bupivacaine. The Exparel® product specification requires that the average cumulative percentage release of bupivacaine is 46%-71% at 24-hour and 60%-85% at 48-hour. It has been observed that during stability studies, the average cumulative percentage release of bupivacaine at 24-hour usually has a more pronounced decrease in the first 12 months, in particularly the first 6 months. Then the rate of decrease slows down during the second 12 months. It is important that the IVRA test results remain within the product specification during the shelf life of the product. As such, the flatter the trend line illustrating the rate of change in the cumulative percentage release of bupivacaine during the first 12 months, the more likely that the product will meet the IVRA specification during the entire 24 months. It has been observed that batches containing compositions of bupivacaine MVLs produced by the new process described herein have a flatter trend line illustrating the rate of change in the cumulative percentage release of bupivacaine in the first 12 months, as compared to the trend lines of the products produced by the 45 L process and the UK 200 L process. This surprising and unexpected observation may even allow Exparel® produced by the new process to surpass and extend the currently approved shelf life by the FDA.

Definitions

The section headings used herein are for organizational purposes only and are not to be construed as limiting the subject matter described.

As used herein, the terms "bupivacaine encapsulated multivesicular liposomes", "bupivacaine-MVLs" or "bupivacaine MVLs" refer to a multivesicular liposome composition encapsulating bupivacaine. In some embodiments, the composition is a pharmaceutical formulation, where the bupivacaine encapsulated multivesicular liposome particles are suspended in a liquid suspending medium to form a suspension. In some such embodiments, the BUP-MVL suspension may also include free or unencapsulated bupivacaine. In some cases, the free or unencapsulated bupivacaine may be less than about 8%, 7%, 6%, 5%, 4%, 3%, 2%, 1%, 0.5%, 0.2% or 0.1%, by weight of the total amount of the bupivacaine in the composition, or in a range defined by any of the two preceding values. In some embodiment, the free bupivacaine may be about 5% or less by weight of the total amount of the bupivacaine in the composition. In further embodiments, the free bupivacaine may be about 8% or less during the shelf life of the product (i.e., up to 2 years when stored at 2-8° C.).

As used herein, the term "encapsulated" means that bupivacaine is inside a liposomal particle, for example, the MVL particles. In some instances, bupivacaine may also be on an inner surface, or intercalated in a membrane, of the MVLs.

As used herein, the term "unencapsulated bupivacaine" or "free bupivacaine" refers to bupivacaine outside the liposomal particles, for example the MVL particles. For example, unencapsulated bupivacaine may reside in the suspending solution of these particles.

As used herein, the term "median particle diameter" refers to volume weighted median particle diameter of a suspension.

As used herein, a "pH adjusting agent" refers to a compound that is capable of modulating the pH of an aqueous phase.

As used herein, the terms "tonicity" and "osmolality" are measures of the osmotic pressure of two solutions, for example, a test sample and water separated by a semi-permeable membrane. Osmotic pressure is the pressure that must be applied to a solution to prevent the inward flow of water across a semi-permeable membrane. Osmotic pressure and tonicity are influenced only by solutes that cannot readily cross the membrane, as only these exert an osmotic pressure. Solutes able to freely cross the membrane do not affect tonicity because they will become equal concentrations on both sides of the membrane. An osmotic pressure provided herein is as measured on a standard laboratory vapor pressure or freezing point osmometer.

As used herein, the term "sugar" as used herein denotes a monosaccharide or an oligosaccharide. A monosaccharide is a monomeric carbohydrate which is not hydrolysable by acids, including simple sugars and their derivatives, e.g., aminosugars. Examples of monosaccharides include sorbitol, glucose, fructose, galactose, mannose, sorbose, ribose, deoxyribose, dextrose, neuraminic acid. An oligosaccharide is a carbohydrate consisting of more than one monomeric saccharide unit connected via glycosidic bond(s) either branched or in a chain. The monomeric saccharide units within an oligosaccharide can be the same or different. Depending on the number of monomeric saccharide units the oligosaccharide is a di-, tri-, tetra-, penta- and so forth saccharide. In contrast to polysaccharides, the monosaccharides and oligosaccharides are water soluble. Examples of oligosaccharides include sucrose, trehalose, lactose, maltose and raffinose.

As used herein, the term "amphipathic lipids" include those having a net negative charge, a net positive charge, and zwitterionic lipids (having no net charge at their isoelectric point).

As used herein, the term "neutral lipid" refers to oils or fats that have no vesicle-forming capabilities by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

Manufacturing Processes

Some embodiments of the present application relate to a commercial scale manufacturing process for preparing bupivacaine encapsulated multivesicular liposomes. The process comprising:

(a) mixing a first aqueous solution comprising phosphoric acid with a volatile water-immiscible solvent solution to form a water-in-oil first emulsion, wherein the volatile water-immiscible solvent solution comprises at least one phosphatidyl choline, at least one phosphatidyl glycerol, cholesterol, and at least one neutral lipid, and wherein either the first aqueous solution or the volatile water-immiscible solvent solution comprises bupivacaine; (b) mixing the water-in-oil first emulsion with a second aqueous solution to form a water-in-oil-in-water second emulsion;

(c) substantially removing the volatile water-immiscible solvent from the water-in-oil-in-water second emulsion by sparging the water-in-oil-in-water second emulsion to form a first aqueous suspension of bupivacaine encapsulated MVLs having a first volume;

(d) reducing the first volume of the first aqueous suspension of bupivacaine encapsulated multivesicular liposomes by a first microfiltration to provide a second aqueous suspension of bupivacaine encapsulated MVLs having a second volume, wherein the first microfiltration feed flow rate is at least 190 L/min;

(e) exchanging the second aqueous suspension medium with a saline solution by diafiltration to provide a third aqueous suspension of bupivacaine encapsulated MVLs having a third volume, wherein the diafiltration feed flow rate is at least 190 L/min; and (f) reducing the third volume of the third aqueous suspension by a second microfiltration to provide a final aqueous suspension of bupivacaine encapsulated MVLs having a target concentration of bupivacaine from about 12 mg/mL to about 17 mg/mL;

wherein the final aqueous suspension of bupivacaine encapsulated MVLs has a volume of at least 100 L, 125 L, 150 L, 175 L, 200 L, 225 L, 250 L, 275 L or 300 L. In some embodiments, the sparging in step (c) is conducted at a temperature of about 18° C. to about 20°

C. In some embodiments, the process has a bupivacaine encapsulated MVLs product yield of at least about 75%.

In some further embodiments, the process has a bupivacaine MVL product yield of at least about 76%, 77%, 78%, 79%, 80%, 81%, 82%, 83%, 84% or 85%. As described herein, the yield of bupivacaine MVLs is calculated as the following: (bupivacaine concentration in the final aqueous suspension×volume of the final aqueous suspension)/(the amount of bupivacaine in the first water-in-oil emulsion).

In some embodiments of the process, the volatile water-immiscible solvent solution comprises bupivacaine, 1,2-dipalmitoyl-sn-glycero-3-phospho-rac-(1-glycerol) (DPPG) or a salt thereof (e.g., a sodium salt), 1,2-dierucoylphosphatidylcholine (DEPC), tricaprylin and cholesterol. Other non-limiting exemplary phosphatidyl cholines include dioleyl phosphatidyl choline (DOPC), 1,2-didecanoyl-sn-glycero-3-phosphocholine (DDPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), or 1-stearoyl-2-palmitoyl-sn-glycero-3-phosphocholine (SPPC). Other non-limiting examples of phosphatidyl glycerols include 1,2-dierucoyl-sn-glycero-3-phospho-rac-(1-glycerol) (DEPG), 1,2-dilauroyl-sn-glycero-3-phospho-rac-(1-glycerol) (DLPG), 1,2-dimyristoyl-sn-glycero-3-phospho-rac-(1-glycerol) (DMPG), 1,2-dioleoyl-sn-glycero-3-phospho-rac-(1-glycerol) (DOPG), 1,2-distearoyl-sn-glycero-3-phospho-rac-(1-glycerol) (DSPG), 1-palmitoyl-2-oleoyl-sn-glycero-3-phospho-rac-(1-glycerol) (POPG), or salts thereof, for example, the corresponding sodium salts, ammonium salts, or combinations of the salts thereof. Other non-limiting exemplary neutral lipids may include but are not limited to triglycerides, propylene glycol esters, ethylene glycol esters, and squalene. Non-limiting exemplary triglycerides are triolein (TO), tripalmitolein, trimyristolein, trilinolein, tributyrin, tricaproin, tricaprylin (TC), and tricaprin. The fatty acid chains in the triglycerides useful in the present application can be all the same, or not all the same (mixed chain triglycerides), or all different. In some embodiments, the concentration of bupivacaine in the solvent solution is from about 5 mg/mL to about 100 mg/mL, from about 10 mg/mL to about 75 mg/mL, or from about 20 mg/mL to about 50 mg/mL. In some embodiments, the concentration of DEPC in the solvent solution is from about 1 mg/mL to about 30 mg/mL, from about 5 mg/mL to about 20 mg/mL, or from about 10 mg/mL to about 15 mg/mL. In some embodiments, the concentration of cholesterol in the solvent solution is from about 1 mg/mL to about 30 mg/mL, from about 2 mg/mL to about 15 mg/mL, or from about 5 mg/mL to about 10 mg/mL. In some embodiments, the concentration of DPPG in the solvent solution is from about 0.1 mg/mL to about 20 mg/mL, from about 0.5 mg/mL to about 10 mg/mL, or from about 1 mg/mL to about 5 mg/mL. In some embodiments, the concentration of tricaprylin in the solvent solution is from about 0.1 mg/mL to about 20 mg/mL, from about 0.5 mg/mL to about 10 mg/mL, or from about 1 mg/mL to about 5 mg/mL. In further embodiments, DEPC and DPPG in the solvent solution are in a mass ratio of about 4:1, 5:1, 6:1, 7:1, 8:1, 9:1, or 10:1.

In some embodiments of the process described herein, the volatile water-immiscible organic solvent comprises or is methylene chloride ($CH_2Cl_2$). In other embodiments, the volatile water-immiscible organic solvent comprises or is chloroform ($CHCl_3$).

In some embodiments of the process described herein, the second aqueous solution comprises a basic pH adjusting agent and at least one osmotic agent. Suitable organic bases that can be used as a basic pH adjusting agent include, but are not limited to histidine, arginine, lysine, tromethamine (Tris), etc. Suitable inorganic bases that can be used as a basic pH adjusting agent include, but are not limited to sodium hydroxide, calcium hydroxide, magnesium hydroxide, potassium hydroxide, etc. In some further embodiments, the basic pH adjusting agent comprises lysine. Non-limiting exemplary osmotic agents include monosaccharides (e.g., glucose, and the like), disaccharides (e.g., sucrose and the like), polysaccharide or polyols (e.g., sorbitol, mannitol, Dextran, and the like), or amino acids. In some further embodiments, the at least one osmotic agent is selected from dextrose, sorbitol, sucrose, or combinations thereof. In some further embodiments, the osmotic agent comprises dextrose. In some further embodiments, the second aqueous solution contains lysine and dextrose.

Processes of Making Batches of Bupivacaine MVLs with Improved In Vitro Release Profile Additional embodiment the present disclosure relates to a process for preparing a plurality of batches of bupivacaine encapsulated MVLs, the process of manufacturing a batch of the plurality of batches comprising:

(a) mixing a first aqueous solution comprising phosphoric acid with a volatile water-immiscible solvent solution to form a water-in-oil first emulsion, wherein the volatile water-immiscible solvent solution comprises DEPC, DPPG or a salt thereof, cholesterol, and tricaprylin, and wherein either the first aqueous solution or the solvent solution comprises bupivacaine;

(b) mixing the water-in-oil first emulsion with a second aqueous solution to form a water-in-oil-in-water second emulsion, wherein the second aqueous solution comprises lysine and at least one osmotic agent;

(c) substantially removing the volatile water-immiscible solvent from the water-in-oil-in-water second emulsion by sparging the water-in-oil-in-water second emulsion to form a first aqueous suspension of bupivacaine encapsulated MVLs having a first volume;

(d) reducing the first volume of the first aqueous suspension of bupivacaine encapsulated multivesicular liposomes by a first microfiltration to provide a second aqueous suspension of bupivacaine encapsulated MVLs having a second volume, wherein the first microfiltration feed flow rate is at least 190 L/min;

(e) exchanging the second aqueous suspension medium with a saline solution by diafiltration to provide a third aqueous suspension of bupivacaine encapsulated MVLs having a third volume, wherein the diafiltration feed flow rate is at least 190 L/min; and (f) reducing the third volume of the third aqueous suspension by a second microfiltration to provide a batch of aqueous suspension of bupivacaine encapsulated MVLs having a target concentration of bupivacaine from 12 mg/mL to 17 mg/mL; and manufacturing a plurality of batches according to the steps of (a)-(f). In some embodiments, bupivacaine is in the solvent solution. In some embodiments, the second aqueous solution comprises lysine and dextrose.

In some embodiments of the process of manufacturing a plurality of batches, the plurality of batches are manufactured within a period of six months and the batches each has a volume of at least 100 liters, 125 liters, 150 liters, 175 liters, 200 liters, 225 liters, 250 liters, 275 liters or 300 liters. In some further embodiments, the batches are manufactured within a period of 3 months. In some other embodiments, the batches are manufactured within a period of 2 months. In some embodiments, the batches are manufactured within a period of 30 days. In some embodiments, the batches are manufactured within a period of 3 months, each having a volume of at least 200 liters. In some embodiments, the batches are manufactured within a period of 2 months, each having a volume of at least 200 liters. In some embodiments, the batches are manufactured within a period of 30 days, each having a volume of at least 200 liters. In some embodiments, the sparging in step (c) is conducted at a temperate from about 18° C. to about 20° C.

In some embodiments of the process of manufacturing a plurality of batches, each batch has a cumulative percentage release of bupivacaine from 46% to 71% at a 24-hour time point, measured from two or more aliquots of each batch using a rotator-facilitated in vitro release assay for at least about 48 hours, after storage of the aliquots of each batch at 2° C. to 8° C. for about 12 months from batch manufacture date; and an average rate of change in the cumulative percentage release of bupivacaine at the 24-hour time point is at least 0.05%/month after storage of the aliquots of each batch at 2° C. to 8° C. for about 12 months. In some further embodiments, the average rate of change in the cumulative percentage release of bupivacaine at the 24-hour time point is, or is at least 0.06%/month, 0.07%/month, 0.08%/month, 0.09%/month, 0.10%/month, 0.11%/month, 0.12%/month, 0.13%/month, 0.14%/month, 0.15%/month, 0.16%/month, 0.17%/month, 0.18%/month, 0.19%/month, or 0.20%/month, or a range defined by any two of the preceding values, after storage of the aliquots of each batch at 2° C. to 8° C. for about 12 months. In some further embodiments, the average rate of change in the cumulative percentage release of bupivacaine at the 24-hour time point is at least 0.08%/month. In some embodiments, the average rate of change in the cumulative percentage release of bupivacaine at the 24-hour time point is 0.1%/month to 0.5%/month, for example, 0.15%/month to 0.45%/month, 0.20%/month to 0.40%/month, or 0.25%/month to 0.35%/month. In some embodiments, the average rate of change in the cumulative percentage release of bupivacaine is based on three batches, and one batch is manufactured at least 7 days apart (e.g., 7, 8, 9, or 10 or more days apart) from at least one other batch. In some other embodiments, the average rate of change in the cumulative percentage release of bupivacaine is based on two batches, and one batch is manufactured at least 7 days apart (e.g., 7, 8, 9, or 10 or more days apart) from the other batch. In some embodiments, the cumulative percentage release of bupivacaine for each batch is based on two aliquots, three aliquots, four aliquots, five aliquots, or six aliquots.

In some embodiments of the process of manufacturing a plurality of batches, each batch has a cumulative percentage release of bupivacaine from 60% to 85% at the 48-hour time point, measured from two or more aliquots of each batch using a rotator-facilitated in vitro release assay for at least about 48 hours, after storage of the aliquots of each batch at 2° C. to 8° C. for about 12 months from batch manufacture date, and the average rate of change in the cumulative percentage release of bupivacaine at the 48-hour time point is no less than −0.3%/month after storage of the aliquot of each batch at 2° C. to 8° C. for about 12 months. In some further embodiments, the average rate of change in the cumulative percentage release of bupivacaine at the 48-hour time point is, is no less than, or is at least −0.25%/month, −0.20%/month, −0.18%/month, −0.15%/month, −0.12%/month, −0.10%/month, −0.08%/month, −0.05%/month, no change (0%/month), 0.02%/month, 0.05%/month, 0.08%/month, 0.10%/month, 0.12%/month, 0.15%/month, 0.18%/month, 0.20%/month, 0.22%/month, or 0.25%/month, or a range defined by any two of the preceding values, after storage of the aliquots of each batch at 2° C. to 8° C. for about 12 months. In some further embodiments, the average rate of change in the cumulative percentage release of bupivacaine at the 48-hour time point is no less than −0.2%/month. In some further embodiments, the average rate of change in the cumulative percentage release of bupivacaine at the 48-hour time point is from −0.18%/month to 0.33%/month, for example, −0.15%/month to 0.30%/month, −0.12%/month to 0.28%/month, −0.10%/month to 0.25%/month, −0.08%/month to 0.22%/month, −0.05%/month to 0.20%/month, or 0%/month to 0.15%/month. In some embodiments, the average rate of change in the cumulative percentage release of bupivacaine is based on three batches, and one batch is manufactured at least 7 days apart (e.g., 7, 8, 9, or 10 or more days apart) from at least one other batch. In some other embodiments, the average rate of change in the cumulative percentage release of bupivacaine is based on two batches, and one batch is manufactured at least 7 days apart (e.g., 7, 8, 9, or 10 or more days apart) from the other batch. In some embodiments, the cumulative percentage release of bupivacaine for each batch is based on two aliquots, three aliquots, four aliquots, five aliquots, or six aliquots.

In some embodiments of the process of manufacturing a plurality of batches, each batch has a cumulative percentage release of bupivacaine from 46% to 71% at a 24-hour time point, measured from two or more aliquots of each batch using a rotator-facilitated in vitro release assay for at least about 48 hours, after storage of the aliquots of each batch at 2° C. to 8° C. for about 12 months from batch manufacture date; and wherein an average change in the cumulative percentage release of bupivacaine at the 24-hour time point is at least 0.5% after storage of the aliquots of each batch at 2° C. to about 8° C. for 12 months. In some further embodiments, the average change in the cumulative percentage release of bupivacaine at the 24-hour time point is or is at least 0.6%, 0.7%, 0.8%, 0.9%, 1.0%, 1.1%, 1.2%, 1.3%, 1.4%, 1.5%, 1.6%, 1.7%, 1.8%, 1.9% or 2.0% after storage of the aliquots of each batch at 2° C. to about 8° C. for 12 months. In some embodiments, the average change in the cumulative percentage release of bupivacaine at the 24-hour time point is at least 1%. In some further embodiments, the average change in the cumulative percentage release of bupivacaine at the 24-hour time point is 1% to 5%, for example, 1.5% to 4.5%, 2.0% to 4.0%, or 2.5% to 3.5%. In some embodiments, the average change in the cumulative percentage release of bupivacaine is based on three batches, and one batch is manufactured at least 7 days apart (e.g., 7, 8, 9, or 10 or more days apart) from at least one other batch. In some other embodiments, the average change in the cumulative percentage release of bupivacaine is based on two batches, and one batch is manufactured at least 7 days apart (e.g., 7, 8, 9, or 10 or more days apart) from the other batch. In some embodiments, the cumulative percentage release of bupivacaine for each batch is based on two aliquots, three aliquots, four aliquots, five aliquots, or six aliquots.

In some embodiments of the process of manufacturing a plurality of batches, each batch has a cumulative percentage release of bupivacaine from 60% to 85% at the 48-hour time point, measured from two or more aliquots of each batch using a rotator-facilitated in vitro release assay for at least about 48 hours, after storage of the aliquots of each batch at 2° C. to 8° C. for about 12 months from batch manufacture date; and an average change in the cumulative percentage release of bupivacaine at the 48-hour time point is no less than −5% after storage of the aliquots of each batch at 2° C. to 8° C. for about 12 months. In some further embodiments, the average change in the cumulative percentage release of bupivacaine at the 48-hour time point is or is no less than −4.5%, −4.0%, −3.5%, −3.0%, −2.5%, −2.0%, −1.5%, −1.0%, −0.5%, no change (0%), 0.5%, 1.0%, 1.5%, 2.0% or 2.5% after storage of the aliquots of each batch at 2° C. to about 8° C. for 12 months. In some embodiments, the average change in the cumulative percentage release of bupivacaine at the 48-hour time point is or is no less than −4%. In some further embodiments, the average change in the cumulative percentage release of bupivacaine at the 48-hour time point is from −4% to 6%, for example, −3.5% to 5.5%, −3.0% to 5.0%, −2.5% to 4.5%, −2.0% to 4.0%, −1.5% to 3.5%, or −1.0% to 3.0%. In some embodiments, the average change in the cumulative percentage release of bupivacaine is based on three batches, and one batch is manufactured at least 7 days apart (e.g., 7, 8, 9, or 10 or more days apart) from at least one other batch. In some other embodiments, the average change in the cumulative percentage release of bupivacaine is based on two batches, and one batch is manufactured at least 7 days apart (e.g., 7, 8, 9, or 10 or more days apart) from the other batch. In some embodiments, the cumulative percentage release of bupivacaine for each batch is based on two aliquots, three aliquots, four aliquots, five aliquots, or six aliquots.

In some embodiments, the cumulative percentage release of bupivacaine of each batch is measured as the average of three aliquots from each batch. In other embodiments, the cumulative percentage release of bupivacaine of each batch is measured as the average of six aliquots from each batch. In some further embodiments, the cumulative percentage release of bupivacaine is measured using the rotator-facilitated in vitro release assay. In some embodiments, the in vitro release assay is run for about 48 hours. In some other embodiments, the in vitro release assay is run for about 168 hours. In some embodiments, each aliquot has a cumulative percentage release of bupivacaine from 36% to 81% at the 24-hour time point. In some embodiments, each aliquot has a cumulative percentage release of bupivacaine from 50% to 95% at the 48-hour time point. In some embodiments, the cumulative percentage release of bupivacaine is measured after storage of the aliquots of each batch at about 5° C. for about 365 days from batch manufacture date.

In some embodiments, the batches are manufactured within a period of 3 months, each having a volume of at least 200 liters. In some further embodiments, the batches are manufactured within 30 days. In some such embodiments, each batch has a cumulative percentage release of bupivacaine from 46% to 71% at a 24-hour time point, measured from six aliquots of each batch using a rotator-facilitated in vitro release assay, after storage of the aliquots of each batch at 2° C. to 8° C. for about 12 months from batch manufacture date; wherein an average rate of change in the cumulative percentage release of bupivacaine at the 24-hour time point is at least 0.05%/month after storage of the aliquots of each batch at 2° C. to 8° C. for about 12 months; and wherein the average rate of change in the cumulative percentage release of bupivacaine is based on two to five batches, and at least one batch is manufactured 10 or more days apart from at least one other batch. In some further embodiments, the average rate of change in the cumulative percentage release of bupivacaine at the 24-hour time point is or is at least 0.06%/month, 0.07%/month, 0.08%/month, 0.09%/month, 0.10%/month, 0.11%/month, 0.12%/month, 0.13%/month, 0.14%/month, 0.15%/month, 0.16%/month, 0.17%/month, 0.18%/month, 0.19%/month, or 0.20%/month, or a range defined by any two of the preceding values, after storage of the aliquots of each batch at 2° C. to 8° C. for about 12 months. In some embodiments, the average rate of change in the cumulative percentage release of bupivacaine at the 24-hour time point is at least 0.1%/month. In some further embodiments, the average rate of change in the cumulative percentage release of bupivacaine at the 24-hour time point is 0.15%/month to 0.5%/month. In some embodiments, the in vitro release assay is run for about 48 hours. In some other embodiments, the in vitro release assay is run for about 168 hours. Alternatively or additionally, each batch has a cumulative percentage release of bupivacaine from 60% to 85% at the 48-hour time point, and the average rate of change in the cumulative percentage release of bupivacaine at the 48-hour time point is no less than −0.25%/month after storage of the aliquot of each batch at 2° C. to 8° C. for about 12 months. In some further embodiments, the average rate of change in the cumulative percentage release of bupivacaine at the 48-hour time point is, is no less than, or is at least −0.20%/month, −0.18%/month, −0.15%/month, −0.12%/month, −0.10%/month, −0.08%/month, −0.05%/month, no change (0%/month), 0.02%/month, 0.05%/month, 0.08%/month, 0.10%/month, 0.12%/month, 0.15%/month, 0.18%/month, 0.20%/month, 0.22%/month, or 0.25%/month, or a range defined by any two of the preceding values, after storage of the aliquots of each batch at 2° C. to 8° C. for about 12 months. In some embodiments, the average rate of change in the cumulative percentage release of bupivacaine at the 48-hour time point is no less than −0.2%/month. In some further embodiments, the average rate of change in the cumulative percentage release of bupivacaine at the 48-hour time point is from −0.18%/month to 0.33%/month, for example, −0.15%/month to 0.30%/month, −0.12%/month to 0.28%/month, −0.10%/month to 0.25%/month, −0.08%/month to 0.22%/month, −0.05%/month to 0.20%/month, or 0%/month to 0.15%/month. In some embodiments, the average rate of change in the cumulative percentage release of bupivacaine is based on three batches, and one batch is manufactured 10 or more days (e.g., 10, 15, 20, 25 or 30 days) apart from at least one other batch. In some other embodiments, the average rate of change in the cumulative percentage release of bupivacaine is based on two batches, and one batch is manufactured 10 or more days (e.g., 10, 15, 20, 25 or 30 days) apart from the other batch.

In some embodiments, the batches are manufactured within a period of 3 months, each having a volume of at least 200 liters. In some further embodiments, the batches are manufactured within 30 days. In some such embodiments, each batch has a cumulative percentage release of bupivacaine from 46% to 71% at a 24-hour time point, measured from six aliquots of each batch using a rotator-facilitated in vitro release assay, after storage of the aliquots of each batch at 2° C. to 8° C. for about 12 months from batch manufacture date; wherein an average change in the cumulative percentage release of bupivacaine at the 24-hour time point is at least 0.5% after storage of the aliquots of each batch at 2° C. to 8° C. for about 12 months; and wherein the average rate of change in the cumulative percentage release of bupivacaine is based on two to five batches, and at least one batch is manufactured 10 or more days apart from at least one other batch. In some further embodiments, the average change in the cumulative percentage release of bupivacaine at the 24-hour time point is, or is at least 0.6%, 0.7%, 0.8%, 0.9%, 1.0%, 1.1%, 1.2%, 1.3%, 1.4%, 1.5%, 1.6%, 1.7%, 1.8%, 1.9% or 2.0% after storage of the aliquots of each batch at 2° C. to about 8° C. for 12 months. In some embodiments, the average change in the cumulative percentage release of bupivacaine at the 24-hour time point is at least 1%. In some further embodiments, the average change in the cumulative percentage release of bupivacaine at the 24-hour time point is 1% to 5%. In some embodiments, the in vitro release assay is run for about 48 hours. In some other embodiments, the in vitro release assay is run for about 168 hours. Alternatively or additionally, each batch has a cumulative percentage release of bupivacaine from 60% to 85% at the 48-hour time point, and an average change in the cumulative percentage release of bupivacaine at the 48-hour time point is no less than −5% after storage of the aliquot of each batch at 2° C. to 8° C. for about 12 months. In some further embodiments, the average change in the cumulative percentage release of bupivacaine at the 48-hour time point is, or is no less than −4.5%, −4.0%, −3.5%, −3.0%, −2.5%, −2.0%, −1.5%, −1.0%, −0.5%, no change (0%), 0.5%, 1.0%, 1.5%, 2.0% or 2.5% after storage of the aliquots of each batch at 2° C. to about 8° C. for 12 months. In some embodiments, the average change in the cumulative percentage release of bupivacaine at the 48-hour time point is no less than −4%. In some further embodiments, the average change in the cumulative percentage release of bupivacaine at the 48-hour time point is from −4% to 6%. In some embodiments, the average change in the cumulative percentage release of bupivacaine is based on three batches, and one batch is manufactured 10 or more days (e.g., 10, 15, 20, 25 or 30 days) apart from at least one other batch. In some other embodiments, the average change in the cumulative percentage release of bupivacaine is based on two batches, and one batch is manufactured 10 or more days (e.g., 10, 15, 20, 25 or 30 days) apart from the other batch.

As described herein with respect to the any of the time points (e.g., 24-hour, 48-hour or 168-hour) in which cumulative percentage release of bupivacaine is tested, each time point is within ±15 minutes of the scheduled time points.

As described herein with respect to the rate of change in the cumulative percentage release of bupivacaine, each aliquot is measured at the following five time points: a first time point is within 30 days from batch manufacture date, a second time point is about 3 months from the batch manufacture date, a third time point which is about 6 months from the batch manufacture date, a fourth time point which is about 9 months from the batch manufacture date, and a fifth time point which is about 12 months from the batch manufacture date. Each time point of actual measurement is within ±30 days of the scheduled time point.

As described herein with respect to the change in the cumulative percentage release of bupivacaine after storage of the aliquots of each batch at 2° C. to 8° C. for about 12 months, the change is calculated as: % release of bupivacaine at about 12 months from batch manufacture date−% release of bupivacaine shortly after manufacturing (e.g., within 30 days from batch manufacture date when the batch product is filled into individual vials). Batch product is usually filled into individual vials within 7 days from manufacture date.

In some embodiments of the processes described herein, the mixing in step (a) is performed using a first mixer at a high shear speed. In some embodiments, the high shear speed is from about 1100 rpm to about 1300 rpm. For example, in some embodiments, the high shear speed is about 1100 rpm, about 1110 rpm, about 1120 rpm, about 1130 rpm, about 1140 rpm, about 1150 rpm, about 1160 rpm, about 1170 rpm, about 1180 rpm, about 1190 rpm, about 1200 rpm, about 1210 rpm, about 1220 rpm, about 1230 rpm, about 1240 rpm, about 1250 rpm, about 1260 rpm, about 1270 rpm, about 1280 rpm, about 1290 rpm, about 1300 rpm, or a range defined by any of the two preceding values. In some embodiment, the high shear speed is about 1200 rpm to about 1250 rpm. In some such embodiments, the mixing in step (a) is performed for about 65 minutes to about 75 minutes, for example, about 65, 66, 67, 68, 69, 70, 71, 72, 73, 74 or 75 minutes, or a range defined by any two of the preceding values. In some further embodiments, the mixing in step (a) is performed at the high speed from about 1200 rpm to about 1250 rpm or about 1225 rpm for about 70 minutes.

Proper mixing rate is important for forming the first emulsion droplets in a proper size range, which is important to the final product yield, the MVL particle stability and release properties. It was observed that when the mixing speed is too low or too high, the droplets formed in the first emulsion were either too big or too small. In some embodiments, mixing temperature and/or time may also affect the size of the droplet formed. In some further embodiments, the first mixer used in step (a) of the process has a blade diameter of about 8 inches to about 15 inches (e.g., about 8, 9, 10, 11, 12, 13, 14 or 15 inches). In some further embodiment, the first mixer has a 11 inch blade diameter. In some embodiments, two or more mixers may be used in step (a). In further embodiments, the first mixer used in step (a) of the process is not a static mixer. In other embodiments, the first mixer used in step (a) of the process is a static mixer. In further embodiments, the mixing in step (a) is performed at a temperature of about 20° C. to about 23° C. In some embodiments, the mixing in step (a) is performed at a temperature of about 21.5° C. In some further embodiments, the water-in-oil first emulsion has a volume of about 200 L to about 260 L, or from about 200 L to about 240 L, such as 200 L, 205 L, 210 L, 215 L, 220 L, 225 L, 230 L, 235 L or 240 L.

In some embodiments of the processes described herein, the mixing in step (b) is performed using a second mixer at a low shear speed. In some embodiments, the low shear speed is from about 445 rpm to about 680 rpm. In some embodiments, the low shear speed is for example, about 445 rpm, about 450 rpm, about 460 rpm, about 470 rpm, about 480 rpm, about 490 rpm, about 500 rpm, about 510 rpm, about 520 rpm, about 530 rpm, about 540 rpm, about 550 rpm, about 560 rpm, about 570 rpm, about 580 rpm, about 590 rpm, about 600 rpm, about 610 rpm, about 620 rpm, about 630 rpm, about 640 rpm, about 650 rpm, about 660 rpm, about 670 rpm, about 680 rpm, or a range defined by any of the two preceding values. In some further embodiments, the low shear speed is from about 615 rpm to about 650 rpm, or about 630 rpm. In some embodiments, the mixing in step (b) is performed for about 60 and about 85 seconds. In some embodiments, the mixing in step (b) is performed for about 69 seconds, about 70 seconds, about 71 seconds, about 72 seconds, about 73 seconds, about 74 seconds, about 75 seconds, about 76 seconds, about 77 seconds, about 78 seconds, about 79 seconds, about 80 seconds, about 81 seconds, about 82 seconds, about 83 seconds, about 84 seconds, or about 85 seconds, or a range defined by any two of the preceding values. In some further embodiments, the mixing in step (b) is performed at the low speed from about 615 rpm to about 650 rpm for about 70 seconds. In some other embodiments, the mixing in step (b) is performed with both the first mixer at a high speed from about 800 rpm to about 1000 rpm and a second mixer at a low speed from about 450 rpm to about 550 rpm for about 60 to 75 seconds. In some further embodiments, the second mixer used in step (b) of the process has a blade diameter of about 8 inches to about 15 inches, for example, about 8, 9, 10, 11, 12, 13, 14 or 15 inches. In some further embodiment, the second mixer has a 11 inch blade diameter. In some embodiments, the second mixer used in step (b) of the process is not a static mixer. In other embodiments, the second mixer used in step (b) of the process is a static mixer.

In some embodiments of the processes described herein, the second aqueous solution is stored at a temperature of about 18° C. to about 22° C. prior to the mixing in step (b). In some further embodiments, the mixing in step (b) is performed at a temperature of from about 18° C. to about 22° C., or from about 18° C. to about 20° C. In some embodiments, the mixing in step (b) is performed at a temperature of about 20° C. or less. For example, in some embodiments, the mixing in step (b) is performed at a temperature of about 19° C. to about 20° C. The water-in-oil-in water (w/o/w) second emulsion is not as stable as the first emulsion. As such, a low shear speed is used in mixing step to reduce the disruption of the spherules formed in this step. In addition, the mixing time, speed, and temperature in step (b) are also important to yield the final MVL particles in the target diameters and have the desired release properties. If mixing time is too short, it leads to a larger particle size. In some embodiments, the volume ratio of the first emulsion to the second emulsion is about 1:1, 1:1.5, 1:2, 1:2.5, 1:3, 1:3.5, 1:4, 1:4.5 or 1:5. In one embodiment, the volume ratio of the first emulsion to the second emulsion is about 1:3.5. In further embodiment, additional second aqueous solution is added to dilute the second emulsion prior to the sparging step such that the final volume ratio of the first emulsion to the diluted second emulsion is about 1:10 to about 1:30, for example, about 1:10, 1:12, 1:14, 1:16, 1:18, 1:20, 1:22, 1:24, 1:26, 1:28 or 1:30. In one embodiment, the volume ratio of the first emulsion to the diluted second emulsion is about 1:20.

In some embodiments of the processes described herein, substantially removing the volatile water-immiscible solvent from the water-in-oil-in-water second emulsion comprises exposing the second emulsion to a gas atmosphere. Organic solvent may be substantially removed by blowing a gas over the second emulsion, or sparging gas in the second emulsion. In some further embodiments, substantially removing the volatile water-immiscible solvent may comprise bubbling a sparging gas through the second emulsion or the diluted second emulsion. In some embodiments, the sparging gas is nitrogen.

In some embodiments of the processes described herein, sparging is performed at a temperature of about 18° C. to about 22° C., about 18° C. to about 21° C., or about 18° C. to about 20° C. In some embodiments, sparging is performed at a temperature of about 19° C. In some embodiments, sparging is performed at a temperature of about 19° C. or less. For example, in some embodiments, sparging is performed at a temperature of about 18° C. to about 19° C. It was observed that sparging performed at lower temperatures can provide less product breakage (MVL particle breakage) and consequently improved product yield. For example, it was observed that sparging performed at lower temperatures is correlated with lower conductivity values in the aqueous suspension. Lower conductivity values can be representative of less product breakage due to less release of the contents inside of internal aqueous chambers of the MVLs, and consequently higher product yield. Accordingly, sparging performed at a temperature of about 20° C., about 19° C., about 19° C. or less, from about 18° C. to about 20° C., or from about 18° C. to about 19° C. can beneficially provide an improved product yield in comparison to higher temperatures. In some embodiments, sparging performed at a temperature of about 19° C., about 19° C. or less, or from about 18° C. to about 19° C. can provide improved product yield in comparison to sparging performed at above 20° C. (e.g., at about 21° C. or 22° C.).

In addition, the sparging time also impact the product yield. Longer sparging time usually results in lower product yield at least due to increased product breakage. In some embodiments, the sparging is performed for about 15 minutes to about 30 minutes, for example, about 15, 16, 17, 18, 19, 20, 21, 22, 23, 24, 25, 26, 27, 28, 29 or 30 minutes, or a range defined by any two of the preceding values. In some further embodiments, sparging is performed for about 19 minutes to about 25 minutes, or about 22 minutes at a temperature of about 19° C. In some further embodiments, sparging the water-in-oil-in-water second emulsion comprises sparging at a sparging gas flow rate of about 1500 to about 3000 SLPM, about 1750 SLPM to about 2750 SLPM, or about 1874 SLPM to about 2500 SLPM. In some further embodiments, sparging the water-in-oil-in-water second emulsion is at a sparging gas flow rate of about 2400 SLPM for about 22 minutes.

In some embodiments, conductivity values of the aqueous suspension can be measured to determine that sparging is complete. Additionally or alternatively, the pH of the aqueous suspension may also be measured to determine whether sparging is complete. For example, a drop in pH can be observed during the sparing process, at least partially due to the release of the phosphoric acid from the internal aqueous chambers of the MVLs.

It may be advantageous for the pre-sparging second emulsion (e.g., diluted second emulsion) to be at a desired temperature at the beginning of sparging. In certain embodiments, the mixing in step (b) prior to sparging may occur for a relatively short period of time (e.g., 65 to 85 seconds). In such embodiments, it may be desirable for the components of the second emulsion to be at or near a desired temperature during the mixing in step (b). In such embodiments, the desired temperature may be provided by providing the second aqueous solution at or near the desired temperature. For example, the second aqueous solution can be provided at a temperature of about 19° C., about 19° C. or less, about 18° C. to about 19° C., or about 18° C. to about 20° C.

In certain embodiments, it was observed that sparging temperatures may affect particle size and/or particle size distribution (e.g., median particle size and/or particle size distribution). While lower temperatures (e.g., about 19° C., about 19° C. or less, about 18° C. to about 19° C., or about 18° C. to about 20° C.) may provide improved product yield, it was observed that lower temperatures may result in an increased median particle size and/or an increased particle size distribution. In certain embodiments, it was observed that the shear speed of mixing, the mixing temperature, and/or the mixing time in step (b) may affect median particle size and/or particle size distribution. In certain embodiments, the shear speed of the mixing and/or the mixing time in step (b) can be selected to counteract the effects of the lower temperatures on median particle size and/or particle size distribution. In certain embodiments, it was observed that higher mixing speeds can result in smaller median particle sizes than lower mixing speeds. In some embodiments in which sparging is performed at lower temperatures (e.g., about 19° C., about 19° C. or less, from about 18° C. to about 19° C., or from about 18° C. to about 20° C.), the mixing speeds for the mixing in step (b) can be about 520 rpm, at least about 520 rpm, about 535 rpm, at least about 535 rpm, about 575 rpm, at least 575 rpm, about 630 rpm, at least about 630 rpm, or from 615 rpm to 680 rpm. In some embodiments in which sparging is performed at lower temperatures (e.g., about 19° C., about 19° C. or less, from about 18° C. to about 19° C., or from about 18° C. to about 20° C.), a mixing times of about 68 seconds to 72 seconds or about 70 seconds can be used. In some embodiments, a particular ramp rate may be used to increase the speed of the mixer to the desired mixing speed. A ramp rate is how quick the mixer reaches the target mixing speed. The ramp rate impacts the duration the mixer takes to reach the target mixing speed, and thereby increase or decrease the total amount of mixing energy utilized for the mixing step for a given mixing time.

In some embodiments of the processes described herein, when sparging is performed at a temperature of about 19° C., a mixing speed of 630 rpm and a mixing time of 70 seconds may be used with a particular ramp rate. In some embodiments, other combinations of mixing speeds, ramp rates, and/or mixing times may be selected to provide similar results, such as, for example, lower mixing speeds with faster ramp rates, lower mixing speeds with longer mixing times, or faster mixing speeds with shorter mixing times.

Exparel® product specification includes the following particle size (volume-weighted diameter) requirements: $d_{10}$ is no larger than 12.0 μm, $d_{50}$ (median) is from 24 μm to 31.0 μm, and $d_{90}$ is no larger than 62.0 μm during the shelf life of the product. The products manufactured by the 45 L process in 2022 (n=144) have a $d_{50}$ of 24.6 μm to 27.1 μm and a $d_{90}$ of 46.2 μm to 52.2 μm. In contrast, the products manufactured by the 200 L UK process (n=75) have a $d_{50}$ of 25.3 μm to 28.9 μm and a $d_{90}$ of 52.2 μm to 61.8 μm, while the products $d_{10}$ manufactured by both processes is about 13.5 μm to 15.0 μm. It was observed that when the manufacturing scale was substantially increased from 45 L to 200 L, the MVL products had a wider particle size distribution (the difference between $d_{90}$ and $d_{10}$). As the MVL particles have the tendency to agglomerate during storage and results in larger $d_{90}$ value overtime, it is important that the product has a narrower particle size distribution and smaller $d_{90}$ at the initial release to ensure that the $d_{90}$ is within the product specification during the entire shelf life, and also allow for a wide range of median particle size ($d_{50}$) to be achieved without failing the $d_{90}$ particle size specification. It was unexpectedly observed that higher microfiltration feed flow rates in step (d) can result in smaller particle size distribution than lower microfiltration feed flow rates. In some instance, higher microfiltration feed flow rates in step (d) can result in smaller particle size distribution without substantial reduction in median particle size ($d_{50}$). Higher feed flow rates may also reduce the overall time of the microfiltration in step (d), for example, by allowing for higher permeate flow rates and consequently less processing time. Reduced overall time of step (d) may be preferable, for example, because the suspension is less stable during step (d). In some embodiments, higher microfiltration feed flow rates can reduce the risk of filters clogging. In some embodiments, the more dilute the suspension, the less shear is imparted at the same flow rate. When the suspension is initially dilute, high feed flow rates may be used and then reduced linearly over the course of step (d) until an end target level of concentration is reached.

In some embodiments of the processes described herein, the first microfiltration is conducted with a beginning first microfiltration feed flow rate from about 190 L/min to about 400 L/min, or from about 200 L/min to about 350 L/min, and an end first microfiltration feed flow rate from about 190 L/min to about 310 L/min. In some embodiments, the microfiltration feed flow rate in step (d) can decrease during the microfiltration in step (d). For example, in some embodiments, at the start of the microfiltration in step (d), the feed flow rate can be from about 290 L/min to about 350 L/min. In some embodiments, at the start of the microfiltration in step (d), the feed flow rate can be about 320 L/min to about 340 L/min. In some embodiments, at the end of the microfiltration in step (d), the feed flow rate can be about 190 L/min to about 310 L/min. In some embodiments, at the end of the microfiltration in step (d), the feed flow rate can be about 300 L/min or from about 280 L/min to about 300 L/min. In some embodiments, the feed flow rate can decrease linearly or approximately linearly in relation to the level of liquid in the sparging vessel or the concentration of bupivacaine MVLs during the microfiltration in step (d). In some embodiments, decreasing the feed flow rate during the microfiltration of step (d) can prevent product breakage as the aqueous suspension of bupivacaine encapsulated multivesicular liposomes becomes less dilute.

In some further embodiments, in which sparging is performed at lower temperatures (e.g., about 19° C., about 19° C. or less, about 18° C. to about 19° C., or about 18° C. to about 20° C.), higher microfiltration feed flow rates, such as feed flow rates of about 340 L/min or from about 340 L/min to about 350 L/min at the start of microfiltration and/or about 300 L/min or from about 300 L/min to about 310 L/min at the end of microfiltration can be used.

Figure 2:
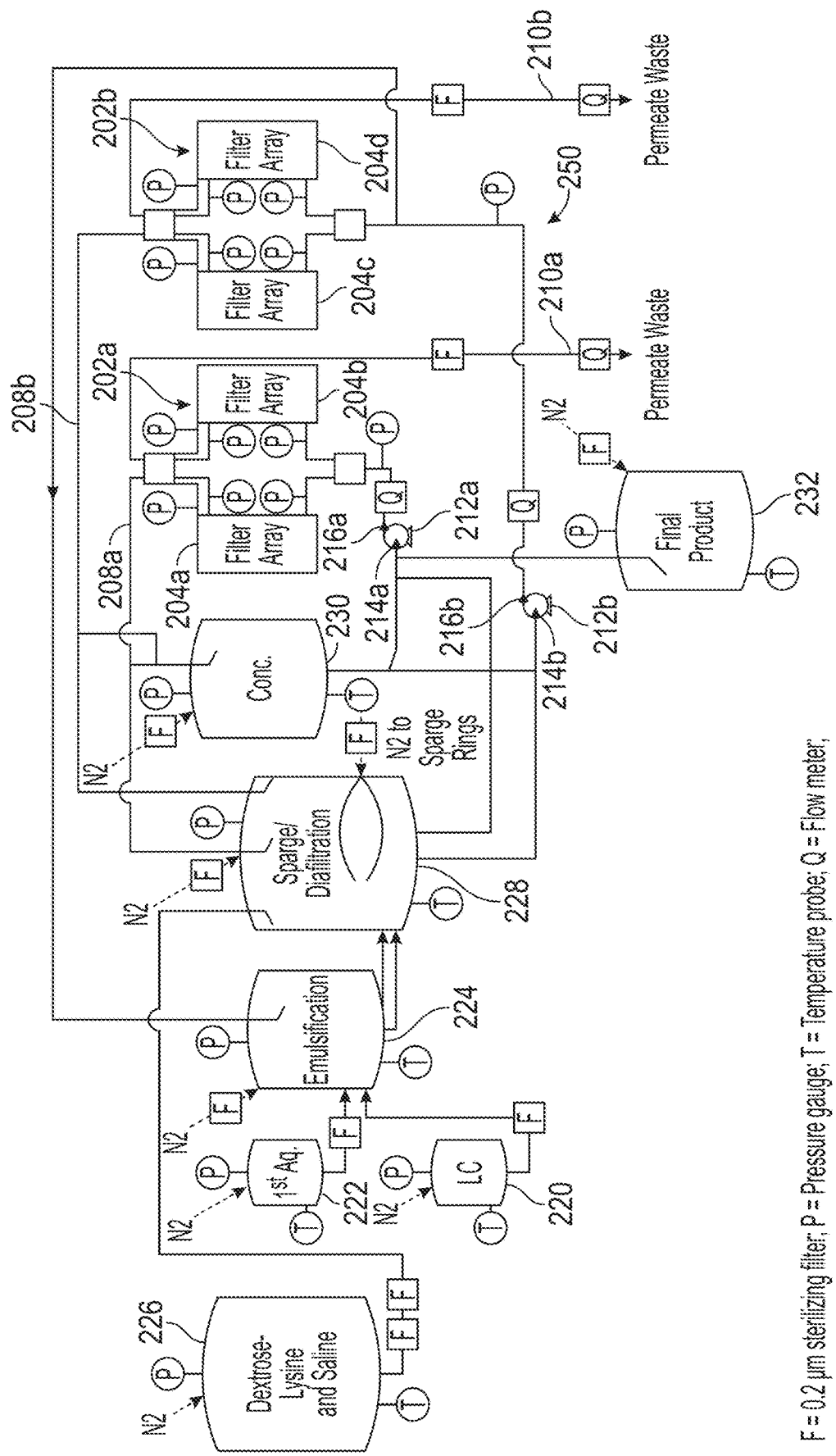
FIG. 2 illustrate a schematic diagram as an embodiment of a system for performing a manufacturing process.

In some embodiments of the processes described herein, wherein step (e) is performed using two sets of filtration modules, wherein each set of the filtration modules operate independently of the other. In further embodiments, each set of the filtration module comprises three, four, five, six or more hollow fiber filters, each having a membrane pore size from about 0.1 m to about 0.2 m. One embodiment of the filtration modules is illustrated in FIG. 2.

In some embodiments of processes described herein, the diafiltration step (e) is performed until the aqueous suspending medium of the second aqueous suspension is substantially replaced with the saline solution multiple times (e.g., at least 2.0, 2.5, 3.0, 3.5, 4.0, 4.5 or 5.0 times volume exchanges). It was unexpectedly observed that higher diafiltration feed flow rates can result in smaller particle size distributions than lower diafiltration feed flow rates. In some instance, it was observed that higher diafiltration feed flow rates can result in smaller particle size distributions than lower diafiltration feed flow rates without impacting product yield or the percentage of free bupivacaine. As yield was not impacted by the higher recirculation rates, without being bound by a particular theory, this observation suggests that higher diafiltration feed flow rates do not destroy particles but may operate by another mechanism, such as reducing agglomeration. Higher diafiltration feed flow rates may also reduce the overall time of the diafiltration, for example, by allowing for higher permeate flow rates without fouling or clogging the filters. In some embodiment, the different diafiltration feed flow rates can be used at different stages throughout diafiltration. For example, in some embodiments, during a first stage of diafiltration (e.g., first volume exchange), the feed flow rate can be about 190 L/min to about 310 L/min. In some embodiments, during the first stage of diafiltration, the feed flow rate can be about 250 L/min to about 310 L/min, or about 300 L/min. In some embodiments, it was observed that higher diafiltration feed flow rates at later stages of the diafiltration process can reduce product yield. Accordingly, in some embodiments, the diafiltration feed flow rate is reduced during the second stage of diafiltration to maintain a desired product yield. In in some embodiments, the diafiltration feed flow rate can be reduced during the second stage of diafiltration to maintain a desired product yield while maximizing the reduction in particle size distribution. In some embodiments, during a second stage of diafiltration, the feed flow rate can be about 190 L/min to about 265 L/min. In some embodiments, during the second stage of diafiltration (e.g., additional volume exchanges), the feed flow rate can be about 245 L/min to about 265 L/min, or about 255 L/min.

In some further embodiments, in which sparging is performed at lower temperatures (e.g., about 19° C., about 19° C. or less, about 18° C. to about 19° C., or about 18° C. to about 20° C.), higher diafiltration feed flow rates, such as feed flow rates of about 290 L/min to about 310 L/min or about 300 L/min in the first stage, and/or about 245 L/min to about 265 L/min or about 255 L/min in the second stage can be used.

In some embodiments of the processes described herein, the second microfiltration is conducted with a beginning second microfiltration feed flow rate of about 190 L/min to about 265 L/min. In some embodiments, the second microfiltration feed flow rate in step (f) can decrease during the microfiltration in step (f). For example, in some embodiments, at the start of the second microfiltration in step (f), the feed flow rate can be about 245 L/min to about 265 L/min, or about 255 L/min. In some embodiments, at the end of the second microfiltration in step (f), the feed flow rate can be about 120 L/min to about 190 L/min. In some embodiments, at the end of the second microfiltration in step (f), the feed flow rate can be about 170 L/min to about 190 L/min or about 180 L/min. In some embodiments, the feed flow rate can decrease linearly or approximately linearly during step (f) in relation to the MVL concentration in the third aqueous suspension. In some embodiments, decreasing the feed flow rate during the microfiltration of step (f) can prevent filter clogging and/or product damage as the aqueous suspension of bupivacaine encapsulated multivesicular liposomes becomes less dilute. Higher microfiltration feed flow rates may also reduce the overall time of the microfiltration in step (f).

In some embodiments of processes described herein, step (f) may be performed until a target concentration of bupivacaine MVLs is reached, for example, a target bupivacaine concentration in the final aqueous suspension can be from about 12 mg/mL to about 17 mg/mL. In some further embodiments, the final aqueous suspension of bupivacaine encapsulated multivesicular liposomes is transferred to a bulk product vessel, and subsequently filled into individual vials.

A further aspect of the present disclosure relates to a process for preparing bupivacaine encapsulated multivesicular liposomes (MVLs), the process comprising:
  (a) mixing a first aqueous solution comprising phosphoric acid with a volatile water-immiscible solvent solution to form a water-in-oil first emulsion, wherein the volatile water-immiscible solvent solution comprises bupivacaine, 1,2-dipalmitoyl-sn-glycero-3-phospho-rac-(1-glycerol) (DPPG) or a salt thereof, 1,2-dierucoylphosphatidylcholine (DEPC), tricaprylin and cholesterol, and wherein the first emulsion has a volume of at least 200 L;

(b) mixing the water-in-oil first emulsion with a second aqueous solution to form a water-in-oil-in-water second emulsion, wherein the second aqueous solution comprises lysine and dextrose;

(c) substantially removing the volatile water-immiscible solvent from the water-in-oil-in-water second emulsion by sparging the water-in-oil-in-water second emulsion to form a first aqueous suspension of bupivacaine encapsulated MVLs having a first volume, wherein the sparging is performed at a temperature of 18° C. to 20° C. for no more than 25 minutes;

(d) reducing the first volume of the first aqueous suspension of bupivacaine encapsulated MVLs by a first microfiltration to provide a second aqueous suspension of bupivacaine encapsulated MVLs having a second volume, wherein the first microfiltration feed flow rate is about 190 L/min to about 400 L/min;

(e) exchanging the second aqueous suspension medium with a saline solution by diafiltration to provide a third aqueous suspension of bupivacaine encapsulated MVLs having a third volume, wherein the diafiltration feed flow rate is from about 190 L/min to about 350 L/min; and (f) reducing the third volume of the third aqueous suspension by a second microfiltration to provide a final aqueous suspension of bupivacaine encapsulated MVLs having a target concentration of bupivacaine from about 12 mg/mL to about 17 mg/mL;

wherein the final aqueous suspension of bupivacaine encapsulated MVLs has a volume of at least about 200 L; and wherein the process has a bupivacaine MVL product yield of at least about 75%. In some further embodiments, the final aqueous suspension of bupivacaine encapsulated MVLs has a volume of at least about 250 L. In still further embodiments, the process has a bupivacaine MVL product yield of at least about 76, 77, 78, 79, or 80%.

In any embodiments of the processes described herein, the volume ratio of the first emulsion to the second emulsion is about 1:1, 1:1.5, 1:2, 1:2.5, 1:3, 1:3.5, 1:4, 1:4.5 or 1:5. In one embodiment, the volume ratio of the first emulsion to the second emulsion is about 1:3.5. In further embodiment, additional second aqueous solution is added to dilute the second emulsion prior to the sparging step such that the final volume ratio of the first emulsion to the diluted second emulsion is about 1:10 to about 1:30, or about 1:20. In some embodiments, the first microfiltration is conducted with a beginning first microfiltration feed flow rate from about 290 L/min to about 350 L/min, and an end first microfiltration feed flow rate from about 250 L/min to about 310 L/min, decreasing approximately linearly in relation to the level of liquid in the sparging vessel or the bupivacaine MVL concentration in the first aqueous suspension. In some such embodiments, the beginning first microfiltration feed flow rate is about 340 L/min, and the end first microfiltration feed flow rate is about 300 L/min. In some embodiments, the filtration feed flow rate during a first stage of diafiltration is about 250 L/min to about 310 L/min, and the filtration feed flow rate during a second stage of diafiltration is about 245 L/min to about 265 L/min. In some further embodiments, the filtration feed flow rate during a first stage of diafiltration is about 300 L/min, and the filtration feed flow rate during a second stage of diafiltration is about 255 L/min. In some embodiments, sparging the water-in-oil-in-water second emulsion is performed at a temperature of about 19° C. In some embodiments, the mixing in step (a) is performed using a first mixer at a high speed from about 1100 rpm to about 1300 rpm for about 65 minutes to about 75 minutes. In some further embodiments, the mixing in step (a) is performed at the high speed from about 1200 rpm to about 1250 rpm for about 70 minutes. In some further embodiments, the water-in-oil first emulsion has a volume of about 200 L to about 260 L or about 200 L to about 240 L. In some embodiments, the mixing in step (b) is performed at a low speed from about 445 rpm to about 680 rpm for about 60 to 85 seconds. In some further embodiments, the mixing in step (b) is performed at the low speed from about 615 rpm to about 650 rpm for about 70 seconds.

In any embodiments of the processes described herein, steps (d), (e) and (f) is conducted with a crossflow filtration system that is configured to switch between microfiltration and diafiltration mode, wherein the crossflow filtration system comprises a plurality of independently operating crossflow modules. In some embodiments, each crossflow module comprises at least one filter array, and each filter array comprises a plurality of hollow fiber filters. In some further embodiments, each crossflow module comprises two filter arrays, and each filter array comprises six hollow fiber filters. In some further embodiments, the crossflow filtration system comprises four filter arrays, and each filter array comprises six hollow fiber filters. In some embodiments, the crossflow filtration system further comprises at least one turbidity sensor downstream of the filter array for detection of loss of filter integrity during active manufacture.

Figure 1B:
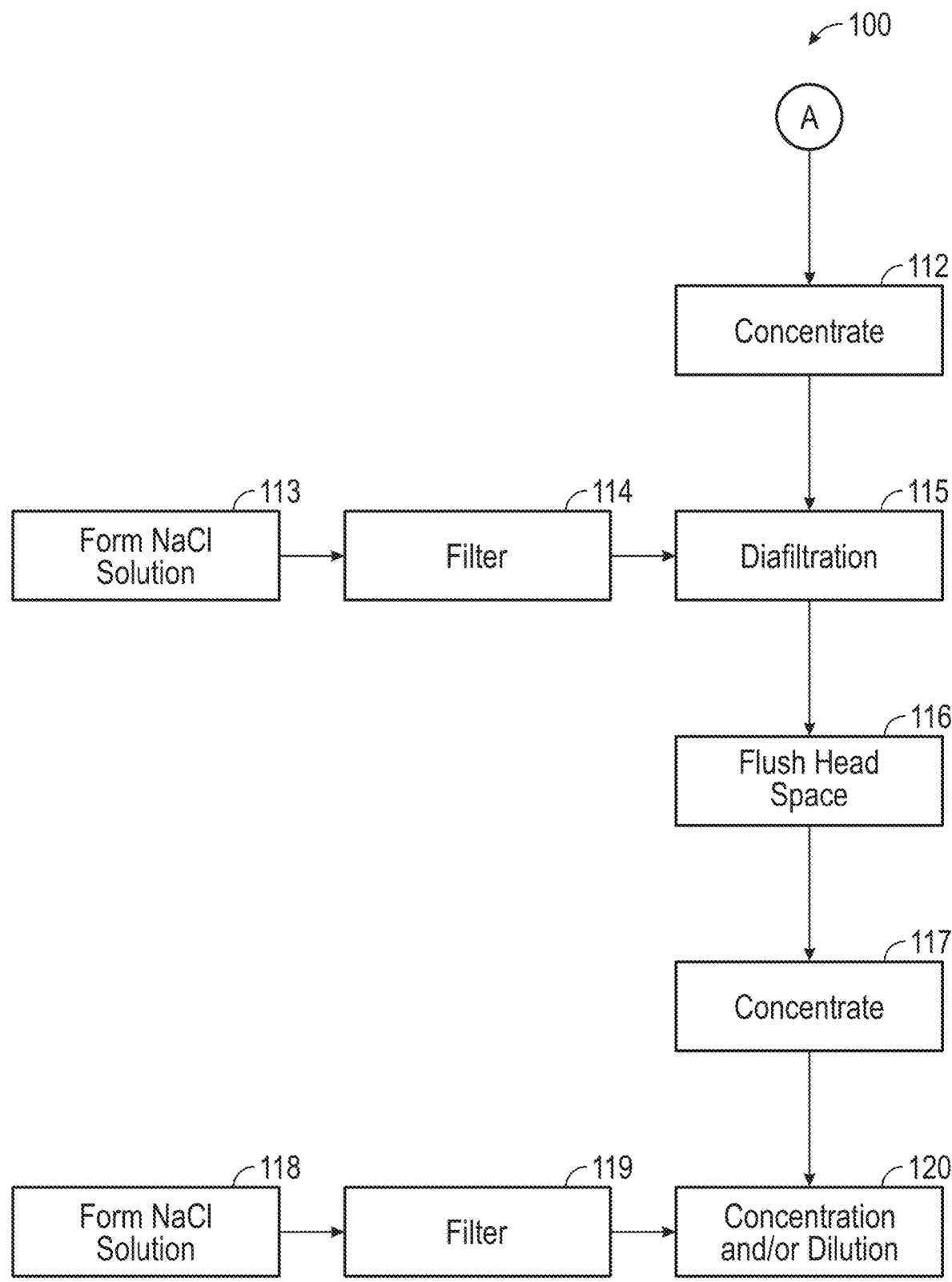
FIG. 1B illustrates a process flow chart of additional steps of concentration, diafiltration and solvent removal, and additional concentration of the initial aqueous suspension of bupivacaine MVLs according to an embodiment of the manufacturing process described herein.

FIGS. 1A-1B are process flow charts, each depicting a portion of the bupivacaine MVLs manufacturing process 100 according to some embodiments described herein. The circled A symbol indicates the connection point between FIG. 1A and FIG. 1B. As shown in FIGS. 1A-1B, bupivacaine MVLs is produced via an aseptic double-emulsion process. The bulk manufacturing system is a closed, sterilized system into which all process solutions are sterile-filtered through 0.2 μm filters.

As shown in FIG. 1A, the process 100 includes a step 102, wherein DEPC, DPPG, cholesterol, tricaprylin, and bupivacaine are dissolved in methylene chloride to form a lipid/drug solution 102. At a step 103, the lipid solution is filtered through a 0.2 μm membrane filter into a sterilized vessel. At a step 104, phosphoric acid is dissolved in WFI (water for injection) to form a $H_3PO_4$ solution (first aqueous solution). At a step 105, the $H_3PO_4$ solution is filtered through a 0.2 μm membrane filter into a sterilized vessel. Under aseptic conditions, the filtered lipid/drug solution is combined with the filtered $H_3PO_4$ solution in a volume ratio of 1:1 at an emulsification step 106 using agitation to produce a w/o emulsion (i.e., first emulsion). High shear mixing of the lipid/drug solution with the phosphoric acid solution is performed, wherein bupivacaine is ionized by the phosphoric acid and partitions into the internal aqueous phase. This forms a water-in-oil first emulsion. In some embodiments, the volume of this water in oil first emulsion can be about 200 L to about 260 L. In some embodiments, the volume of the water in oil first emulsion is about 200 L, 210 L, 220 L, 230 L, or 240 L. In some alternative embodiments, bupivacaine may be present in the first aqueous solution additionally or alternatively to being present in the lipid/drug solution.

At a step 107, lysine and dextrose are combined in WFI to form a dextrose/lysine solution (second aqueous solution). In certain embodiments, the dextrose/lysine solution may be kept at a temperature of about 19° C., about 19° C. or less, about 18° C. and about 19° C., or about 18° C. to about 20° C.

At a step 108, the dextrose/lysine solution is filtered through a 0.2 μm membrane filter into a sterilized vessel (e.g., a sparging vessel). In certain embodiments, the dextrose/lysine solution in the sterilized vessel may be kept at a temperature of about 19° C., about 19° C. or less, about 18° C. to about 19° C., or about 18° C. to about 20° C. Under aseptic conditions, the filtered dextrose/lysine solution is added to the w/o emulsion in a volume ratio of approximately 2.5:1 at an emulsification step 109 using agitation to produce a water-in-oil-in-water emulsion (i.e., second emulsion).

At emulsification step 109, agitation is performed at lower shear, producing a water-in-oil-in-water (w/o/w) second emulsion with the majority of the bupivacaine resident in the internal aqueous phase. In some embodiments, the volume of this second emulsion can be from about 700 L to about 860 L. Additional filtered dextrose/lysine solution is added to the w/o emulsion at a dilution step 110 to form a diluted water-in-oil-in-water emulsion of MVLs and bringing the final volume ratio to approximately 20:1 (dextrose/lysine solution to water-in-oil emulsion) with mixing. In some embodiments, the volume of the diluted water-in-oil-in-water second emulsion can be from about 4000 L to about 5200 L or from about 4200 L to about 5040 L. The diluted w/o/w second emulsion can have a temperature of from about 18° C. to about 22° C. In some embodiments, the diluted w/o/w second emulsion can have a temperature of about 19° C., about 19° C. or less, about 18° C. to about 19° C., or about 18° C. and about 20° C. (e.g., due to the temperature of the dextrose/lysine solution).

At a step 111, the diluted water-in-oil-in-water emulsion of MVLs is sparged with sterile nitrogen to remove at least a portion of the methylene chloride. In some embodiments, the sparge gas flow rate, liquid temperature, and dimensions of the sparge vessel have been found to impact the sparging process. In some embodiments, the duration of sparge, size and number of sparge tubes, vessel heating capacity, number of sparge holes, size of sparge holes, and location of sparge tubes have been found to impact the sparging process. In some embodiments, the sparge vessel comprises a vertical cylindrical vessel with a diameter to height ratio of about 0.6, 0.7, 0.8, 0.9 or 1.0, or any ratio therebetween. In some embodiments, the diameter to height ratio is about 0.8. This relatively taller and reduced diameter sparge vessel (as compared to the vessel used in the UK 200 L process) results in increased sparge efficiency for substantially removing methylene chloride. In some embodiments, the relatively taller and reduced diameter sparge vessel in combination with the number and location of sparge tubes results in increased sparge efficiency for substantially removing methylene chloride. In some embodiments, sparging comprises bubbling nitrogen through the diluted emulsion at sparge gas flow rate of about 1874 SLPM (standard liters per minute) to about 2500 SLPM. In some embodiments, the sparge gas flow rate can be about 2400 SLPM.

In some embodiments, sparging is performed for about 19 minutes to about 25 minutes. In some embodiments, sparging is performed for about 19 minutes, about 20 minutes, about 21 minutes, about 22 minutes, about 23 minutes, about 24 minutes, about 25 minutes, or any value therebetween. In some embodiments, sparging is performed for about 22 minutes. If sparging is not performed for a sufficiently long period of time, too much volatile solvent may remain in the diluted w/o/w emulsion of MVLs. If sparging is performed for too long of a period of time, excess MVL breakage can occur. In some embodiments, excess MVL breakage can hurt the product yield. In some embodiments, excess MVL breakage can cause an excessive pH decrease, which may result in bupivacaine in the second aqueous solution to crystalize and cause batch manufacture failure. In some embodiments, pH may be monitored to determine when sparging is complete. In some embodiments, conductivity values can be monitored to determine when sparging is complete.

It was observed that in some embodiments, a lower sparge gas flow rate such as 1874 SLPM with a longer sparge time such as 25 minutes, or a higher sparge gas flow rate such as 2500 SLPM with a shorter sparge time such as 20 minutes, can each be sufficiently effective at substantially removing methylene chloride. Between the two approaches, the higher sparge gas flow rate and shorter sparge time approach was observed to result in improved product yield, increasing production capacity for bupivacaine encapsulated MVLs (e.g., due to reduced bupivacaine encapsulated MVL destruction during sparging).

In certain embodiments, it has been found that sparging at a lower temperature (e.g., a temperature of about 19° C., about 19° C. or less, about 18° C. to about 19° C., or about 18° C. to about 20° C.) is effective at increasing yield in comparison to a higher temperature. In some embodiments, the temperature of the diluted second emulsion during the sparge process is about 19° C. In some embodiments, the second aqueous solution is supplied and/or maintained at a lower temperature such that the diluted second emulsion is at the lower temperature. In some embodiments, the second aqueous solution is supplied and/or maintained at a temperature of about 19° C., about 19° C. or less, about 18° C. to about 19° C., or about 18° C. to about 20° C.

Sparging the diluted emulsion to remove at least a portion of the methylene chloride forms a first aqueous suspension of bupivacaine encapsulated MVLs having a first volume. In some embodiments, the first volume can be about 4000 L to about 5000 L.

As descried herein, in some embodiments in which sparging is performed at lower temperatures (e.g., about 19° C., about 19° C. or less, about 18° C. and about 19° C., or about 18° C. to about 20° C.), higher shear mixing speeds can be used at step 109, such as shear mixing speeds of about 520 rpm, at least about 520 rpm, about 535 rpm, at least about 535 rpm, about 575 rpm, at least about 575 rpm, about 630 rpm, at least about 630 rpm or from 520 rpm to about 680 rpm.

First Microfiltration

FIG. 1B depicts additional steps of the process 100. After sparging at step 111, the diluted suspension of bupivacaine MVLs is concentrated via aseptic microfiltration at a step 112. In some embodiments, the diluted suspension is concentrated to a bupivacaine concentration of about 4.0 mg/mL to about 6.7 mg/mL or approximately 4.5 mg/mL. This first microfiltration reduces the first volume of the first aqueous suspension to form a second aqueous suspension having a second volume. In some embodiments, the second volume includes about 200 L to 480 L in the sparge vessel, as well as about 400 L to about 550 L in the tangential flow filtration (TFF) filters and the connecting piping to the sparge vessel. In some embodiments, the first volume is reduced by about 75%-90%.

In some embodiments, the first microfiltration comprises circulating the first aqueous suspension past at least one tangential flow filter, thereby reducing the first volume as a portion of the first aqueous suspension that is less than a membrane pore size (e.g., less than about 0.2 microns) of the tangential flow filter(s) passes through the tangential flow filter(s) as permeate, and a portion not removed as permeate is recirculated. The tangential flow filter(s) can be arranged in tangential flow filtration modules, as described with respect to FIG. 2 below. It was observed that increasing the feed flow rate of the first aqueous suspension during this first microfiltration can provide smaller particle size distribution of MVLs in the final product. The feed flow rate of the first microfiltration is summed across the input streams of all filter modules to describe a total first microfiltration feed flow rate. In some embodiments, as described herein, the total first microfiltration feed flow rate can be about 190 L/min to about 350 L/min or about 250 L/min to about 350 L/min per TFF array.

As described herein, in some embodiments, the feed flow rate of the first microfiltration decreases (e.g., linearly or approximately linearly) between the start and end of the first microfiltration in relation to the level of liquid in the sparging vessel or the bupivacaine MVLs concentration in the aqueous suspension. In some embodiments, the total first microfiltration feed flow rate can be about 340 L/min or about 290 L/min to about 350 L/min at the start of microfiltration for each TFF array. In some embodiments, the total first microfiltration feed flow rate can be about 300 L/min or from about 250 L/min to about 310 L/min per TFF array. As described in any embodiments of the present disclosure, the feed flow rate of the first microfiltration step refers to the total feed flow rate per TFF array.

Diafiltration

At a step 113, a NaCl solution is formed by dissolving sodium chloride in WFI. At a step 114, the NaCl solution (i.e., saline solution) is filtered through a 0.2 µm membrane filter.

Under aseptic conditions, the bupivacaine MVLs concentrate (second aqueous suspension) formed at step 112 is subjected to diafiltration in step 115. In some embodiments, diafiltration crossflow filtration by at least four volumes or at least 4.5 volumes of the filtered NaCl solution through introduction of the filtered NaCl solution into a filtration apparatus or system through multiple 0.2 µm hollow fiber filter membrane unit filters at a diafiltration step 115. Diafiltration step 115 is used to remove unencapsulated bupivacaine, lysine, dextrose and residual methylene chloride. This diafiltration step exchanges a portion of the second aqueous suspension that is less than a membrane pore size (e.g., less than about 0.2 microns) of the tangential flow filter(s) with a saline solution to provide a third aqueous suspension of bupivacaine encapsulated MVLs having a third volume. In some embodiments, the third volume can be about 675 L to about 945 L.

It was observed that increasing the feed flow rate of the second aqueous suspension during diafiltration can lower the particle size distribution of MVLs in the final product. The feed flow rate of the diafiltration process is summed across the input streams of each array of filters (e.g., six filters/array) to describe a total diafiltration feed flow rate. In some embodiments, the total diafiltration feed flow rate is about 190 L/min to about 310 L/min for each TFF array.

In some embodiments, the diafiltration is performed at at least two stages comprising an initial stage and a later stage. The initial stage may comprise a higher total diafiltration feed flow rate than the later stage. In some embodiments, the diafiltration process may begin with the initial stage, then continues with the initial stage until it begins the later stage, then continues with the later stage until the diafiltration is complete. The total diafiltration feed flow rate can be described for these two stages as an initial stage total diafiltration feed flow rate and a later stage total diafiltration feed flow rate.

In some embodiments, an initial or first stage total diafiltration feed flow rate is about 190 L/min to about 310 L/min for each TFF array. In some embodiments, the initial stage total diafiltration flow rate is about 300 L/min per TFF array. In some embodiments, the later or second stage total diafiltration feed flow rate is about 190 L/min to about 265 L/min per TFF array. In some embodiments, the later stage total diafiltration feed flow rate is about 255 L/min per TFF array. As described in any embodiments of the present disclosure, the feed flow rate of the diafiltration step refers to the total feed flow rate per TFF array.

At a step 116, sterile nitrogen is used to flush the headspace of the crossflow filtration apparatus or system to further reduce residual methylene chloride content and final product pH. In some embodiments, step 116 can be performed in parallel with step 115.

Second Microfiltration

At step 117, the third aqueous suspension is subjected to a second microfiltration, reducing the third volume of the third aqueous suspension and providing a final aqueous suspension of bupivacaine encapsulated MVLs having a target concentration. In some embodiments, the solution is concentrated via aseptic microfiltration in concentrate step 117 to form an initial bulk suspension of MVLs at a target weight/volume that corresponds to a bupivacaine concentration of 12.3-16.6 mg/mL.

In some embodiments, the second microfiltration comprises circulating the third aqueous suspension past at least one tangential flow filter, thereby reducing the third volume as a portion of the third aqueous suspension that is less than a membrane pore size (e.g., less than about 0.2 microns) of the tangential flow filter(s) passes through the tangential flow filter(s) as permeate, and a portion not removed as permeate is recirculated. The tangential flow filter(s) can be arranged in tangential flow filtration modules, as described in the section below. The feed flow rate of the second microfiltration is summed across the input streams of all filter modules to describe a total second microfiltration feed flow rate. In some embodiments, the total second microfiltration feed flow rate is about 120 L/min to about 265 L/min for each TFF array.

As described herein, in some embodiments, the feed flow rate of the second microfiltration decreases (e.g., linearly or approximately linearly) between the start and end of the second microfiltration in relation to the level of liquid in the concentration vessel or the bupivacaine MVLs concentration in the aqueous suspension. In some embodiments, the total second microfiltration feed flow rate can be about 255 L/min or from about 190 L/min to about 265 L/min at the start of microfiltration per TFF array. In some embodiments, the total second microfiltration feed flow rate can be about 180 L/min or from about 120 L/min to about 190 L/min at the end of microfiltration per TFF array. As described in any embodiments of the present disclosure, the feed flow rate of the second microfiltration step refers to the total feed flow rate per TFF array.

The bulk product is then transferred into a sterilized holding vessel. The initial bulk suspension of MVLs is sampled and bupivacaine concentration is measured. In certain embodiments, the product yield can be about 75% to about 85%, where the product yield is calculated by dividing the total amount of bupivacaine in the bulk suspension of MVLs by a total amount of bupivacaine in the first emulsion vessel (exclude transfer hold up loss). In some embodiments, the product yield is at least about 75%, 76%, 77%, 78%, 79%, 80%, 81%, 82% or 83%.

Optionally, if the initial bulk suspension of MVLs is designated to be filled as an individual lot, the initial bulk suspension of MVLs is concentrated further via sedimentation (gravitational settling) and/or decantation to a bupivacaine concentration of approximately 13.3 mg/mL, or alternatively diluted with a filtered NaCl solution to a bupivacaine concentration of approximately 13.3 mg/mL at a decantation and/or dilution step 120 to form an adjusted bulk suspension of MVLs. The saline solution that is optionally used at step 120 can be formed by dissolving sodium chloride in WFI at a step 118 and filtered through a 0.2 μm membrane filter at a step 119.

Tangential Flow Filtration Modules

Some embodiments of the present application relates to a crossflow filtration system comprising: a diafiltration vessel; and a plurality of independently operating crossflow modules, each crossflow module of the plurality of independently operating crossflow modules comprising at least one filter array, each filter array comprising a plurality of hollow fiber filters, wherein each crossflow module of the plurality of independently operating crossflow modules is connected to a retentate conduit, a permeate conduit, and a rotary lobe pump. In some embodiments, the crossflow filtration system may be used in the microfiltration and/or diafiltration step of the commercial process described herein.

In some embodiments, each crossflow module comprises two filter arrays. In some embodiments, each crossflow module comprises at least five hollow fiber filters or at least six follow fiber filters. In some such embodiments, each filter array comprises at least two, three, four, five or six hollow fiber filters.

In some embodiments, the plurality of independently operating crossflow modules comprises a first crossflow module and a second crossflow module, wherein the first crossflow module is coupled to a first rotary lobe pump and the second crossflow module is coupled to a second rotary lobe pump operating independently of the first rotary lobe pump. In some further embodiments, the first crossflow module is coupled to the diafiltration vessel by a first retentate conduit to facilitate flow of retentate from the first crossflow module to the diafiltration vessel, and wherein the second crossflow module is coupled to the diafiltration vessel by a second retentate conduit to facilitate flow of retentate from the second crossflow module to the diafiltration vessel. In some further embodiments, the first rotary lobe pump comprises a fluid outlet coupling the first rotary lobe pump to the first crossflow module, and wherein the second rotary lobe pump comprises a fluid outlet coupling the second rotary lobe pump to the first crossflow module. In some further embodiments, the first rotary lobe pump comprises a fluid inlet coupling the first rotary lobe pump to the diafiltration vessel, and wherein the second rotary lobe pump comprises a fluid inlet coupling the second rotary lobe pump to the diafiltration vessel.

In some embodiments, the first crossflow module operates independently from the second crossflow module. In some such embodiments, only one of the first crossflow module and the second crossflow module is in use during the operation of the crossflow filtration system. In other embodiments, both the first crossflow module and the second crossflow module are in use during the operation of the crossflow filtration system.

In some embodiments, each of the plurality of independently operating crossflow modules comprises a microfiltration mode and a diafiltration mode.

In some embodiments, the crossflow filtration system further comprises a nitrogen flushing module to blow a stream nitrogen over the retentate in the diafiltration vessel.

Some further embodiments of the present application relate to a process of manufacturing bupivacaine encapsulated multivesicular liposomes using the crossflow module described herein, the process comprising:

reducing a first aqueous suspension of bupivacaine encapsulated MVLs having a first volume by microfiltration to provide a second aqueous suspension of bupivacaine encapsulated MVLs having a second volume;

exchanging a portion of the second aqueous suspension that is less than a membrane pore size (e.g., less than about 0.2 microns) of the tangential flow filter(s) with a saline solution by diafiltration to provide a third aqueous suspension of bupivacaine encapsulated MVLs having a third volume; and further reducing the third volume of the third aqueous suspension by microfiltration to provide a final aqueous suspension of bupivacaine encapsulated MVLs having a target concentration of bupivacaine.

In some embodiments, the process further comprises blowing a stream of nitrogen over the second aqueous suspension during the diafiltration/saline exchange step. In some further embodiments, the diafiltration include at least 3, 3.5, 4, 4.5, or 5 exchange volumes of the saline solution such that the aqueous supernatant of the second aqueous suspension is substantially (e.g., at least 95%, 96%, 97%, 98%, 99%) replaced by the saline solution. In some embodiments, the diafiltration includes 4.5 exchange volumes.

FIG. 2 depicts an embodiment of a system 200 including components for performing embodiments of a manufacturing process as described herein.

In certain embodiments, the system 200 can include a preparation vessel 220. In certain embodiments, the vessel 220 can be used for a lipid/drug solution formation step of a commercial scale manufacturing process as described herein, such as step 102 of the process 100. In certain embodiments, DEPC, DPPG, cholesterol, tricaprylin, WFI, bupivacaine, and methylene chloride added to the vessel 220 and mixed to form a lipid/drug solution within the vessel 220.

In certain embodiments, the system 200 can include a preparation vessel 222. In certain embodiments, the vessel 222 can be used in a first aqueous solution formation step of a commercial scale manufacturing process as described herein, such as step 104 of the process 100. In certain embodiments, phosphoric acid and WFI can be mixed within the preparation vessel 222 to form the first aqueous solution.

In certain embodiments, the system 200 can include an emulsification vessel 224. In certain embodiments, the vessel 224 can be used in a w/o emulsion step of a commercial scale manufacturing process as described herein, such as step 106 of the process 100. In certain embodiments, the lipid/drug solution from vessel 220 and the first aqueous solution from vessel 222 can be transferred to the emulsification vessel 224 and mixed to form a w/o first emulsion.

In certain embodiments, the system 200 can include a preparation vessel 226. In certain embodiments, the vessel 226 can be used in a dextrose/lysine solution formation step of a commercial scale manufacturing process as described herein, such as step 107 of the process 100. In certain embodiments, lysine, dextrose, and WFI can be added to the vessel 226 and mixed until dissolved to form a dextrose/lysine solution.

In certain embodiments, the system 200 can include a sparge/diafiltration vessel 228. In certain embodiments, the dextrose/lysine solution can be transferred to the vessel 228 after formation.

In certain embodiments, the vessel 224 can be used in a w/o/w second emulsion step of a commercial scale manufacturing process as described herein, such as step 109 of the process 100. In certain embodiments, a predetermined amount of the dextrose lysine solution can be transferred from the vessel 228 to the vessel 224 and mixed with the w/o emulsion to form a w/o/w emulsion within the vessel 224.

In certain embodiments, the vessel 228 can be used for a step of forming a diluted suspension of a commercial scale manufacturing process as described herein, such as step 110 of the process 100. In certain embodiments, the w/o/w emulsion from vessel 224 can be transferred to vessel 228 containing the remaining volume of the dextrose/lysine solution.

In certain embodiments, the vessel 228 can be used in a sparging step of a commercial scale manufacturing process as described herein, such as step 110 of the process 100. Sparging with nitrogen can then be performed in the vessel 228 to substantially remove methylene chloride to form a first aqueous suspension of bupivacaine encapsulated MVLs having a first volume.

In certain embodiments, the system 200 can include a crossflow filtration system 250 (tangential flow filter). The filtration system 250 can be used in microfiltration and/or diafiltration steps of a commercial scale manufacturing process as described herein, such as steps 115, 116, and/or 117 of the process 100.

In certain embodiments, the filtration system 250 can be used in a concentration step of a commercial scale manufacturing process as described herein, such as step 112 of the process 100. In certain embodiments, the crossflow filtration system 250 can be used in a microfiltration mode to reduce the total volume of the first aqueous suspension of bupivacaine encapsulated MVLs to form a second suspension of bupivacaine encapsulated MVLs having a second volume.

In certain embodiments, the vessel 226 can be used in a saline solution formation step of a commercial scale manufacturing process as described herein, such as step 113 of the process 100. In certain embodiments, sodium chloride and WFI can be added to the vessel 226 and mixed to form a saline solution.

In certain embodiments, the filtration system 250 can be used in a diafiltration step of a commercial scale manufacturing process as described herein, such as step 115 of the process 100. In certain embodiments, the crossflow filtration system 250 can be used in a diafiltration mode to undergo several volume exchanges with the saline solution to provide a third aqueous suspension of bupivacaine encapsulated MVLs having a third volume.

In certain embodiments, the filtration system 250 can be used in a nitrogen flushing step of a commercial scale manufacturing process as described herein, such as step 116 of the process 100. In certain embodiments, the head space of the crossflow filtration system 250 or portions thereof can be flushed with nitrogen to reduce pH and methylene chloride content during diafiltration.

In certain embodiments, the filtration system 250 can be used in a concentration step of a commercial scale manufacturing process as described herein, such as step 117 of the process 100. In certain embodiments, the crossflow filtration system 250 can be used in microfiltration mode to provide a final suspension of bupivacaine encapsulated multivesicular liposomes having a target concentration of bupivacaine.

In some embodiments, the system 200 can include a concentration vessel 230. In certain embodiments, the vessel 230 can be used in a concentration step of a commercial scale manufacturing process as described herein, such as step 117 of the process 100. In some embodiments, during this microfiltration, the dilute product can be transferred to the concentration vessel 230, where microfiltration can be continued until the volume is reduced to the target volume.

In certain embodiments, the system 200 can include a final product vessel 232 that can receive the final suspension after reduction to the target volume.

The filtration system 250 includes independently operating crossflow modules 202a and 202b. Crossflow module 202a includes a filter array 204a and a filter array 204b. Crossflow module 202b includes a filter array 204c and a filter array 204d. Each filter array 204a-d may include two or more hollow fiber filters. In some embodiments, each filter array includes five or more or six or more hollow fiber filters.

As shown in FIG. 2, the system may be connected to a sparge/diafiltration vessel 228. Retentate can flow from the crossflow module 202a to the vessel 228 via a retentate return conduit 208a. For example, the retentate return conduit 208a can be in fluid communication with both the filter array 204a and the filter array 204b (e.g., via a transfer panel) to receive retentate flowing therefrom. Retentate can flow from the crossflow module 202b to the vessel 228 via a retentate return conduit 208b. For example, the retentate return conduit 208b can be in fluid communication with both the filter array 204c and the filter array 204d (e.g., via a transfer panel) to receive retentate flowing therefrom. Similarly, retentate can flow from the crossflow module 202a to the concentration vessel 230 via the retentate return conduit 208a and retentate can flow from the crossflow module 202b to the concentration vessel 230 via the retentate return conduit 208b.

Permeate can flow from the crossflow module 202a for removal from the filtration system 250 via a permeate conduit 210a. For example, the permeate conduit 210a can be in fluid communication with both the filter array 204a and the filter array 204b (e.g., via a transfer panel) to receive permeate flowing therefrom. Permeate can flow from the crossflow module 202b for removal from the filtration system 250 via a permeate conduit 210b. For example, the permeate conduit 210b can be in fluid communication with both the filter array 204c and the filter array 204d (e.g., via a transfer panel) to receive permeate flowing therefrom.

The filtration system 250 may include or be used in conjunction with two independently operating rotary lobe pumps 212a and 212b. The pump 212a includes a fluid inlet 214a and a fluid outlet 216a. The pump 212b includes a fluid inlet 214b and a fluid outlet 216b. The pump 212a is connected to the vessel 228 via the inlet 214a and connected to crossflow module 202a via the outlet 216a. The pump 212b is connected to the vessel 228 via the inlet 214b and connected to the crossflow module 202b via the outlet 216b. The pump 212a is also connected to the vessel 230 via the inlet 214a. The pump 212b is connected to the vessel 230 via the inlet 214b.

In some embodiments of the processes described herein, the crossflow filtration system utilizes two independent rotary lobe pumps providing retentate flow to independent arrays of five or six hollow fiber filter housings. This configuration allows for smaller pipe diameters. Smaller pipe diameters can minimize the volume within the crossflow filtration system 250 to allow for concentration to the target volume. Smaller pipe diameters may also allow for cleaning using lower flow rates than higher pipe diameters. In addition, the filtration module design allows for two filter arrays to be in-use during bulk operation while two filter arrays are being cleaned and sterilized in preparation for the next bulk production run. This configuration allows for shorter cycle times and increased manufacturing capacity. Furthermore, the improved filtration module design allows for independent hollow fiber filter housing isolation. This functionality automatically detects and isolates individual filter integrity failures, allowing the bulk cycle to proceed without offline testing and recleaning. In some further embodiments, the process may further comprise an additional product recovery step from one of the two filter array and/or a saline flush step, to allow for nearly complete product recover from the transfer lines and thereby increasing product yield.

In some embodiments, the crossflow filtration system comprises at least one turbidity sensor disposed on a permeate outlet stream to monitor the turbidity of the stream. In some embodiments of the commercial-scale process described herein, a turbidity sensor disposed on a permeate outlet stream of a tangential flow filter is used to monitor the turbidity of the permeate. By sensing sudden changes in permeate turbidity, the turbidity sensor can be used to detect tangential flow filter breakthroughs during microfiltration and diafiltration steps. Should the turbidity change suddenly, the system can identify which filter is not integral and automatically turn off the permeate flow from the identified filter. Adding this capability to the commercial-scale process described herein can decrease the failure rate of bupivacaine encapsulated MVL batch failures, increasing production and allowing increased usage of the filters.

In some embodiments, a turbidity sensor can be positioned downstream of the filter array to detect when a filter has lost its integrity. The filter that has lost its integrity can be identified and automatically disqualified. This approach can reduce the risk of batch failure due to filter breakage. Sensing by this turbidity sensor for loss of filter integrity may be performed during microfiltration and/or diafiltration.

In some embodiments, the system comprises at least one inline mesh screen for filtering foreign debris. In some embodiments, an inline steel screen is used to filter foreign debris from MVL solutions or suspensions. In some embodiments, this screening step is performed when transferring the final aqueous suspension to a holding vessel after step (f), when transferring the final aqueous suspension from the holding vessel to an aseptic fill line, or any combination thereof. The mesh screen can be placed inline such that the process fluids flow through it during the process, catching foreign debris such as plastic from shedding gaskets from process equipment. Then, the inline mesh screen can be removed between batches or when cleaning to inspect for foreign debris and remove foreign debris enmeshed and/or replaced between batches.

In any embodiments of the processes described herein, the final aqueous suspension of bupivacaine encapsulated multivesicular liposomes produced by the process described herein has a volume of at least about 150 L. In one embodiment, the final aqueous suspension of bupivacaine encapsulated multivesicular liposomes has a volume of about 200 L to about 300 L, e.g., about 200, 210, 220, 230, 240, 250, 260, 270, 280, 290 or 300 L. In another embodiment, the final aqueous suspension of bupivacaine encapsulated multivesicular liposomes has a volume of about 225 L to about 300 L. In some such embodiments, the target concentration of the bupivacaine in the final aqueous suspension (i.e., bulk product suspension) is from about 12 mg/mL to about 17 mg/mL, or from about 12.3 mg/mL to about 16.6 mg/mL. In further embodiments, the final product target concentration of the bupivacaine in the aqueous suspension is about 13.3 mg/mL. In some embodiments, the percent packed particle volume (% PPV) of the bupivacaine encapsulated MVLs in the composition is about 32% to about 44% (e.g., about 35%, 36%, 37%, 38%, 39% or 40%). In some embodiments, the final aqueous suspension of bupivacaine MVLs comprises less than 5%, 4%, 3%, 2% or 1% unencapsulatedbupivacaine, wherein the amount of unencapsulated bupivacaine is calculate based on the total weight of the bupivacaine in the aqueous suspension. In some embodiments, the volume weighted $d_{50}$ of the multivesicular liposomes in the final aqueous suspension is about 24 m to about 28 m. In some embodiments, the $d_{50}$ of the multivesicular liposomes in the final aqueous suspension is about 25 m, about 26 m or about 27 m. In some embodiments, the volume weighted $d_{10}$ of the multivesicular liposomes in the final aqueous suspension is about 13 m to about 15 m, or about 13.5 μm to about 14.5 μm. In some embodiments, the volume weighted $d_{90}$ of the multivesicular liposomes in the final aqueous suspension is about 46 m to about 57 μm, about 47 μm to about 54 μm, or about 48 μm to about 52 μm.

Bupivacaine In Vitro Release Assay (IVRA) Test

Topologically, multivesicular liposomes are defined as having multiple non-concentric chambers within each particle, resembling a “foam-like” or “honeycomb-like” matrix. The individual chambers are separated by lipid bilayer membranes composed of synthetic and naturally occurring lipids. The presence of internal membranes distributed as a network throughout multivesicular liposomes may serve to confer increased mechanical strength to the vesicle. The multivesicular nature of multivesicular liposomes also indicates that, unlike for unilamellar vesicles, a single breach in the external membrane of multivesicular vesicles will not result in total release of the internal aqueous contents. Exparel® has an extended release profile of bupivacaine up to 72 hours. The Exparel® product specification requires that the average cumulative percentage release of bupivacaine is 10%-35% at 4-hour, 46%-71% at 24-hour, 60%-85% at 48-hour, and no less than 80% at 168-hour, using a rotator-facilitated test also referred to as in vitro release assay (IVRA) test.

The IVRA test is based on mechanical disruption of MVL particles via physical impact of mixing in the presence of an air bubble of a specific size. An aliquot of a batch of bupivacaine MVLs prepared by the process described herein is diluted 17-fold in a media containing 0.5% bovine serum albumin (BSA)/50 mM pH 7 phosphate buffered saline (PBS) and 0.05% sodium azide. Then, 1.8 mL of the diluted bupivacaine MVLs composition is transferred to a 2 mL Simport polypropylene microcentrifuge tube, or 1.94 mL of the diluted bupivacaine MVLs composition is transferred to a 2 mL VWR crew-cap polypropylene microcentrifuge tube. For each aliquot, a set of five microcentrifuge tubes are used for measurement at the five time points: 0 hour, 4-hour, 24-hour, 48-hour, and 168-hour. For each lot, six aliquots of bupivacaine MVLs are used to calculate the cumulative percentage release of bupivacaine at each time points (i.e., an average of each aliquots). These tubes are rotated at 37° C. at a speed of 12 rpm. The tubes are rotated for 168 hours and sampled at the 4-hour, 24-hour, 48-hour, and 168-hour time points. At each time point, six sample tubes are removed and tested for bupivacaine content in the supernatant; the sample tubes are centrifuged at 14,000 g for 10 minutes. Without disturbing the MVL pellet, 350 µL of the supernatant is pipetted into a 1.5 mL tube, combined with 700 µL acetonitrile and vortexed at high speed for 10 seconds, then the 1.5 mL tube is incubated at room temperature for 30 minutes to precipitate BSA/lipids. Then about 700 µL of supernatant from each 1.5 mL tube is transferred into a HPLC vial for analysis. The bupivacaine in the supernatant (released from the MVL particles) is determined by isocratic reversed-phase HPLC (column: C18, 5 µm, 3.0 mm×150 mm, Zorbax Extend) with UV detection at 263 nm, using bupivacaine HCl as reference standard (about 0.1 mg/mL in 40% IPA). The flow rate is 0.7 mL/min, and the injection volume is 10 µL. The mobile phase is composed of 65% Acetonitrile: 35% Phosphate Buffer (pH 6.8). The pH of the mobile phase is 7.7±0.2.

Percent release is determined from the bupivacaine concentration in the supernatant and the labeled concentration of bupivacaine in the product (which is 13.3 mg/mL). The data is presented as a cumulative percentage release of bupivacaine against time. All of the six individual replicate bupivacaine percentage released results for each sample must be not more than 10% outside the specification window for t=4-hour, 24-hour and 48-hour time points (e.g., the individual % released results should be from 36% to 81% at the 24-hour time point from 50% to 95% at the 48-hour time point). The six individual replicate % released results must be not more than 10% below the specification limit for t=168-hour (i.e. the individual % released results must be no less than 70%.).

Bupivacaine Multivesicular Liposomes

Some embodiments of the present disclosure relate to batches comprising compositions of bupivacaine encapsulated multivesicular liposomes (MVLs), the composition comprising:
bupivacaine residing inside a plurality of internal aqueous chambers of MVLs separated by lipid membranes, wherein the lipid membranes comprise DEPC, DPPG or a salt thereof, cholesterol, and tricaprylin; and
an aqueous medium in which the bupivacaine encapsulated MVLs are suspended, wherein the aqueous medium also comprises unencapsulated bupivacaine; and
the total bupivacaine concentration in the composition is from 12 mg/mL to 17 mg/mL;
wherein the batches are manufactured within a period of six months, and the batches each has a volume of at least 100 liters;
wherein each batch has a cumulative percentage release of bupivacaine from 46% to 71% at a 24-hour time point, measured from two or more aliquots of each batch using a rotator-facilitated in vitro release assay, after storage of the aliquots of each batch at 2° C. to 8° C. for about 12 months from batch manufacture date; and
wherein an average rate of change in the cumulative percentage release of bupivacaine of the batches at the 24-hour time point is at least 0.05%/month after storage of the aliquots of each batch at 2° C. to 8° C. for about 12 months. In some further embodiments, the average rate of change in the cumulative percentage release of bupivacaine at the 24-hour time point is, or is at least 0.06%/month, 0.07%/month, 0.08%/month, 0.09%/month, 0.10%/month, 0.11%/month, 0.12%/month, 0.13%/month, 0.14%/month, 0.15%/month, 0.16%/month, 0.17%/month, 0.18%/month, 0.19%/month, or 0.20%/month, or a range defined by any two of the preceding values, after storage of the aliquots of each batch at 2° C. to 8° C. for about 12 months. In some further embodiments, the average rate of change in the cumulative percentage release of bupivacaine at the 24-hour time point is at least 0.08%/month. In some embodiments, the average rate of change in the cumulative percentage release of bupivacaine at the 24-hour time point is 0.1%/month to 0.5%/month, for example, 0.15%/month to 0.45%/month, 0.20%/month to 0.40%/month, or 0.25%/month to 0.35%/month. In some further embodiments, the IVRA test is performed for at least 48 hours, and each batch has a cumulative percentage release of bupivacaine from 60% to 85% at the 48-hour time point, and the average rate of change in the cumulative percentage release of bupivacaine at the 48-hour time point is no less than −0.3%/month after storage of the aliquot of each batch at 2° C. to 8° C. for about 12 months. For example, the average rate of change in the cumulative percentage release of bupivacaine at the 48-hour time point is no less than −0.2%/month, for example, from −0.18%/month to 0.33%/month, −0.15%/month to 0.30%/month, −0.12%/month to 0.28%/month, −0.10%/month to 0.25%/month, −0.08%/month to 0.22%/month, −0.05%/month to 0.20%/month, or 0%/month to 0.15%/month.

Some embodiments of the present disclosure relate to batches comprising compositions of bupivacaine encapsulated multivesicular liposomes (MVLs), the composition comprising:
bupivacaine residing inside a plurality of internal aqueous chambers of MVLs separated by lipid membranes, wherein the lipid membranes comprise DEPC, DPPG or a salt thereof, cholesterol, and tricaprylin; and
an aqueous medium in which the bupivacaine encapsulated MVLs are suspended, wherein the aqueous medium also comprises unencapsulated bupivacaine; and
the total bupivacaine concentration in the composition is from 12 mg/mL to 17 mg/mL;
wherein the batches are manufactured within a period of six months, and the batches each has a volume of at least 100 liters;
wherein each batch has a cumulative percentage release of bupivacaine from 60% to 85% at a 48-hour time point, measured from two or more aliquots of each batch using a rotator-facilitated in vitro release assay, after storage of the aliquots of each batch at 2° C. to 8° C. for about 12 months from batch manufacture date; and
wherein an average rate of change in the cumulative percentage release of bupivacaine of the batches at the 48-hour time point is no less than −0.3%/month after storage of the aliquots of each batch at 2° C. to 8° C. for about 12 months. In some further embodiments, the average rate of change in the cumulative percentage release of bupivacaine at the 48-hour time point is, is no less than, or is at least −0.25%/month, −0.20%/month, −0.18%/month, −0.15%/month, −0.12%/month, −0.10%/month, −0.08%/month, −0.05%/month, no change (0%/month), 0.02%/month, 0.05%/month, 0.08%/month, 0.10%/month, 0.12%/month, 0.15%/month, 0.18%/month, 0.20%/month, 0.22%/month, or 0.25%/month, or a range defined by any two of the preceding values, after storage of the aliquots of each batch at 2° C. to 8° C. for about 12 months. In some further embodiments, the average rate of change in the cumulative percentage release of bupivacaine at the 48-hour time point is no less than −0.2%/month. In some further embodiments, the average rate of change in the cumulative percentage release of bupivacaine at the 48-hour time point is from −0.18%/month to 0.33%/month, for example, −0.15%/month to 0.30%/month, −0.12%/month to 0.28%/month, −0.10%/month to 0.25%/month, −0.08%/month to 0.22%/month, −0.05%/month to 0.20%/month, or 0%/month to 0.15%/month.

In some embodiments of the batches described herein, the average rate of change in the cumulative percentage release of bupivacaine is based on three batches, and one batch is manufactured at least 7 days apart (e.g., 7, 8, 9, or 10 or more days apart) from at least one other batch. In some other embodiments, the average rate of change in the cumulative percentage release of bupivacaine is based on two batches, and one batch is manufactured at least 7 days apart (e.g., 7, 8, 9, or 10 or more days apart) from the other batch. In some embodiments, the cumulative percentage release of bupivacaine of each batch is measured as the average of two aliquots, three aliquots, four aliquots, five aliquots, or six aliquots from each batch. In further embodiments, the cumulative percentage release of bupivacaine of each batch is measured as the average of six aliquots from each batch.

Some embodiments the present disclosure relate to batches comprising compositions of bupivacaine encapsulated MVLs, the composition comprising:

bupivacaine residing inside a plurality of internal aqueous chambers of MVLs separated by lipid membranes, wherein the lipid membranes comprise DEPC, DPPG or a salt thereof, cholesterol, and tricaprylin; and an aqueous medium in which the bupivacaine encapsulated MVLs are suspended, wherein the aqueous medium also comprises unencapsulated bupivacaine; and the total bupivacaine concentration in the composition is from 12 mg/mL to 17 mg/mL;

wherein the batches are manufactured within a period of six months, and the batches each has a volume of at least 100 liters;

wherein each batch has a cumulative percentage release of bupivacaine from 46% to 71% at a 24-hour time point, measured from two or more aliquots of each batch using a rotator-facilitated in vitro release assay, after storage of the aliquots of each batch at 2° C. to 8° C. for about 12 months from batch manufacture date; and wherein an average change in the cumulative percentage release of bupivacaine at the 24-hour time point is at least 0.5% after storage of the aliquots of each batch at 2° C. to 8° C. for about 12 months. In some further embodiments, the average change in the cumulative percentage release of bupivacaine at the 24-hour time point is or is at least 0.6%, 0.7%, 0.8%, 0.9%, 1.0%, 1.1%, 1.2%, 1.3%, 1.4%, 1.5%, 1.6%, 1.7%, 1.8%, 1.9% or 2.0% after storage of the aliquots of each batch at 2° C. to about 8° C. for 12 months. In some embodiments, the average change in the cumulative percentage release of bupivacaine at the 24-hour time point is at least 1%. In some further embodiments, the average change in the cumulative percentage release of bupivacaine at the 24-hour time point is 1% to 5%, for example, 1.5% to 4.5%, 2.0% to 4.0%, or 2.5% to 3.5%. In some further embodiments, the IVRA test is performed for at least 48 hours, and each batch has a cumulative percentage release of bupivacaine from 60% to 85% at the 48-hour time point, and an average change in the cumulative percentage release of bupivacaine at the 48-hour time point is no less than −5% after storage of the aliquots of each batch at 2° C. to 8° C. for about 12 months. In some embodiments, the average change in the cumulative percentage release of bupivacaine at the 48-hour time point is no less than −4%. In some further embodiments, the average change in the cumulative percentage release of bupivacaine at the 48-hour time point is from −4% to 6%, for example, −3.5% to 5.5%, −3.0% to 5.0%, −2.5% to 4.5%, −2.0% to 4.0%, −1.5% to 3.5%, or −1.0% to 3.0%.

Some embodiments the present disclosure relate to batches comprising compositions of bupivacaine encapsulated MVLs, the composition comprising:

bupivacaine residing inside a plurality of internal aqueous chambers of MVLs separated by lipid membranes, wherein the lipid membranes comprise DEPC, DPPG or a salt thereof, cholesterol, and tricaprylin; and an aqueous medium in which the bupivacaine encapsulated MVLs are suspended, wherein the aqueous medium also comprises unencapsulated bupivacaine; and the total bupivacaine concentration in the composition is from 12 mg/mL to 17 mg/mL;

wherein the batches are manufactured within a period of six months, and the batches each has a volume of at least 100 liters;

wherein each batch has a cumulative percentage release of bupivacaine from 60% to 85% at a 48-hour time point, measured from two or more aliquots of each batch using a rotator-facilitated in vitro release assay, after storage of the aliquots of each batch at 2° C. to 8° C. for about 12 months from batch manufacture date; and wherein an average change in the cumulative percentage release of bupivacaine at the 48-hour time point is no less than −5% after storage of the aliquots of each batch at 2° C. to 8° C. for about 12 months. In some embodiments, In some further embodiments, the average change in the cumulative percentage release of bupivacaine at the 48-hour time point is, or is no less than −4.5%, −4.0%, −3.5%, −3.0%, −2.5%, −2.0%, −1.5%, −1.0%, −0.5%, no change (0%), 0.5%, 1.0%, 1.5%, 2.0% or 2.5% after storage of the aliquots of each batch at 2° C. to about 8° C. for 12 months. In some embodiments, the average change in the cumulative percentage release of bupivacaine at the 48-hour time point is no less than −4%. In some further embodiments, the average change in the cumulative percentage release of bupivacaine at the 48-hour time point is from −4% to 6%, for example, −3.5% to 5.5%, −3.0% to 5.0%, −2.5% to 4.5%, −2.0% to 4.0%, −1.5% to 3.5%, or −1.0% to 3.0%.

In some embodiments of the batches described herein, the average change in the cumulative percentage release of bupivacaine is based on three batches, and one batch is manufactured at least 7 days apart (e.g., 7, 8, 9, or 10 or more days apart) from at least one other batch. In some other embodiments, the average change in the cumulative percentage release of bupivacaine is based on two batches, and one batch is manufactured at least 7 days apart (e.g., 7, 8, 9, or 10 or more days apart) from the other batch. In some embodiments, the cumulative percentage release of bupivacaine of each batch is measured as the average of two aliquots, three aliquots, four aliquots, five aliquots, or six aliquots from each batch. In some further embodiments, the cumulative percentage release of bupivacaine of each batch is measured as the average of six aliquots from each batch.

In some embodiments of batches described herein, the batches each has a volume of at least 100 liters, 125 liters, 150 liters, 175 liters, 200 liters, 225 liters, 250 liters, 275 liters or 300 liters. In some further embodiments, the batches are manufactured within a period of 3 months. In some other embodiments, the batches are manufactured within a period of 2 months. In some embodiments, the batches are manufactured within a period of 30 days. In some embodiments, the batches are manufactured within a period of 3 months, each having a volume of at least 200 liters. In some embodiments, the batches are manufactured within a period of 2 months, each having a volume of at least 200 liters. In some embodiments, the batches are manufactured within a period of 30 days, each having a volume of at least 200 liters.

Some further embodiments of the present disclosure relate to batches comprising compositions of bupivacaine encapsulated MVLs, the composition comprising:
  bupivacaine residing inside a plurality of internal aqueous chambers of MVLs separated by lipid membranes, wherein the lipid membranes comprise DEPC, DPPG or a salt thereof, cholesterol, and tricaprylin; and
  an aqueous medium in which the bupivacaine encapsulated MVLs are suspended, wherein the aqueous medium also comprises unencapsulated bupivacaine; and
  the total bupivacaine concentration in the composition is from 12 mg/mL to 17 mg/mL;
  wherein the batches are manufactured within a period of three months, and the batches each has a volume of at least 100 liters;
  wherein each batch has a cumulative percentage release of bupivacaine from 46% to 71% at a 24-hour time point, measured from six aliquots of each batch using a rotator-facilitated in vitro release assay for at least about 48 hours, after storage of the aliquots of each batch at 2° C. to 8° C. for about 12 months from batch manufacture date;
  wherein the average rate of change in the cumulative percentage release of bupivacaine at the 24-hour time point is at least 0.05%/month after storage of the aliquots of each batch at 2° C. to 8° C. for about 12 months, and
  wherein the average rate of change in the cumulative percentage release of bupivacaine is based on two to five batches, and at least one batch is manufactured 10 or more days apart from at least one other batch. In some further embodiments, the average rate of change in the cumulative percentage release of bupivacaine at the 24-hour time point is or is at least 0.06%/month, 0.07%/month, 0.08%/month, 0.09%/month, 0.10%/month, 0.11%/month, 0.12%/month, 0.13%/month, 0.14%/month, 0.15%/month, 0.16%/month, 0.17%/month, 0.18%/month, 0.19%/month, or 0.20%/month after storage of the aliquots of each batch at 2° C. to 8° C. for about 12 months. In some embodiments, the average rate of change in the cumulative percentage release of bupivacaine at the 24-hour time point is at least 0.1%/month. In some further embodiments, the average rate of change in the cumulative percentage release of bupivacaine at the 24-hour time point is 0.15%/month to 0.5%/month, for example, 0.15%/month to 0.45%/month, 0.20%/month to 0.40%/month, or 0.25%/month to 0.35%/month. In some embodiments, the average rate of change in the cumulative percentage release of bupivacaine is based on three batches, and one batch is manufactured 10 or more days (e.g., 10, 15, 20, 25 or 30 days) apart from at least one other batch. In some other embodiments, the average rate of change in the cumulative percentage release of bupivacaine is based on two batches, and one batch is manufactured 10 or more days (e.g., 10, 15, 20, 25 or 30 days) apart from the other batch. In some further embodiments, the batches are manufactured within 30 days.

Some further embodiments of the present disclosure relate to batches comprising compositions of bupivacaine encapsulated MVLs, the composition comprising:
  bupivacaine residing inside a plurality of internal aqueous chambers of MVLs separated by lipid membranes, wherein the lipid membranes comprise DEPC, DPPG or a salt thereof, cholesterol, and tricaprylin; and
  an aqueous medium in which the bupivacaine encapsulated MVLs are suspended, wherein the aqueous medium also comprises unencapsulated bupivacaine; and
  the total bupivacaine concentration in the composition is from 12 mg/mL to 17 mg/mL;
  wherein the batches are manufactured within a period of three months, and the batches each has a volume of at least 100 liters;
  wherein each batch has a cumulative percentage release of bupivacaine from 60% to 85% at a 48-hour time point, measured from six aliquots of each batch using a rotator-facilitated in vitro release assay for at least about 48 hours, after storage of the aliquots of each batch at 2° C. to 8° C. for about 12 months from batch manufacture date;
  wherein the average rate of change in the cumulative percentage release of bupivacaine at the 48-hour time point is no less than −0.3%/month after storage of the aliquots of each batch at 2° C. to 8° C. for about 12 months, and
  wherein the average rate of change in the cumulative percentage release of bupivacaine is based on two to five batches, and at least one batch is manufactured 10 or more days apart from at least one other batch. In some embodiments, the average rate of change in the cumulative percentage release of bupivacaine at the 48-hour time point is, is no less than, or is at least −0.25%/month, −0.20%/month, −0.18%/month, −0.15%/month, −0.12%/month, −0.10%/month, −0.08%/month, −0.05%/month, no change (0%/month), 0.02%/month, 0.05%/month, 0.08%/month, 0.10%/month, 0.12%/month, 0.15%/month, 0.18%/month, 0.20%/month, 0.22%/month, or 0.25%/month, or a range defined by any two of the preceding values. In some embodiments, the average rate of change in the cumulative percentage release of bupivacaine at the 48-hour time point is no less than −0.2%/month. In some further embodiments, the average rate of change in the cumulative percentage release of bupivacaine at the 48-hour time point is from −0.18%/month to 0.33%/month, for example, −0.15%/month to 0.30%/month, −0.12%/month to 0.28%/month, −0.10%/month to 0.25%/month, −0.08%/month to 0.22%/month, −0.05%/month to 0.20%/month, or 0%/month to 0.15%/month. In some embodiments, the average rate of change in the cumulative percentage release of bupivacaine is based on three batches, and one batch is manufactured 10 or more days (e.g., 10, 15, 20, 25 or 30 days) apart from at least one other batch. In some other embodiments, the average rate of change in the cumulative percentage release of bupivacaine is based on two batches, and one batch is manufactured 10 or more days (e.g., 10, 15, 20, 25 or 30 days) apart from the other batch. In some further embodiments, the batches are manufactured within 30 days.

Additional embodiments of the present disclosure relate to batches comprising compositions of bupivacaine encapsulated MVLs, the composition comprising:

bupivacaine residing inside a plurality of internal aqueous chambers of MVLs separated by lipid membranes, wherein the lipid membranes comprise DEPC, DPPG or a salt thereof, cholesterol, and tricaprylin; and an aqueous medium in which the bupivacaine encapsulated MVLs are suspended, wherein the aqueous medium also comprises unencapsulated bupivacaine; and the total bupivacaine concentration in the composition is from 12 mg/mL to 17 mg/mL;

wherein the batches are manufactured within a period of three months, and the batches each has a volume of at least 100 liters;

wherein each batch has a cumulative percentage release of bupivacaine from 46% to 71% at a 24-hour time point, measured from six aliquots of each batch using a rotator-facilitated in vitro release assay for at least about 48 hours, after storage of the aliquots of each batch at 2° C. to 8° C. for about 12 months from batch manufacture date;

wherein an average change in the cumulative percentage release of bupivacaine at the 24-hour time point is at least 0.5% after storage of the aliquots of each batch at 2° C. to 8° C. for about 12 months; and wherein the average rate of change in the cumulative percentage release of bupivacaine is based on two to five batches, and at least one batch is manufactured 10 or more days apart from at least one other batch. In some further embodiments, the average change in the cumulative percentage release of bupivacaine at the 24-hour time point is or is at least 0.6%, 0.7%, 0.8%, 0.9%, 1.0%, 1.1%, 1.2%, 1.3%, 1.4%, 1.5%, 1.6%, 1.7%, 1.8%, 1.9% or 2.0% after storage of the aliquots of each batch at 2° C. to about 8° C. for 12 months. In some embodiments, the average change in the cumulative percentage release of bupivacaine at the 24-hour time point is at least 1%. In some further embodiments, the average change in the cumulative percentage release of bupivacaine at the 24-hour time point is 1% to 5%, for example, 1.5% to 4.5%, 2.0% to 4.0%, or 2.5% to 3.5%. In some embodiments, the average change in the cumulative percentage release of bupivacaine is based on three batches, and one batch is manufactured 10 or more days (e.g., 10, 15, 20, 25 or 30 days) apart from at least one other batch. In some other embodiments, the average change in the cumulative percentage release of bupivacaine is based on two batches, and one batch is manufactured 10 or more days (e.g., 10, 15, 20, 25 or 30 days) apart from the other batch. In some further embodiments, the batches are manufactured within 30 days.

Additional embodiments of the present disclosure relate to batches comprising compositions of bupivacaine encapsulated MVLs, the composition comprising:

bupivacaine residing inside a plurality of internal aqueous chambers of MVLs separated by lipid membranes, wherein the lipid membranes comprise DEPC, DPPG or a salt thereof, cholesterol, and tricaprylin; and an aqueous medium in which the bupivacaine encapsulated MVLs are suspended, wherein the aqueous medium also comprises unencapsulated bupivacaine; and the total bupivacaine concentration in the composition is from 12 mg/mL to 17 mg/mL;

wherein the batches are manufactured within a period of three months, and the batches each has a volume of at least 100 liters;

wherein each batch has a cumulative percentage release of bupivacaine from 60% to 85% at a 48-hour time point, measured from six aliquots of each batch using a rotator-facilitated in vitro release assay for at least about 48 hours, after storage of the aliquots of each batch at 2° C. to 8° C. for about 12 months from batch manufacture date;

wherein an average change in the cumulative percentage release of bupivacaine at the 48-hour time point is no less than −5% after storage of the aliquots of each batch at 2° C. to 8° C. for about 12 months; and wherein the average change in the cumulative percentage release of bupivacaine is based on two to five batches, and at least one batch is manufactured 10 or more days apart from at least one other batch. In some further embodiments, the average change in the cumulative percentage release of bupivacaine at the 48-hour time point is, or is no less than −4.5%, −4.0%, −3.5%, −3.0%, −2.5%, −2.0%, −1.5%, −1.0%, −0.5%, no change (0%), 0.5%, 1.0%, 1.5%, 2.0% or 2.5% after storage of the aliquots of each batch at 2° C. to about 8° C. for 12 months. In some embodiments, the average change in the cumulative percentage release of bupivacaine at the 48-hour time point is no less than −4%. In some further embodiments, the average change in the cumulative percentage release of bupivacaine at the 48-hour time point is from −4% to 6%, for example, −3.5% to 5.5%, −3.0% to 5.0%, −2.5% to 4.5%, −2.0% to 4.0%, −1.5% to 3.5%, or −1.0% to 3.0%. In some embodiments, the average change in the cumulative percentage release of bupivacaine is based on three batches, and one batch is manufactured 10 or more days (e.g., 10, 15, 20, 25 or 30 days) apart from at least one other batch. In some other embodiments, the average change in the cumulative percentage release of bupivacaine is based on two batches, and one batch is manufactured 10 or more days (e.g., 10, 15, 20, 25 or 30 days) apart from the other batch. In some further embodiments, the batches are manufactured within 30 days.

In some embodiments of batches described herein, the batches each has a volume of at least 100 liters, 125 liters, 150 liters, 175 liters, 200 liters, 225 liters, 250 liters, 275 liters, or 300 liters. In some embodiments, the batches are manufactured within a period of 2 months. In some embodiments, the batches are manufactured within a period of 30 days. In some embodiments, the batches are manufactured within a period of 2 months, each having a volume of at least 200 liters. In some embodiments, the batches are manufactured within a period of 1.5 months, each having a volume of at least 200 liters. In some embodiments, the batches are manufactured within a period of 30 days, each having a volume of at least 200 liters.

In any embodiments of the batch or batches described herein, the cumulative percentage release of bupivacaine is measured using the rotator-facilitated in vitro release assay for up to 168 hours. In some embodiments, the in vitro release assay is run for about 48 hours. In some other embodiments, the in vitro release assay is run for about 168 hours. In some embodiments, each aliquot has a cumulative percentage release of bupivacaine from 36% to 81% at the 24-hour time point. In some embodiments, each aliquot has a cumulative percentage release of bupivacaine from 50% to 95% at the 48-hour time point. In some embodiments, the cumulative percentage release of bupivacaine is measured after storage of the aliquots of each batch at about 5° C. for about 365 days from batch manufacture date.

In any embodiments of the batch or batches described herein, the total bupivacaine concentration in the composition is 12.0 to 14.6 mg/mL, or about 13.3 mg/mL. In some further embodiments, the % PPV of the bupivacaine encapsulated MVLs in the composition is about 32% to about 44%. In some embodiments, the shelf-life of the bupivacaine MVL product is at least 24 months (e.g., 24, 25, 26, 27, 28, 29 or 30 months). In some further embodiments, the aliquot of each batches is in a Type I clear glass vial with ETFE-faced gray butyl stopper and aluminum flip-off cap and polypropylene (PP) flip disc, or gray plug stopper and white aluminum flip tear up seal.

As described herein with respect to the any of the time points (e.g., 24-hour, 48-hour or 168-hour) in which cumulative percentage release of bupivacaine is tested, each time point is within ±15 minutes of the scheduled time points.

As described herein with respect to the rate of change in the cumulative percentage release of bupivacaine, each aliquot is measured at the following five time points: a first time point is within 30 days from batch manufacture date, a second time point is about 3 months from the batch manufacture date, a third time point which is about 6 months from the batch manufacture date, a fourth time point which is about 9 months from the batch manufacture date, and a fifth time point which is about 12 months from the batch manufacture date. Each time point of actual measurement is within ±30 days of the scheduled time point.

As described herein with respect to the change in the cumulative percentage release of bupivacaine after storage of the aliquots of each batch at 2° C. to 8° C. for about 12 months, the change is calculated as: % release of bupivacaine at about 12 months–% release of bupivacaine shortly after manufacturing (e.g., within 30 days from batch manufacture date when the batch product is filled into individual vials). Batch product is usually filled into individual vials within 7 days from manufacture date.

Some further embodiments relate to a composition of bupivacaine encapsulated multivesicular liposomes prepared by the process utilizing the crossflow filtration system described herein. In some embodiments, the bupivacaine concentration in the composition is about 12.0 mg/mL to about 14.6 mg/mL. In one embodiment, the bupivacaine concentration in the composition is about 13.3 mg/mL. In some embodiments, the percent packed particle volume (% PPV) of the composition of bupivacaine encapsulated MVLs is about 32%, 33%, 34%, 35%, 36%, 37%, 38%, 39%, 40%, 41%, 42%, 43% or 44%. In further embodiments, the % PPV of the bupivacaine MVLs is about 36% to about 38%. % PPV is calculated as 100%−(supernatant volume of the composition/total volume of the composition). In further embodiments, the composition comprises less than 5%, 4%, 3%, 2% or 1% unencapsulated bupivacaine, wherein the amount of unencapsulated bupivacaine is calculate based on the total weight of the bupivacaine in the composition. In some further embodiments, the bupivacaine encapsulated MVLs have an average/mean $d_{90}$ volume-weighted particle diameter less than about 54 m, 53 m or 52 m when measured shortly after manufacture (e.g., after storage of the composition at 2 to 8° C. for less than 1 week, 2 weeks, 3 weeks or 1 month). In further embodiments, the bupivacaine encapsulated MVLs have an average/mean volume-weighted particle diameter span ($d_{90}$–$d_{10}$) of less than about 38, 37, 36, 35, or 34 m when measured shortly after manufacture (e.g., after storage of the composition at 2 to 8° C. for less than 1 week, 2 weeks, 3 weeks or 1 month).

In some further embodiments, the composition of bupivacaine encapsulated MVLs may have a volume of 10 mL or 20 mL for a single dose administration. In any embodiments of the bupivacaine encapsulated MVLs described herein, the bupivacaine may be present in the salt form as bupivacaine phosphate.

Methodology

To determine total bupivacaine concentration, a sample of bupivacaine MVLs composition is dissolved/diluted 25-fold in 100% methanol, then analyzed by isocratic reversed-phase HPLC with UV detection at 263 nm. Bupivacaine concentration is determined on the basis of peak area, using an external bupivacaine hydrochloride standard.

To determine free bupivacaine (i.e., unencapsulated bupivacaine), a sample of freshly suspended bupivacaine MVLs composition is transferred to a microfuge tube which is centrifuged at 13,000 rpm in the Eppendorf microfuge model #5415) for 10 minutes at room temperature, then an aliquot of the supernatant diluted 5-fold in 100% methanol and the bupivacaine concentration assayed by HPLC. The volume fraction of external (i.e., extraliposomal) phase is assessed by placing a sample of bupivacaine MVLs composition in a capillary tube and centrifuging. The volume fraction of external phase is determined from the relative height of the supernatant compared to that of the total sample. Free bupivacaine (as a % of the total bupivacaine in the sample) is determined from the bupivacaine concentration in the supernatant and the volume fraction of external phase. The identity of bupivacaine is determined by comparing retention time of the bupivacaine peak in the sample with the bupivacaine hydrochloride reference standard peak.

To determine the particle size distribution of bupivacaine MVLs, a sample of bupivacaine MVLs suspension is diluted in 0.9% Sodium chloride (pH adjusted normal saline) and the particle size distribution is measured by laser light scattering (by HORIBA Laser Scattering Particle Size Distribution Analyzer LA-950 and LA-960 (or equivalent)), using Mie scattering theory. Three measurements are conducted for each sample.

Methods of Administration

Some embodiments of the present application are related to methods for treating, ameliorating pain comprising administering a pharmaceutical composition comprising bupivacaine MVLs as described herein, to a subject in need thereof. In some further embodiments, the pain is post-surgical pain.

In some embodiments of the methods described herein, the administration is parenteral. In some further embodiments, the parenteral administration may be selected from the group consisting of subcutaneous injection, tissue injection, intramuscular injection, intraarticular, spinal injection, intraocular injection, epidural injection, intrathecal injection, intraotic injection, perineural injection, and combinations thereof. In particular embodiments, the parenteral administration is subcutaneous injection or tissue injection. In some further embodiments, the instant pharmaceutical compositions can be administered by bolus injection, e.g., subcutaneous bolus injection, intramuscular bolus injection, intradermal bolus injection and the like. In one embodiment, the administration is via local infiltration to a surgical site to provide local analgesia. In another embodiment, the administration is via interscalene brachial plexus nerve block or femoral nerve block to provide regional analgesia. In another embodiment, the administration is via an adductor canal block to provide regional analgesia. In yet another embodiment, the administration is via a sciatic nerve block in the popliteal fossa to provide regional analgesia. For pediatric subjects between the age of 6 and 17 years old, the administration of bupivacaine MVL composition described herein may be weight based, at about 4 mg/kg and up to 233 mg of bupivacaine. In some embodiments, the bupivacaine MVL composition has a volume of 1 mL, 2 mL, 4 mL, 5 mL, 10 mL or 20 mL for a single-dose administration.

Administration of the instant bupivacaine MVL composition may be accomplished using standard methods and devices, e.g., pens, injector systems, needle and syringe, a subcutaneous injection port delivery system, catheters, and the like. The administration of the bupivacaine MVLs composition may be used in conjunction with Pacira's handheld cryoanalgesia device.

EXAMPLES

The following examples, including experiments and results achieved, are provided for illustrative purposes only and are not to be construed as limiting the present application.

Example 1. Sample Comparison—Average Rate of Change in Cumulative Percentage Release of Bupivacaine In this example, five batches (Batch Nos. 1-5) of Exparel® (bupivacaine MVLs) produced by the new process according to certain embodiment of the present disclosure were stored at 5° C. for about 12 months after batch manufacture date. An IVRA test was performed at 0 month, about 3 month, about 6 months, about 9 months and about 12 months. The average rate of change in cumulative percentage release of bupivacaine at 24-hour and 48-hour were compared to that of 134 batches of Exparel® produced by the 45 L process described herein, and 9 batches Exparel® produced by the UK 200 L process described herein. The results are summarized in Table 1.

TABLE 1

Average rate of change in % bupivacaine release comparison

| *Sample | 24-hour | 48-hour |
|---|---|---|
| Batch Nos. 1-5 average | 0.32%/month | 0.02%/month |
| 45 L batches average | −0.41%/month | −0.38%/month |
| UK 200 L batches | −0.20%/month | −0.33%/month |

*Only batches with complete IVRA data at all five time points (0 month, about 3 month, about 6 months, about 9 months and about 12 months) during the 12 months storage at 5° C. were included in the calculation.
**Only 126 batches produced by the 45 L process had 48-hour IVRA data at all five time points during the 12 months storage at 5° C.

Figure 3A:
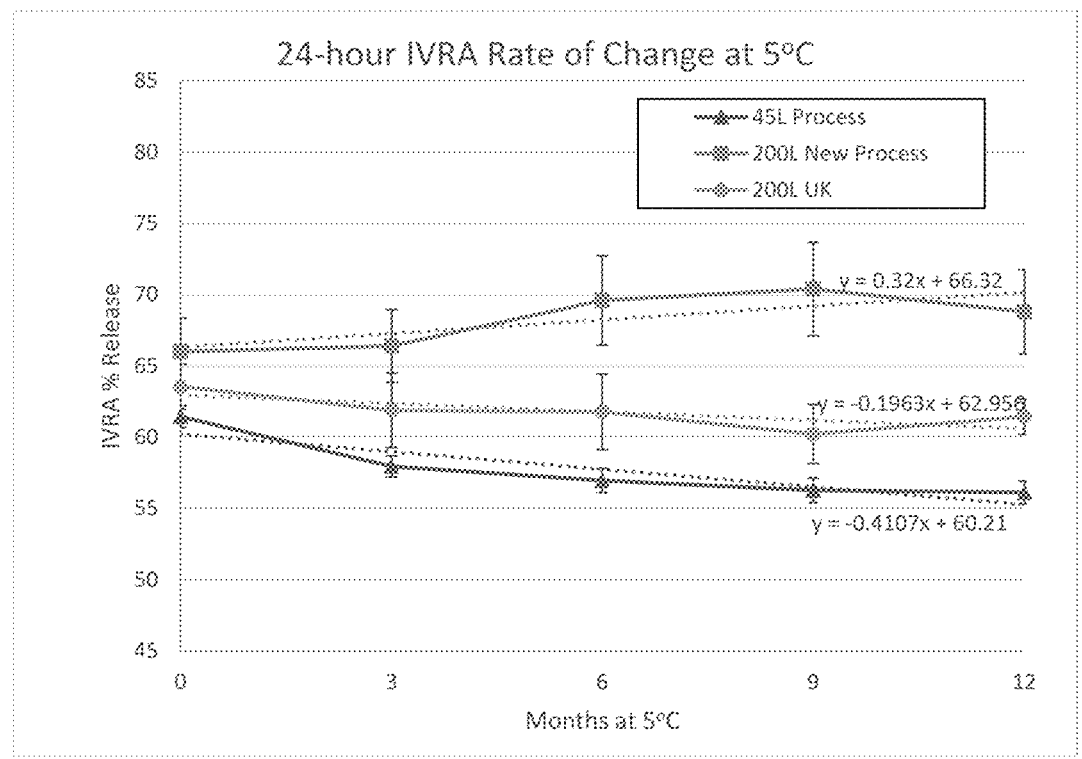
FIG. 3A is a line chart illustrating the average rate of change in cumulative percentage release of bupivacaine at 24-hour time point as a function of time, comparing batch samples according to certain embodiments of the present disclosure with batch samples manufactured by two known processes.
Figure 3B:
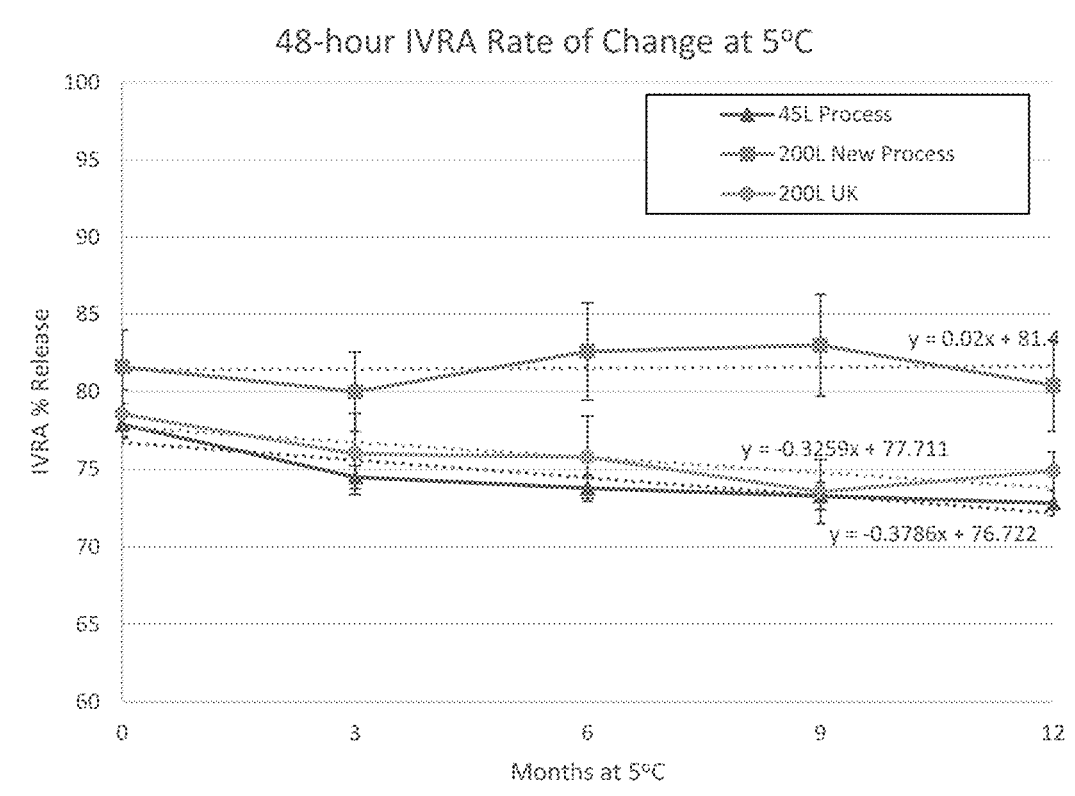
FIG. 3B is a line chart illustrating the average rate of change in cumulative percentage release of bupivacaine at 48-hour time point as a function of time, comparing bupivacaine MVLs batch samples according to certain embodiments of the present disclosure with bupivacaine MVLs batch samples manufactured by two known processes.

FIG. 3A is a line chart illustrating the average rate of change in cumulative percentage release of bupivacaine at 24-hour time point as a function of time over 12 months, comparing 5 batch samples produced by the present process with 134 batch samples manufactured by the 45 L process and 9 batch samples produced by the UK 200 L process. FIG. 3B is a line chart illustrating the average rate of change in cumulative percentage release of bupivacaine at 48-hour time point as a function of time over 12 months, comparing 5 batch samples produced by the present process with 126 batch samples manufactured by the 45 L process and 9 batch samples produced by the UK 200 L process. Error bars in FIGS. 3A and 3B represent a 95% confidence interval (CI), with values generated using the 95% CI and the standard error of the mean (SEM). The average cumulative percentage release of bupivacaine used to generate FIGS. 3A-3B are illustrated in Tables 2A, 2B and 2C, using the data presented in FIGS. 5A, 5B and 5C.

It was observed that the slope lines for the batches generated by the current process is either flat (48-hour) or trending slightly upward (24 hour). In contrast, the slope lines for the batches generated by both the 45 L process and the UK 200 L process are trending downward at both 24-hour and 48 hour. These figures suggest that the batches generated by the current process have improved IVRA stability profiles as compared to those produced by the 45 L and UK 200 L processes. In prior stability studies, it has been observed that the average % release of bupivacaine at 24-hour usually has a more pronounced decrease in the first 12-month, in particularly the first 6 months. Then the % release of bupivacaine continues to decrease during the second 12-month but the rate of decrease slows down. Because the IVRA test results need to remain within the product specification during the entire shelf life of the product, the flatter the trend line illustrating the rate of change in the cumulative percentage release of bupivacaine in the first 12 months, the more likely that the product will meet the IVRA specification during the entire 24 months. Furthermore, a slope line that trends upwards in the first 12-month can also compensate for or counteract the expected decrease in the % release in the second 12-month.

TABLE 2A

Batch % release of bupivacaine produced by the current process

| | 0 month | 3 months | 6 months | 9 months | 12 months |
|---|---|---|---|---|---|
| 24-hour average % release (n = 5) | 66 | 66 | 70 | 70 | 69 |
| STDev(S) | 1.87 | 2.61 | 3.91 | 4.22 | 2.39 |
| SEM | 0.84 | 1.17 | 1.75 | 1.89 | 1.07 |
| 95% CI | 1.64 | 2.29 | 3.43 | 3.70 | 2.09 |
| 24-hour average rate of change % release | | | 0.32%/month | | |
| 48-hour average % release (n = 5) | 82 | 80 | 83 | 83 | 80 |
| STDev(S) | 2.70 | 2.92 | 3.58 | 3.74 | 3.36 |
| SEM | 1.21 | 1.30 | 1.60 | 1.67 | 1.50 |
| 95% CI | 2.37 | 2.56 | 3.14 | 3.28 | 2.95 |
| 48-hour average rate of change % release | | | 0.02%/month | | |

TABLE 2B

Batch % release of bupivacaine produced by the 45 L process

| | 0 month | 3 months | 6 months | 9 months | 12 months |
|---|---|---|---|---|---|
| 24-hour average % release (n = 134) | 61 | 58 | 57 | 56 | 56 |
| STDev(S) | 4.80 | 4.53 | 4.48 | 5.01 | 5.11 |
| SEM | 0.41 | 0.39 | 0.39 | 0.43 | 0.44 |
| 95% CI | 0.81 | 0.77 | 0.76 | 0.85 | 0.86 |
| 24-hour average rate of change % release | | | −0.41%/month | | |

TABLE 2B-continued

Batch % release of bupivacaine produced by the 45 L process

|  | 0 month | 3 months | 6 months | 9 months | 12 months |
|---|---|---|---|---|---|
| 48-hour average % release (n = 126) | 78 | 74 | 74 | 73 | 73 |
| STDev(S) | 4.42 | 4.37 | 5.00 | 5.14 | 4.75 |
| SEM | 0.39 | 0.38 | 0.43 | 0.44 | 0.41 |
| 95% CI | 0.77 | 0.74 | 0.85 | 0.87 | 0.80 |
| 48-hour average rate of change % release | | | −0.38%/month | | |

TABLE 2C

Batch % release of bupivacaine produced by the UK 200 L process

|  | 0 month | 3 months | 6 months | 9 months | 12 months |
|---|---|---|---|---|---|
| 24-hour average % release (n = 9) | 64 | 62 | 62 | 60 | 61 |
| STDev(S) | 2.74 | 2.80 | 3.67 | 2.68 | 1.94 |
| SEM | 0.91 | 0.93 | 1.22 | 0.89 | 0.65 |
| 95% CI | 1.79 | 1.83 | 2.40 | 1.75 | 1.27 |
| 24-hour average rate of change % release | | | −0.20%/month | | |
| 48-hour average % release (n = 9) | 79 | 76 | 76 | 74 | 75 |
| STDev(S) | 2.40 | 4.00 | 4.06 | 3.17 | 1.90 |
| SEM | 0.80 | 1.33 | 1.35 | 1.06 | 0.63 |
| 95% CI | 1.57 | 2.61 | 2.65 | 2.07 | 1.24 |
| 48-hour average rate of change % release | | | −0.33%/month | | |

Example 2. Sample Comparison—Average Change in Cumulative Percentage Release of Bupivacaine In this example, 8 batches (Batch Nos. 1-8) of Exparel® (bupivacaine MVLs) produced by the new process according to certain embodiment of the present disclosure were stored at 5° C. for about 12 months after batch manufacture date. An IVRA test was performed at 0 month and about 12 months. The average change in cumulative percentage release of bupivacaine at 24-hour and 48-hour were compared to that of 140 batches of Exparel® produced by the 45 L process described herein, and 9 batches Exparel® produced by the UK 200 L process described herein. The results are summarized in Table 3.

TABLE 3

Average change in % bupivacaine release comparison

| Sample | 24-hour | 48-hour* |
|---|---|---|
| Batch Nos. 1-8 average | 2.5% | −0.3% |
| SD | 0.9 | 2.9 |
| 45 L batches average | −5.2% | −4.9% |
| SD | 4.8 | 4.2 |
| UK 200 L batches | −2.1% | −3.7% |
| SD | 2.6 | 1.8 |

*Only 132 batches produced by the 45 L process had 48-hour IVRA data at both 0 and 12 months during the 12 months storage at 5° C.

Figure 4A:
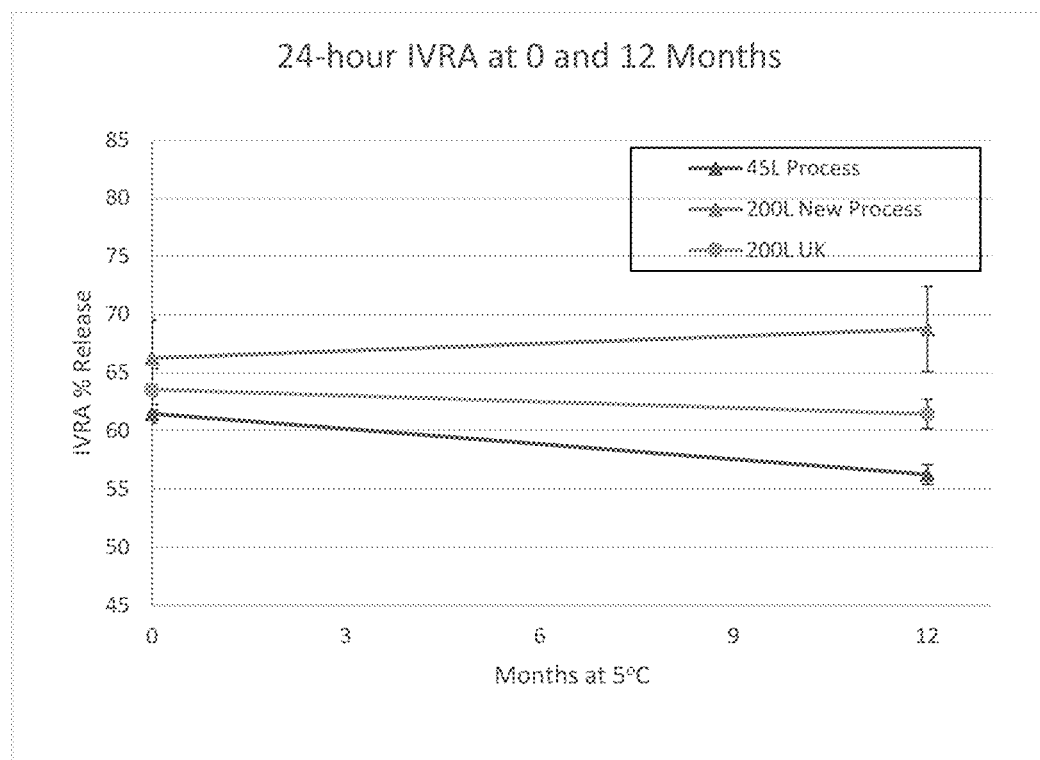
FIG. 4A is a line chart illustrating the average cumulative percentage release of bupivacaine at 24-hour time point at 0 and 12 months, comparing bupivacaine MVLs batch samples according to certain embodiments of the present disclosure with bupivacaine MVLs batch samples manufactured by two known processes.
Figure 4B:
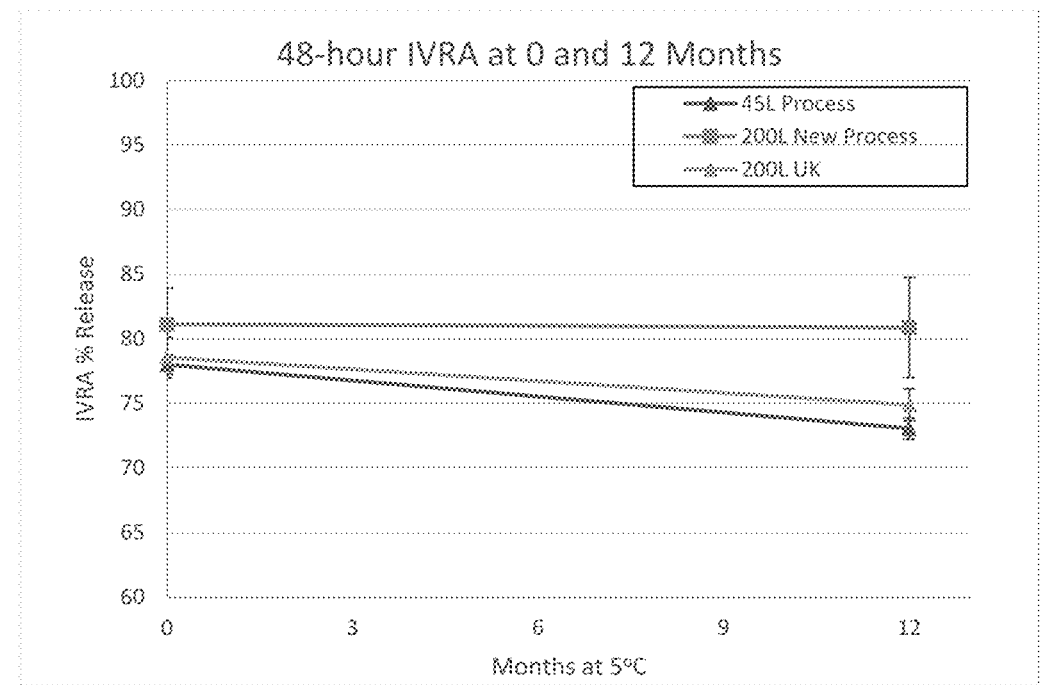
FIG. 4B is a line chart illustrating the average cumulative percentage release of bupivacaine at 48-hour time point at 0 and 12 months, comparing bupivacaine MVLs batch samples according to certain embodiments of the present disclosure with bupivacaine MVLs batch samples manufactured by two known processes.

FIG. 4A is a line chart illustrating the average cumulative percentage release of bupivacaine at 24-hour time point at 0 and 12 months, comparing 8 batch samples produced by the present process with 140 batch samples manufactured by the 45 L process and 9 batch samples produced by the UK 200 L process. FIG. 4B is a line chart illustrating the average cumulative percentage release of bupivacaine at 48-hour time point at 0 and 12 months, comparing 8 batch samples produced by the present process with 132 batch samples manufactured by the 45 L process and 9 batch samples produced by the UK 200 L process. Error bars in FIGS. 4A and 4B represent a 95% confidence interval (CI), with values generated using the 95% CI and the standard error of the mean (SEM). The average cumulative percentage release of bupivacaine used to generate FIGS. 4A-4B are illustrated in Tables 4A, 4B and 4C, using the data presented in FIGS. 5A-5F, 6 and 7. Consistent with the observation in the average rate of change in % bupivacaine release, the figures suggest that the batches generated by the current process have an improved IVRA profile as compared to those produced by the 45 L and UK 200 L processes.

TABLE 4A

Batch % release of bupivacaine produced by the current process

|  | 0 month | 12 months |
|---|---|---|
| 24-hour average % release (n = 8) | 66 | 69 |
| STDev(S) | 4.71 | 5.29 |
| SEM | 1.67 | 1.87 |
| 95% CI | 3.27 | 3.66 |
| 48-hour average % release (n = 8) | 81 | 81 |
| STDev(S) | 4.05 | 5.59 |
| SEM | 1.43 | 1.98 |
| 95% CI | 2.81 | 3.87 |

TABLE 4B

Batch % release of bupivacaine produced by the 45 L process

|  | 0 month | 12 months |
|---|---|---|
| 24-hour average % release (n = 140) | 61 | 56 |
| STDev(S) | 4.74 | 5.10 |
| SEM | 0.40 | 0.43 |
| 95% CI | 0.79 | 0.85 |
| 48-hour average % release (n = 132) | 78 | 73 |
| STDev(S) | 4.42 | 4.85 |
| SEM | 0.38 | 0.42 |
| 95% CI | 0.75 | 0.83 |

TABLE 4C

Batch % release of bupivacaine produced by the UK 200 L process

|  | 0 month | 12 months |
|---|---|---|
| 24-hour average % release (n = 9) | 64 | 61 |
| STDev(S) | 2.74 | 1.94 |
| SEM | 0.91 | 0.65 |
| 95% CI | 1.79 | 1.27 |
| 48-hour average % release (n = 9) | 79 | 75 |
| STDev(S) | 2.40 | 1.90 |
| SEM | 0.80 | 0.63 |
| 95% CI | 1.57 | 1.24 |

FIGS. 5A through 5F is a table illustrating the cumulative percentage release of bupivacaine at 24-hour and 48-hour after storage of the bupivacaine MVLs samples produced by the 45 L process at about 5° C. for about 0 months, 3 months, 6 months, 9 months and 12 months from manufacture date. FIG. 6 is a table illustrating the cumulative percentage release of bupivacaine at 24-hour and 48-hour after storage of the MVLs samples produced by the UK 200 L process at about 5° C. for about 0 months, 3 months, 6 months, 9 months and 12 months from manufacture date. FIG. 7 is a table illustrating the cumulative percentage release of bupivacaine at 24-hour and 48-hour after storage of the MVLs samples produced by process described herein at about 5° C. for about 0 months, 3 months, 6 months, 9 months and 12 months from manufacture date.

While the present application has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. Batches comprising compositions of bupivacaine encapsulated multivesicular liposomes (MVLs), the composition comprising:
   bupivacaine residing inside a plurality of internal aqueous chambers of MVLs separated by lipid membranes, wherein the lipid membranes comprise 1, 2-dierucoylphosphatidylcholine (DEPC), 1, 2-dipalmitoyl-sn-glycero-3-phospho-rac-(1-glycerol) (DPPG) or a salt thereof, cholesterol, and tricaprylin; and
   an aqueous medium in which the bupivacaine encapsulated MVLs are suspended, wherein the aqueous medium also comprises unencapsulated bupivacaine;
   the total bupivacaine concentration in the composition is from 12 mg/mL to 17 mg/mL;
   wherein the batches are manufactured within a period of six months, and each of the batches has a volume of about 100 liters to about 300 liters;
   wherein each batch has a cumulative percentage release of bupivacaine from 46% to 71% at a 24-hour time point, measured from two to six aliquots of each batch using a rotator-facilitated in vitro release assay for at least 48 hours, after storage of the aliquots of each batch at 2° C. to 8° C. for about 12 months from batch manufacture date; and
   wherein an average rate of change in the cumulative percentage release of bupivacaine of the batches at the 24-hour time point is 0.05%/month to 0.5%/month after storage of the aliquots of each batch at 2° C. to 8° C. for about 12 months.

2. The batches of claim 1, wherein the average rate of change in the cumulative percentage release of bupivacaine at the 24-hour time point is 0.08%/month to 0.5%/month.

3. The batches of claim 2, wherein the average rate of change in the cumulative percentage release of bupivacaine at the 24-hour time point is 0.1%/month to 0.4%/month.

4. The batches of claim 1, wherein each batch has a cumulative percentage release of bupivacaine from 60% to 85% at a 48-hour time point, and the average rate of change in the cumulative percentage release of bupivacaine at the 48-hour time point is −0.3%/month to 0.33%/month.

5. The batches of claim 4, wherein the average rate of change in the cumulative percentage release of bupivacaine at the 48-hour time point is −0.2%/month 0.03% month.

6. The batches of claim 5, wherein the average rate of change in the cumulative percentage release of bupivacaine at the 48-hour time point is from −0.18%/month to 0.28%/month.

7. The batches of claim 1, wherein the batches are manufactured within a period of 3 months.

8. The batches of claim 1, wherein the batches are manufactured within a period of 30 days.

9. The batches of claim 1, wherein the average rate of change in the cumulative percentage release of bupivacaine is based on three batches, and one batch is manufactured 10 or more days apart from at least one other batch.

10. The batches of claim 1, wherein the average rate of change in the cumulative percentage release of bupivacaine is based on two batches, and one batch is manufactured 10 or more days apart from the other batch.

11. The batches of claim 1, wherein the cumulative percentage release of bupivacaine of each batch is measured as the average of six aliquots from each batch.

12. The batches of claim 1, wherein each aliquot has a cumulative percentage release of bupivacaine from 36% to 81% at the 24-hour time point, and a cumulative percentage release of bupivacaine from 50% to 95% at the 48-hour time point.

13. The batches of claim 1, wherein the batches are manufactured within a period of 3 months, wherein the average rate of change in the cumulative percentage release of bupivacaine is based on three batches, and one batch is manufactured 10 or more days apart from at least one other batch, and wherein the cumulative percentage release of bupivacaine of each batch is measured as the average of six aliquots from each batch.

14. The batches of claim 1, wherein the batches are manufactured within a period of 30 days, wherein the average rate of change in the cumulative percentage release of bupivacaine is based on two batches, and one batch is manufactured 10 or more days apart from the other batch, and wherein the cumulative percentage release of bupivacaine of each batch is measured as the average of six aliquots from each batch.

15. The batches of claim 2, wherein the batches are manufactured within a period of 3 months, wherein the average rate of change in the cumulative percentage release of bupivacaine is based on three batches, and one batch is manufactured 10 or more days apart from at least one other batch, and wherein the cumulative percentage release of bupivacaine of each batch is measured as the average of six aliquots from each batch.

16. The batches of claim 2, wherein the batches are manufactured within a period of 30 days, wherein the average rate of change in the cumulative percentage release of bupivacaine is based on two batches, and one batch is manufactured 10 or more days apart from the other batch, and wherein the cumulative percentage release of bupivacaine of each batch is measured as the average of six aliquots from each batch.

17. The batches of claim 3, wherein the batches are manufactured within a period of 3 months, wherein the average rate of change in the cumulative percentage release of bupivacaine is based on three batches, and one batch is manufactured 10 or more days apart from at least one other batch, and wherein the cumulative percentage release of bupivacaine of each batch is measured as the average of six aliquots from each batch.

18. The batches of claim 3, wherein the batches are manufactured within a period of 30 days, wherein the average rate of change in the cumulative percentage release of bupivacaine is based on two batches, and one batch is manufactured 10 or more days apart from the other batch, and wherein the cumulative percentage release of bupivacaine of each batch is measured as the average of six aliquots from each batch.

19. Batches comprising compositions of bupivacaine encapsulated multivesicular liposomes (MVLs), the composition comprising:
  bupivacaine residing inside a plurality of internal aqueous chambers of MVLs separated by lipid membranes, wherein the lipid membranes comprise 1, 2-dierucoylphosphatidylcholine (DEPC), 1, 2-dipalmitoyl-sn-glycero-3-phospho-rac-(1-glycerol) (DPPG) or a salt thereof, cholesterol, and tricaprylin; and
  an aqueous medium in which the bupivacaine encapsulated MVLs are suspended, wherein the aqueous medium also comprises unencapsulated bupivacaine;
  the total bupivacaine concentration in the composition is from 12 mg/mL to 17 mg/mL;
  wherein the batches are manufactured within a period of six months, and each of the batches has a volume of about 100 liters to about 300 liters;
  wherein each batch has a cumulative percentage release of bupivacaine from 60% to 85% at a 48-hour time point, measured from two to six aliquots of each batch using a rotator-facilitated in vitro release assay for at least 48 hours, after storage of the aliquots of each batch at 2° C. to 8° C. for about 12 months from batch manufacture date; and
  wherein an average rate of change in the cumulative percentage release of bupivacaine of the batches at the 48-hour time point is −0.18%/month to 0.33%/month after storage of the aliquots of each batch at 2° C. to 8° C. for about 12 months.

20. The batches of claim 19, wherein the average rate of change in the cumulative percentage release of bupivacaine at the 48-hour time point is −0.15%/month to 0.30%/month.

21. The batches of claim 20, wherein the average rate of change in the cumulative percentage release of bupivacaine at the 48-hour time point is from −0.12%/month to 0.28%/month.

22. The batches of claim 19, wherein the batches are manufactured within a period of 3 months.

23. The batches of claim 19, wherein the batches are manufactured within a period of 30 days.

24. The batches of claim 19, wherein the average rate of change in the cumulative percentage release of bupivacaine is based on three batches, and one batch is manufactured 10 or more days apart from at least one other batch.

25. The batches of claim 19, wherein the average rate of change in the cumulative percentage release of bupivacaine is based on two batches, and one batch is manufactured 10 or more days apart from the other batch.

26. The batches of claim 19, wherein the cumulative percentage release of bupivacaine of each batch is measured as the average of six aliquots from each batch.

27. The batches of claim 19, wherein each aliquot has a cumulative percentage release of bupivacaine from 36% to 81% at a 24-hour time point, and a cumulative percentage release of bupivacaine from 50% to 95% at the 48-hour time point.

28. The batches of claim 19, wherein the batches are manufactured within a period of 3 months, wherein the average rate of change in the cumulative percentage release of bupivacaine is based on three batches, and one batch is manufactured 10 or more days apart from at least one other batch, and wherein the cumulative percentage release of bupivacaine of each batch is measured as the average of six aliquots from each batch.

29. The batches of claim 20, wherein the batches are manufactured within a period of 3 months, wherein the average rate of change in the cumulative percentage release of bupivacaine is based on three batches, and one batch is manufactured 10 or more days apart from at least one other batch, and wherein the cumulative percentage release of bupivacaine of each batch is measured as the average of six aliquots from each batch.

30. The batches of claim 21, wherein the batches are manufactured within a period of 3 months, wherein the average rate of change in the cumulative percentage release of bupivacaine is based on three batches, and one batch is manufactured 10 or more days apart from at least one other batch, and wherein the cumulative percentage release of bupivacaine of each batch is measured as the average of six aliquots from each batch.

\* \* \* \* \*